US010639235B2

(12) United States Patent
Banerji et al.

(10) Patent No.: US 10,639,235 B2
(45) Date of Patent: May 5, 2020

(54) SYSTEMS, APPARATUSES, DEVICES, AND PROCESSES FOR SYNERGISTIC NEURO-PHYSIOLOGICAL REHABILITATION AND/OR FUNCTIONAL DEVELOPMENT

(75) Inventors: Subhasis Banerji, Singapore (SG); Kok Hui John Gerard Heng, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 542 days.

(21) Appl. No.: 14/118,772

(22) PCT Filed: May 21, 2012

(86) PCT No.: PCT/SG2012/000177
§ 371 (c)(1),
(2), (4) Date: Feb. 17, 2014

(87) PCT Pub. No.: WO2012/161657
PCT Pub. Date: Nov. 29, 2012

(65) Prior Publication Data
US 2014/0200432 A1    Jul. 17, 2014

Related U.S. Application Data

(60) Provisional application No. 61/488,185, filed on May 20, 2011.

(51) Int. Cl.
*A61H 99/00* (2006.01)
*A61B 5/0478* (2006.01)
(Continued)

(52) U.S. Cl.
CPC ........... *A61H 99/00* (2013.01); *A61B 5/0478* (2013.01); *A61B 5/0482* (2013.01);
(Continued)

(58) Field of Classification Search
CPC ....... A61B 5/0482; A61B 5/743; A61B 5/165; A61B 5/0488; A61B 5/0478; A61B 5/048;
(Continued)

(56) References Cited

U.S. PATENT DOCUMENTS

| 8,214,029 B2 | 7/2012 | Koeneman et al. |
| 9,173,582 B2 | 11/2015 | Popovic et al. |

(Continued)

FOREIGN PATENT DOCUMENTS

| WO | 2005086574 A2 | 9/2005 |
| WO | 2007138598 A2 | 12/2007 |
| WO | 2010124247 A2 | 10/2010 |

OTHER PUBLICATIONS

Schepers et al., Functional recovery differs between ischaemic and haemorrhagic stroke patients, Journal of Rehabilitation Medicine., 2008, 487-489, vol. 40—Issue 6, Journal of Rehabilitation Medicine.

(Continued)

*Primary Examiner* — Michael C Grant
(74) *Attorney, Agent, or Firm* — Horizon IP PTE. LTD.

(57) ABSTRACT

A system for facilitating a subject's functional development includes sensing devices configured for sensing mind state signals; sensing devices configured for sensing body state signals; and a set of processing resources configured for generating a mind state indicator/measure, a body state indicator/measure, and a mind-body synergy indicator/measure that corresponds to which each of the subject's mind state and body state are synergistically aligned for facilitating the subject's functional development. The system can be configured for concurrently presenting a set of activities involving a model body part; engaging in attempted imitation of the set of activities by way of attempted movement of a body part that is a mirror image of the model body part;

(Continued)

presenting an indication of an extent to which each of the mind state and body state are cooperative with respect to performance of the set of activities; and presenting an indication of relaxation.

44 Claims, 60 Drawing Sheets

(51) Int. Cl.
| | |
|---|---|
| *G16H 50/30* | (2018.01) |
| *A61B 5/0488* | (2006.01) |
| *A61B 5/16* | (2006.01) |
| *A61B 5/0482* | (2006.01) |
| *A63B 24/00* | (2006.01) |
| *A63B 71/06* | (2006.01) |
| *G06F 3/01* | (2006.01) |
| *G06F 19/00* | (2018.01) |
| *G09B 19/00* | (2006.01) |
| *A63B 21/00* | (2006.01) |
| *A61B 5/00* | (2006.01) |
| *A61B 5/11* | (2006.01) |
| *A61M 21/02* | (2006.01) |
| *A61N 1/36* | (2006.01) |
| *A61B 5/22* | (2006.01) |
| *A63B 23/14* | (2006.01) |
| *A63B 23/12* | (2006.01) |
| *A63B 22/00* | (2006.01) |
| *A61B 5/048* | (2006.01) |

(52) U.S. Cl.
CPC .......... *A61B 5/0488* (2013.01); *A61B 5/1125* (2013.01); *A61B 5/162* (2013.01); *A61B 5/165* (2013.01); *A61B 5/743* (2013.01); *A61B 5/7445* (2013.01); *A61M 21/02* (2013.01); *A63B 21/00181* (2013.01); *A63B 21/4017* (2015.10); *A63B 21/4019* (2015.10); *A63B 21/4035* (2015.10); *A63B 21/4045* (2015.10); *A63B 24/0059* (2013.01); *A63B 24/0062* (2013.01); *A63B 71/0622* (2013.01); *G06F 3/014* (2013.01); *G06F 3/015* (2013.01); *G06F 19/3418* (2013.01); *G06F 19/3481* (2013.01); *G09B 19/003* (2013.01); *G16H 50/30* (2018.01); *A61B 5/048* (2013.01); *A61B 5/04888* (2013.01); *A61B 5/1107* (2013.01); *A61B 5/224* (2013.01); *A61B 5/7475* (2013.01); *A61B 2505/09* (2013.01); *A61N 1/36003* (2013.01); *A63B 23/1209* (2013.01); *A63B 23/14* (2013.01); *A63B 2022/0094* (2013.01); *A63B 2024/0065* (2013.01); *A63B 2024/0068* (2013.01); *A63B 2024/0096* (2013.01); *A63B 2071/0647* (2013.01); *A63B 2071/0655* (2013.01); *A63B 2213/004* (2013.01); *A63B 2225/20* (2013.01); *A63B 2225/50* (2013.01); *A63B 2230/06* (2013.01); *A63B 2230/08* (2013.01); *A63B 2230/10* (2013.01); *A63B 2230/207* (2013.01); *A63B 2230/30* (2013.01); *A63B 2230/42* (2013.01); *A63B 2230/60* (2013.01)

(58) Field of Classification Search
CPC . A61B 5/1107; A61B 2505/09; A61B 5/7475; A61B 5/04888; A61B 5/224; A61H 99/00; A63B 21/4045; A63B 21/4017; A63B 21/4019; A63B 21/4035; A63B 5/1125; A63B 5/7445; A63B 5/162; A63B 21/00181; A63B 24/0059; A63B 2022/0094; A63B 2230/06; A63B 2230/207; A63B 2230/42; A63B 2071/0647; A63B 2230/10; A63B 2024/0096; A63B 2225/50; A63B 2230/30; A63B 23/1209; A63B 23/14; A63B 2230/60; A63B 2071/0655; A63B 225/20; A63B 2024/0068; A63B 2024/0065; A63B 2230/08; A63B 2213/004; G06F 19/3418; G06F 3/014; G06F 19/3481; G06F 3/015; G09B 19/003; G16H 50/30; A61M 21/02; A61N 1/36003
USPC ........................................................ 434/258
See application file for complete search history.

(56) References Cited

U.S. PATENT DOCUMENTS

| | | | |
|---|---|---|---|
| 2006/0057549 A1* | 3/2006 | Prinzel, III | A61B 5/0002 434/247 |
| 2007/0167690 A1 | 7/2007 | Miyazaki et al. | |
| 2007/0179534 A1* | 8/2007 | Firlik | A61M 5/14276 607/3 |
| 2009/0221928 A1* | 9/2009 | Einav | A61B 5/0484 600/544 |
| 2011/0105862 A1* | 5/2011 | Gies | A61B 5/0006 600/301 |
| 2012/0310050 A1* | 12/2012 | Osorio | A61B 5/4094 600/300 |
| 2013/0281798 A1* | 10/2013 | Rau | A61B 5/4884 600/301 |
| 2014/0200632 A1* | 7/2014 | An | A61B 5/0482 607/62 |
| 2015/0312626 A1* | 10/2015 | Hoctor | H04N 21/251 725/12 |

OTHER PUBLICATIONS

Hantikainen V et al., Movement support based on Kinaesthetics and the development and improvement of body perception, movement abilities and functional independency of elderly nursing home residents., Pflege, Feb. 11-22, 2006, vol. 19—Issue 1, Hoegrefe.
Casady et al., the effect of hippotherapy on ten children with cerebral palsy., Pediatr Phys Ther, 2004, 165-172, vol. 16—Issue 3, Wolters Kluwer.
Olai et al., Prognosis assessment in stroke patients at discharge from hospital., Age and Ageing, Mar. 1, 2007, 184-189, vol. 36—Issue 2, Oxford University Press.
Demir et al., Functional and cognitive progress in aphasic patients with traumatic brain injury during post-acute phase., Brain Injury, 2006, 1-8, informa healthcare.

\* cited by examiner

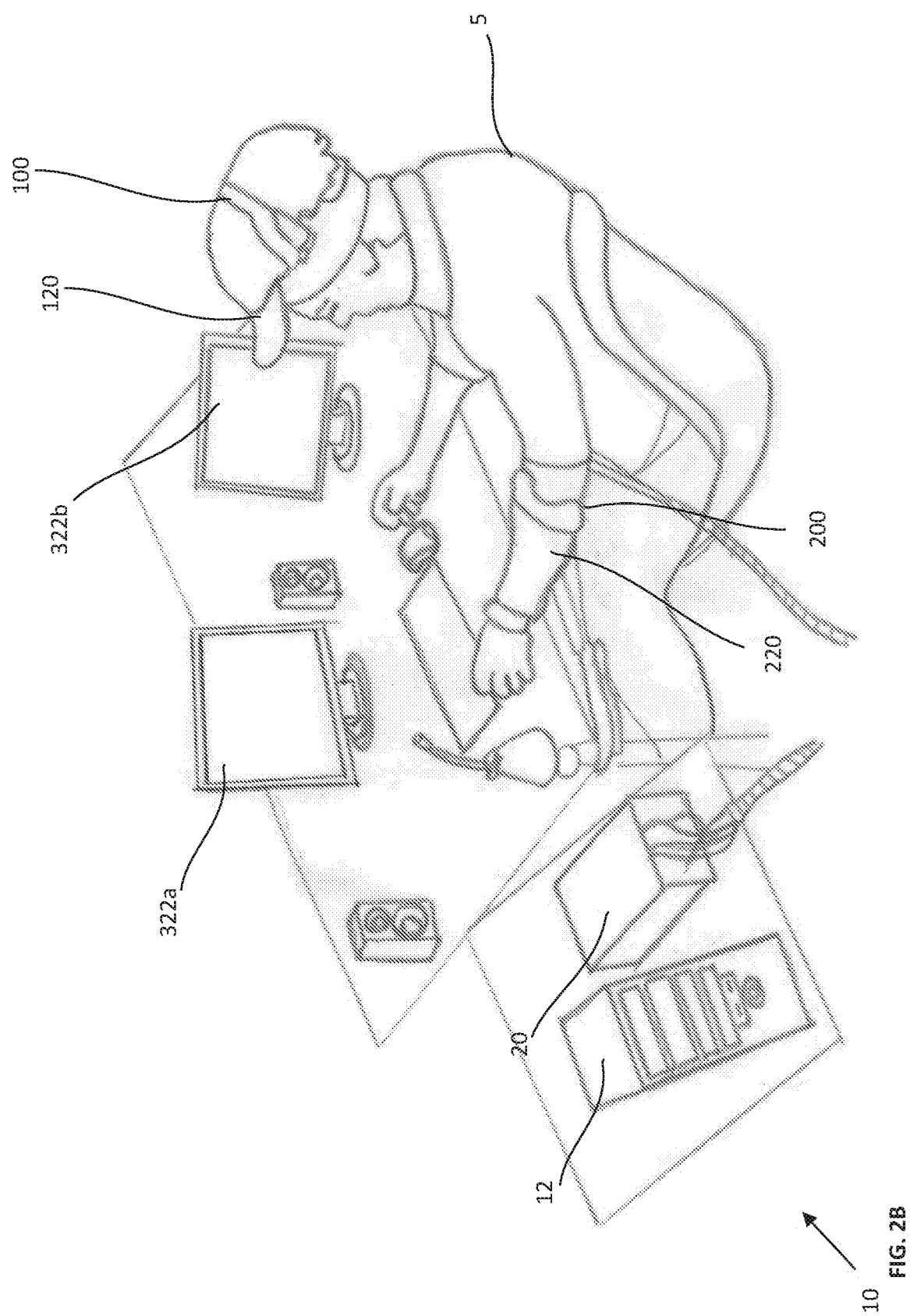

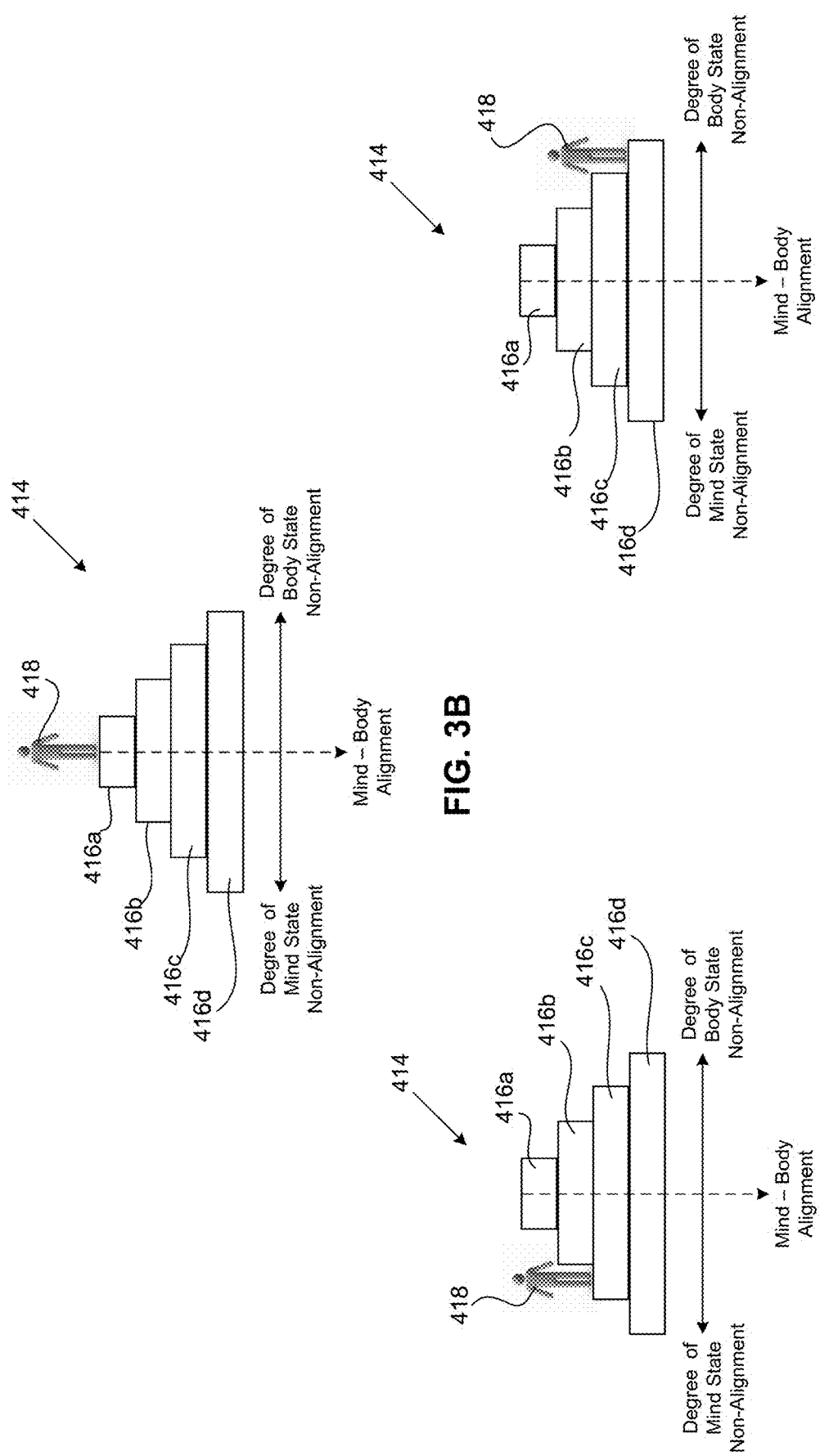

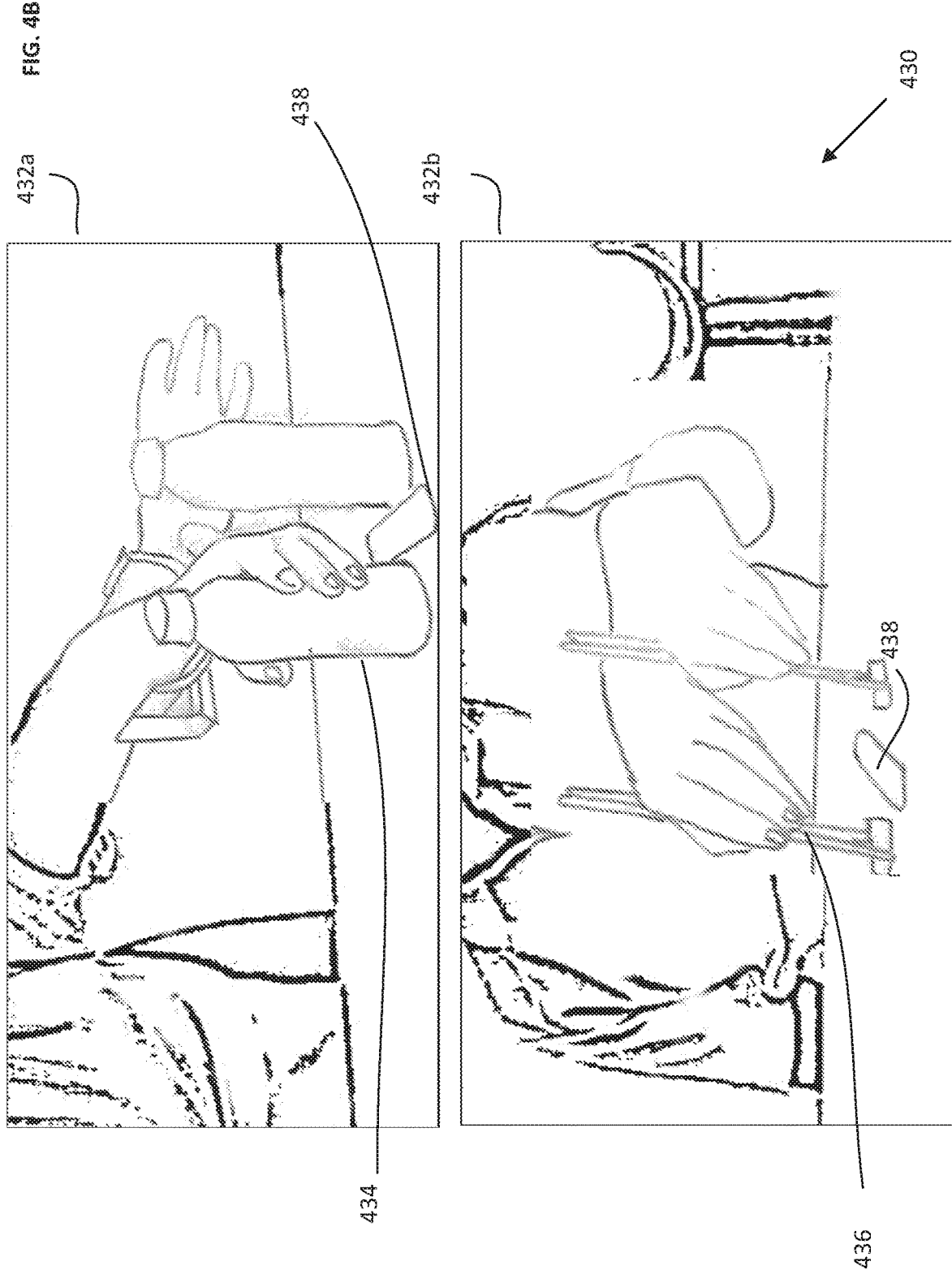

542

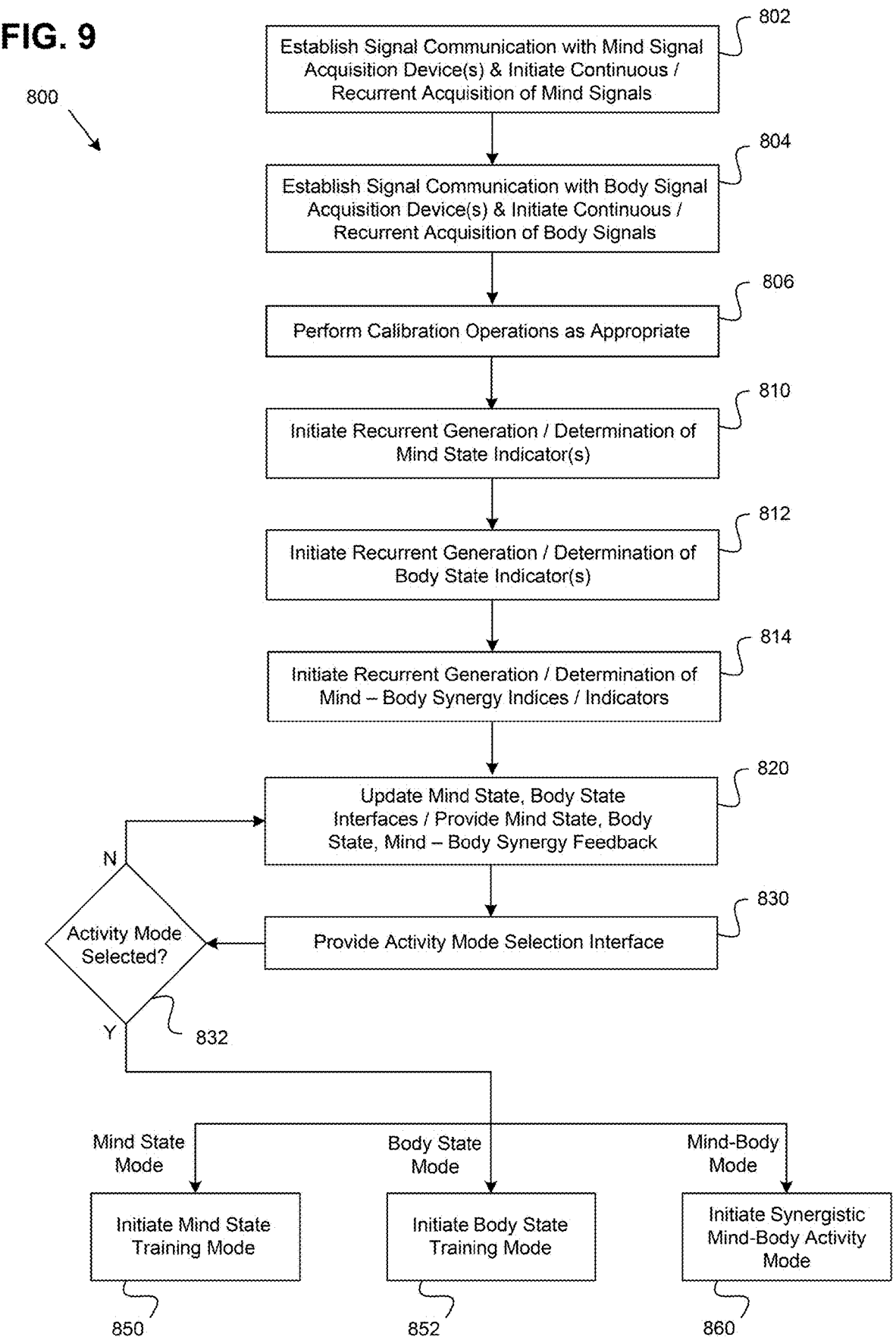

FIG. 16E

SynPhNe Report

Client Name: Admin
Date: 4/28/2012  Time: 12:23:17 PM

Settings:

Threshold: ☐ 20  ☒ 40  ☐ 60

FES Threshold: 5 %  FES: ON

Intensity: ☒ Normal  ☐ Low  ☐ High  ☐ Auto

Summary:

Total Time: 63.8 min
Total Expected Reps: 75
Total Successful Reps: 20
Playlist:
Average Intensity: 1

| Routine | Reps | Successful |
|---|---|---|
| INT-R | 0 | 0 |
| REL-ER | 0 | 0 |
| REL-R | 5 | 0 |
| SE-ER | 0 | 0 |
| SE-R | 5 | 0 |
| SF-R | 5 | 0 |
| WE-ER | 0 | 0 |
| WE-R | 5 | 0 |
| WF-R | 5 | 0 |
| FE-ER | 0 | 0 |
| FE-R | 5 | 2 |
| FF-R | 5 | 1 |
| PRO-ER | 0 | 0 |
| PRO-R | 5 | 0 |
| SUP-R | 5 | 0 |
| OG-ER | 0 | 0 |
| OG-R | 5 | 5 |
| FFR-ER | 0 | 0 |
| FFR-R | 5 | 1 |
| T1PEN-ER | 0 | 0 |
| T1PEN-R | 5 | 5 |
| T2BOT-ER | 0 | 0 |
| T2BOT-R | 5 | 0 |
| T3PG-ER | 0 | 0 |
| T3PG-R | 5 | 0 |
| T4CHP-ER | 0 | 0 |
| T4CHP-R | 5 | 0 |
| | 75 | 20 |

| Abbreviation | Full Name |
|---|---|
| INT-R | Introduction |
| REL-ER | Relaxation Explanation |
| REL-R | Relaxation |
| SE-ER | Small Extensions Explanation |
| SE-R | Small Extensions (E) |
| SF-R | Small Extensions (F) |
| WE-ER | Wrist Extension Explanation |
| WE-R | Wrist Extension (E) |
| WF-R | Wrist Extension (F) |
| FE-ER | Finger Extension Explanation |
| FE-R | Finger Extension (E) |
| FF-R | Finger Extension (F) |
| PRO-ER | Pronation Supination Explanation |
| PRO-R | Pronation Supination (P) |
| SUP-R | Pronation Supination (S) |
| OG-ER | Wrist & Fingers Explanation |
| OG-R | Wrist & Fingers |
| FFR-ER | Fingers & Forearm Rotation Explanation |
| FFR-R | Fingers & Forearm Rotation |
| T1PEN-ER | Picking Up a Pen Explanation |
| T1PEN-R | Picking Up a Pen |
| T2BOT-ER | Grasping a Bottle Explanation |
| T2BOT-R | Grasping a Bottle |
| T3PG-ER | Flipping the Pages Explanation |
| T3PG-R | Flipping the Pages |
| T4CHP-ER | The Use of Chopsticks Explanation |
| T4CHP-R | The Use of Chopsticks |
| END | End |

FIG. 20C

SYSTEMS, APPARATUSES, DEVICES, AND PROCESSES FOR SYNERGISTIC NEURO-PHYSIOLOGICAL REHABILITATION AND/OR FUNCTIONAL DEVELOPMENT

TECHNICAL FIELD

The present disclosure generally relates to systems, apparatuses, and techniques that facilitate a subject's performance of rehabilitation, functional development, or functional maintenance activity sequences, and which provide biofeedback to the subject. More particularly, embodiments of the present disclosure are directed to rehabilitation, functional development, and/or functional maintenance systems and techniques that (a) capture mind signals and body signals from a subject; (b) generate a set of mind state indicators and a set of body state indicators corresponding to the subject's mind state and body state; (c) provide mind state and body state biofeedback to the subject; and (d) adaptively manage the provision of rehabilitation, functional development, and/or functional maintenance activity sequences, mind state exercises, and body state exercises to the subject based upon whether the subject's mind state and body state are conducive to activity performance and/or learning, neuroplasticity, or neural reorganization.

BACKGROUND

Conventional systems, devices, and techniques directed toward the restoration, rehabilitation, or development of a subject's functional capabilities have failed to give rise to significant and/or lasting increases in subject functional capabilities, and have particularly failed to significantly enhance an expectation or likelihood that an individual can attain a "breakthrough" or sudden/dramatic/unexpected surge in their functional capabilities.

For instance, for individuals who are functionally impaired as a result of neurologic damage (e.g., resulting from a stroke or traumatic brain injury), such individuals are typically treated using physical therapy to rehabilitate the loss of function of a limb or another affected body part. For many patients, little can be done to improve the function of the affected limb significantly beyond the recovery that occurs naturally without intervention. One existing physical therapy technique for treating stroke patients constrains or restrains the use of a working body part of the patient to force the patient to use the affected body part. For example, the loss of use of a limb is treated by restraining the other limb. Although this type of physical therapy has shown some experimental efficacy, it can be frustrating, time-consuming, therapist intensive (and hence expensive), and limited in its efficacy, and hence has not been widely adopted.

A need exists for developing truly effective systems, devices, and techniques for restoring, rehabilitating, or developing a subject's functional capabilities. Such systems should be capable of facilitating functional gains under conditions that are expected to synergistically enhance or optimize subject functional performance, learning, and/or favourable neural reorganization/neuroplasticity, such that breakthrough functional gains can more readily occur. Such systems should further be capable of use in a manner that is significantly or substantially subject independent, i.e., which requires little or minimal therapist involvement.

SUMMARY

In accordance with an aspect of the present disclosure, a system for facilitating a subject's functional development includes a first set of sensing devices configured for sensing signals corresponding to the subject's mind state; a second set of sensing devices configured for sensing signals corresponding to the subject's body state; and a set of processing resources configured for generating a mind-body synergy measure that corresponds to an expected extent to which each of the subject's mind state and the subject's body state are cooperatively aligned with respect to facilitating the subject's functional development. The first set of sensing devices can include a set of devices (e.g., EEG sensing elements) configured for detecting signals representative of intracranial neural activity, and the second set of sensing devices can include a set of devices (e.g., EMG sensing elements) configured for detecting signals corresponding to peripheral nervous system activity.

The set of processing resources is configured for generating each of (a) a mind state alignment measure corresponding to an expected extent to which the subject's mental activity is conducive to learning, and (b) a body state alignment measure corresponding to an expected extent to which the subject's bodily activity is conducive to successfully performing a functional development activity. The mind state alignment measure can correspond to at least one of a level of stress, a level of anxiety, a level of mental relaxation, and a level of mental attention or focus. In particular embodiments, the mind state alignment measure is correlated with a ratio between a mean relative alpha band power measure $\overline{P_\alpha}$ and a delta-to-alpha measure DAR referenced to a particular time t, normalized to a baseline or at rest ratio between the mean relative alpha measure $\overline{P_\alpha}$ and the delta-to-alpha measure DAR.

The body state alignment measure can correspond to a measure of agonist-antagonist muscle contraction. In particular embodiments, the body state alignment measure is correlated with a difference between a measure of voluntary target agonist muscle contraction and a measure of voluntary target antagonist muscle contraction.

The mind-body synergy measure can include a breakthrough measure that is expected to correspond to a likelihood that the subject's mind state and body state can synergistically facilitate at least one of substantial, accelerated, sudden, nonlinear, surprising, spontaneous, and lasting gains in functional capability. The breakthrough measure can be correlated with a voluntary muscle contraction measure that (a) meets or exceeds a threshold muscle contraction condition, and which (b) is temporally associated with each of the mind state alignment measure satisfying a mind state alignment condition and the body state alignment measure satisfying a body state alignment condition.

In accordance with a further aspect of the present disclosure, a system can include a set of display devices configured for presenting to the subject each of a visual functional development activity sequence and a visual representation of at least one of the mind-body synergy measure, a measure of subject relaxed mental attention, a measure of subject bodily tension, a measure of subject heart rate, a measure of subject skin conductance, a measure of subject sweat, a measure of subject blood oxygenation, and a target subject breathing rate. The set of display devices is typically configured for presenting a visual functional development activity sequence that conveys at least one target movement of at least one model body part, the visual functional development activity sequence intended for at least one of performance, attempted performance, and imagined performance by the subject by way of at least one subject body part that is a mirror image of the at least one model body part. The set of display devices can additionally or alternatively be configured for (a) presenting to the subject a visual representation of a level of subject activation of each of an agonist muscle and an antagonist muscle associated with subject performance or attempted performance of the functional development activity sequence; and/or (b) selectively presenting mind state training exercises and body state training exercises to the subject. In various embodiments, at least a portion of the system is wearable by the subject, and in some embodiments, the entire or substantially the entire system is subject wearable.

In accordance with another aspect of the present disclosure, a system can include comprising at least one of a robotic orthosis configured for providing movement assistance to the subject and a functional electrical stimulation (FES) apparatus configured for delivering FES signals to the subject. A robotic orthosis can include a set of appendage motion modules configured for engaging with a portion of a subject appendage; a set of mechanical power interface modules coupled to the set of appendage motion modules and configured for facilitating movement of appendage motion modules within the set of appendage motion modules; and a set of flexible drive shafts couplable to the set of mechanical power interface modules and a set of motors external to the wearable robotic orthosis, wherein the set of appendage motion modules and the set of mechanical power interface modules are subject wearable. The set of appendage motion modules can include multiple independently operable and selectively detachable appendage motion modules.

In accordance with an aspect of the present disclosure, a process for facilitating functional development of a subject includes sensing signals corresponding to the subject's mind state; sensing signals corresponding to the subject's body state; and generating a mind-body synergy measure that corresponds to an expected extent to which each of the subject's mind state and the subject's body state are cooperatively aligned with respect to facilitating the subject's functional development. Sensing signals corresponding to the subject's mind state can include detecting signals (e.g., EEG signals) representative of intracranial neural activity. Sensing signals corresponding to the subject's body state can include detecting signals (e.g., EMG signals) corresponding to peripheral nervous system activity.

In accordance with a further aspect of the present disclosure, a process includes generating each of (a) a mind state alignment measure corresponding to an expected extent to which the subject's mental activity is conducive to learning, and (b) a body state alignment measure corresponding to an expected extent to which the subject's bodily activity is conducive to successfully performing a functional development activity. Sensing signals corresponding to the subject's mind state, sensing signals corresponding to the subject's body state, and/or generating the mind-body synergy measure can occur during one of subject involvement in a therapy session and subject performance or attempted performance of activities of daily living.

In various embodiments, the mind state alignment measure can correspond to at least one of a level of stress, a level of anxiety, a level of mental relaxation, and a level of mental attention or focus. In particular embodiments, the mind state alignment measure is correlated with a ratio between a mean relative alpha band power measure $\overline{P_\alpha}$ and a delta-to-alpha measure DAR referenced to a particular time t, normalized to a baseline or at rest ratio between the mean relative alpha measure $\overline{P_\alpha}$ and the delta-to-alpha measure DAR.

The body state alignment measure can correspond to a measure of agonist-antagonist muscle contraction. In particular embodiments, the body state alignment measure is correlated with a difference between a measure of voluntary target agonist muscle contraction and a measure of voluntary target antagonist muscle contraction.

In accordance with another aspect of the present disclosure, the mind-body synergy measure includes a breakthrough measure that is expected to correspond to a likelihood that the subject's mind state and body state can synergistically facilitate at least one of substantial, accelerated, sudden, nonlinear, surprising, spontaneous, and lasting gains in functional capability. The breakthrough measure can be correlated with a voluntary muscle contraction measure that (a) meets or exceeds a threshold muscle contraction condition, and which (b) is temporally associated with each of the mind state alignment measure satisfying a mind state alignment condition and the body state alignment measure satisfying a body state alignment condition.

In accordance with a further aspect of the present disclosure, a process includes presenting to the subject each of a visual functional development activity sequence and a visual representation of at least one of the mind-body synergy measure, a measure of subject relaxed mental attention, a measure of subject bodily tension, a measure of subject heart rate, a measure of subject skin conductance, a measure of subject sweat, a measure of subject blood oxygenation, and a target subject breathing rate.

Presenting a visual functional development activity sequence can include presenting at least one target movement of at least one model body part, the visual functional development activity sequence intended for at least one of performance, attempted performance, and imagined performance by the subject by way of at least one subject body part that is a mirror image of the at least one model body part. Aspects of the present disclosure can additionally or alternatively include presenting to the subject a visual representation of a level of subject activation of each of an agonist muscle and an antagonist muscle associated with subject performance or attempted performance of the functional development activity sequence.

In accordance with another aspect of the present disclosure, a process can include selectively presenting to the subject a set of mind state training exercises in the event that a set of mind state alignment measures corresponds to a subject mind state that is expected to be counterproductive to subject functional development. The process can further include automatically resuming presentation of the functional development activity sequence to the subject following presentation of the set of mind state training exercises to the subject. A process can additionally or alternatively include selectively presenting to the subject a set of body state training exercises in the event that a set of body state alignment measures corresponds to a subject body state that is expected to be counterproductive to subject functional development.

In accordance with another aspect of the present disclosure, a process can include mounting a wearable robotic orthosis to a portion of a subject appendage; and providing assistive movement to the subject appendage by way of the wearable robotic orthosis during subject performance or attempted performance of at least one of a functional development activity sequence and an activity of daily living.

A process in accordance with an aspect of the present disclosure can include presenting to the subject a set of activities involving a model body part; simultaneously engaging the subject in attempted imitation of the set of activities by way of attempted movement of a subject body part that is a mirror image of the model body part; simultaneously presenting to the subject an indication of an expected extent to which each of the subject's mind state and body state are cooperative with respect to subject performance of the set of activities; and simultaneously presenting to the subject an indication of an extent of subject relaxation.

In accordance with another aspect of the present disclosure, a robotic orthosis system configured for providing assistive movement to a portion of an appendage of a subject includes a set of appendage motion modules configured for engaging with a portion of a subject appendage; a set of mechanical power interface modules coupled to the set of appendage motion modules and configured for facilitating movement of appendage motion modules within the set of appendage motion modules; and a set of flexible drive shafts couplable to the set of mechanical power interface modules, wherein the set of appendage motion modules and the set of mechanical power interface modules are subject wearable. The robotic orthosis system can include a set of motors external to the subject wearable robotic orthosis, the set of motors couplable to the set of mechanical power interface modules by way of the set of flexible drive shafts.

In accordance with a further aspect of the present disclosure, an EEG headset can include at least one flexible band configured for fittable engagement with a subject's head; and a set of dry EEG electrode assemblies carried by the at least one flexible band, each dry EEG electrode assembly comprising an array of resiliently biased EEG sensing elements, wherein the set of dry EEG electrode assemblies are position adjustable relative to each of an anterior-posterior direction and a superior-inferior direction.

BRIEF DESCRIPTION OF THE DRAWINGS

FIGS. 2A-2C are schematic illustrations of subjects interacting with representative embodiments of systems configured for facilitating particular types of neurological-physiological rehabilitation and/or functional development in accordance with the present disclosure.

FIGS. 3B-3D are schematic illustrations of a representative embodiment of a visual mind-body alignment feedback element configured for visually conveying current mind state alignment and body state alignment related information to a subject.

FIGS. 4A and 4B respectively depict a representative first functional development activity sequence interface according to an embodiment of the disclosure and a representative second functional development activity interface according to an embodiment of the disclosure.

FIG. 9 is a flow diagram of a representative unified neurological-physiological rehabilitation and/or functional development process according to an embodiment of the disclosure.

FIGS. 16A-16I are representative visual interfaces for configuring system options/parameters associated with mind signals ("Thought"), body signals ("Purpose"), activity intensity ("Energy"), activity sequences and training games ("Action"), mind signal and body signal definitions/sources ("Effect"), and Functional Electrical Stimulation (FES).

FIGS. 20A-20C are representative reports for presenting various types of subject performance metrics.

DETAILED DESCRIPTION

Figure 1:
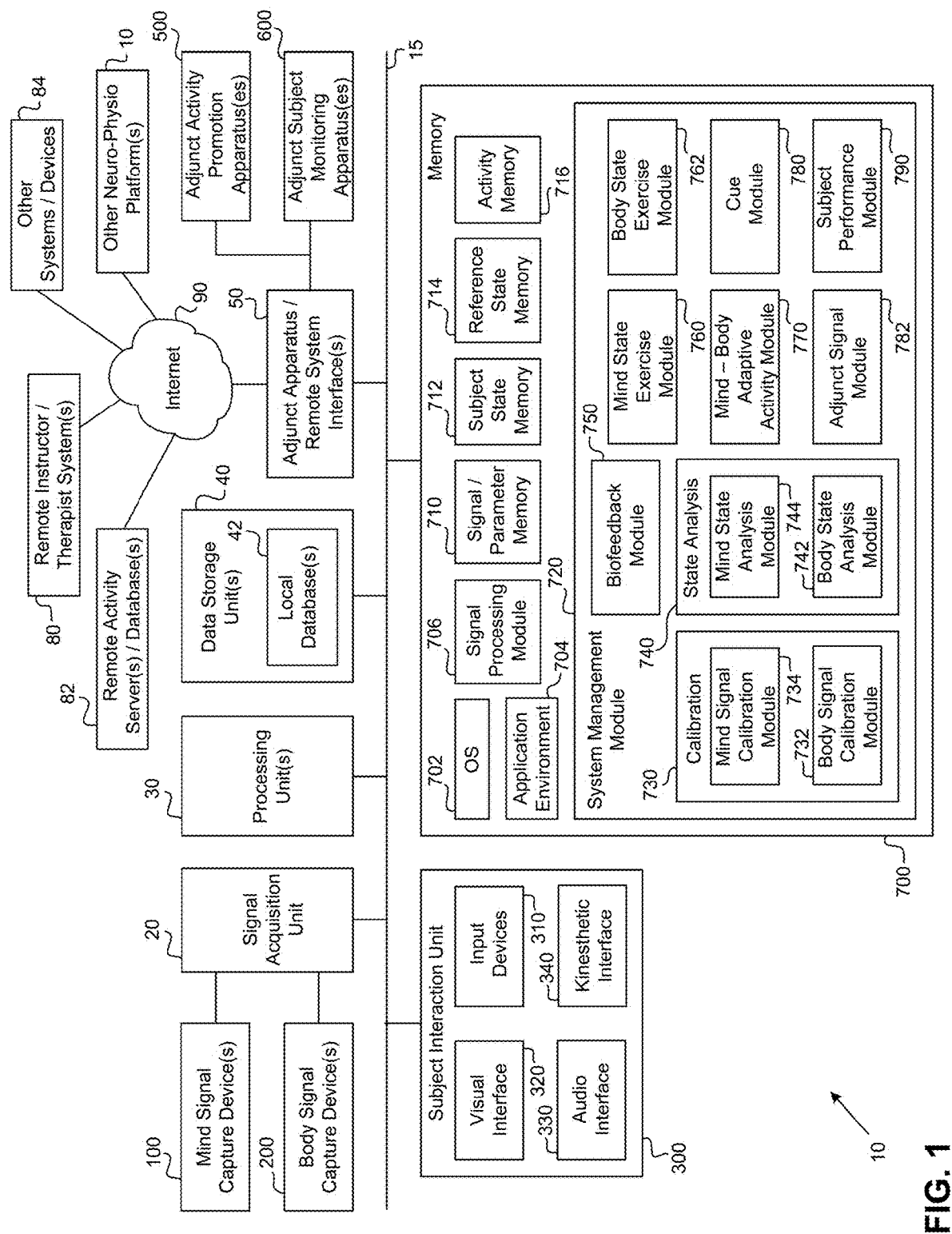
FIG. 1 is a block diagram of a system or platform for unified and/or synergistic neurological-physiological rehabilitation and/or functional development according to particular embodiments of the disclosure.

A subject's neurological or mind state(s), physiological or body state(s), and ongoing neurological-physiological feedback or regulation processes can have a significant or dramatic influence upon the subject's ability to perform an activity or task, as well as an extent to which the subject is capable of successfully learning or experiencing favorable task related neuroplasticity or neural reorganization. Embodiments of the present disclosure are directed to systems, apparatuses, devices, techniques, and processes that can facilitate the cooperative coordination or alignment of a subject's neurological or mind state and physiological or body state with the subject's observation, visualization, attempted performance, and/or performance of one or more rehabilitation, functional development, and/or functional maintenance activity sequences. The cooperative coordination of the subject's mind state and body state simultaneous with subject engagement in one or more of such activity sequences can synergistically accelerate, enhance, and/or sustain the subject's functional development or improvement, learning, and/or favorable neuroplasticity or neural reorganization associated therewith.

A subject's mental activities or mental processes and physical activities or physical processes are controlled by biological signals, which are generated in association with or as a result of subject internal or subject intrinsic biological phenomena. In the context of the present disclosure, biological signals include monitorable or measurable a) mind signals; and b) body signals. Mind signals represent, characterize, typify, constitute, or are counterparts to a subject's mental activities or mental processes, such as cognitive and/or emotional processes. Body signals represent, characterize, typify, constitute, or are counterparts to the subject's bodily, somatic, or corporeal activities or processes, such as movement or attempted movement of one or more body parts, or an extent to which particular muscles are contracted or relaxed.

A subject's mind state and body state can be estimated, indicated, calculated, evaluated, analyzed, or determined based upon mind signals and body signals that are captured or acquired from the subject. Various embodiments of the present disclosure generate, derive, or calculate mind state indicators and body state indicators from mind signals and body signals, respectively. Mind state indicators correspond to, are expected to correspond to, or are reflective of a state or condition of the subject's mind or psyche at a particular time. Body state indicators correspond to, are expected to correspond to, or are reflective of a state or condition of particular subject body parts (e.g., muscles, peripheral nervous system pathways, and/or certain organs such as the heart) at a particular time, by which the subject can interact, attempt to interact, or interface with and/or react to their external environment.

In general, as a result of inherent mind-body interaction, coupling, integration, or feedback, mind signals can influence, lead, coordinate, or drive the generation, expression, or evolution of body signals; and body signals can influence, lead, coordinate, or drive the generation, expression, or evolution of mind signals. Representative types of mind signals, mind state indicators, body signals, and body state indicators are described in detail below.

Various embodiments of the present disclosure are directed to systems, apparatuses, devices, techniques, and processes configured for capturing or retrieving a subject's mind signals and body signals; process mind signals and body signals to generate mind state indicators and body state indicators therefrom; provide mind state and body state biofeedback to the subject; selectively present functional development activity sequences, mind state exercises, and body state exercises to the subject; detect and/or monitor the subject's observation, visualization, attempted performance, or performance of functional development activity sequences, mind state exercises, and body state exercises; and automatically adapt functional activity sequence parameters and/or a transition to a mind state regulation, relaxation, training, or exercise mode or a body state regulation, relaxation, training, or exercise mode based upon the subject's current mind state and body state during the subject's observation, visualization, attempted performance, or performance of functional development activity sequences.

In general, a functional development activity sequence includes audio and/or visual information presented to the subject, which corresponds to one or more representative, example, demonstrated, or idealized activities, tasks, scenarios, situations, or behaviors in which the subject is to visualize, attempt to engage, or engage. Any given functional development activity sequence is intended to facilitate the rehabilitation, restoration, or development of one or more types of physical (e.g., motor and/or sensory), cognitive, and/or emotional subject capabilities. In association with or during the presentation of a functional development activity sequence to the subject, the subject can visualize, attempt to perform, and/or perform one or more activities, tasks, actions, or behaviors indicated by the functional development activity sequence. Depending upon the nature of a subject capability currently under consideration for development, subject performance or attempted performance of functional development activities can involve the subject's interaction with or manipulation of various types of objects (e.g., a household object, or a sensor-enhanced counterpart thereto), devices, apparatuses, or systems (e.g., a computer system).

Several embodiments of the present disclosure are configured for capturing, acquiring, or monitoring subject performance signals while a subject engages or attempts to engage in a functional development activity sequence, a mind state exercise, and/or a body state exercise. Subject performance signals can include mind signals; body signals; and/or other types of signals such as subject speech signals, signals corresponding to sensing elements in the subject's environment, or signals corresponding to computer input device activation or selection by the subject. Subject performance signals can provide an indication of whether the subject is engaging or attempting to engage in a functional development activity sequence, mind state exercise, and/or body state exercise. Additionally or alternatively, subject performance signals can provide a measure of the subject's proficiency in performing a functional development activity sequence, mind state exercise, or body state exercise.

As indicated above, based upon captured or retrieved mind signals and body signals, embodiments of the present disclosure generate mind state indicators and body state indicators. Based upon such indicators, embodiments of the disclosure can estimate or determine whether a subject's current mind state and body state are or are expected to be conducive to or synergistic with increasing or maximizing a likelihood of successful functional development activity sequence performance and/or associated learning, neuroplasticity, or neural reorganization that can result in accelerated, enhanced, and/or sustained functional development or improvement.

Embodiments of the present disclosure provide particular types of biofeedback to the subject that can indicate or convey an extent to which the subject's current mind state(s) and body state(s) are suitable for, conducive to, or cooperatively coordinated or synergistically aligned with the subject's visualization, attempted performance, or performance of functional development activity sequences, and/or activity relevant learning or neural reorganization. Biofeedback provided in accordance with several embodiments of the disclosure can indicate whether the subject's current mind state and body state are aligned in a manner that is correlated with reference or target mind state parameters and body state parameters, respectively, which correspond or are expected to correspond to a set of developmental or therapeutic objectives that include one or more of successful activity sequence performance, accelerated or enhanced functional development, learning, and favorable neural reorganization.

Biofeedback provided in accordance with multiple embodiments of the present disclosure includes the presentation or delivery of visual, auditory, and/or kinesthetic, proprioceptive, or haptic signals to the subject in a manner that can make the subject aware of their current mind and body states, and/or which can make the subject aware of an extent to which their current mind and body states are aligned or non-aligned relative to reference or target mind state parameters and reference or target body state parameters, respectively, and/or developmental or therapeutic objectives. Based upon or in response to such biofeedback, the subject can intentionally or volitionally regulate, adapt, or learn to adapt or adjust their mind state and/or body state in a manner that shifts their respective mind and/or body state toward or into (re)alignment relative to the target mind state parameters and target body state parameters, thereby enhancing a likelihood of achieving or realizing developmental or therapeutic objectives under consideration at any given time. Thus, the subject can dynamically adjust or self-correct their mind state(s) and/or body state(s) in response to biofeedback provided by embodiments of the present disclosure.

Additionally or alternatively, biofeedback provided in accordance with some embodiments of the disclosure can include the delivery or application of signals or stimuli to the subject which are intended to automatically facilitate the (re)alignment of a subject's mind state and/or body state relative to respective target mind state parameters and/or target body state parameters. Such signals can be directed to portions of one or more subject sensory systems, and can include, for instance, audio signals, visual signals, and/or kinesthetic, proprioceptive, or haptic signals that can increase a likelihood of automatically modifying or establishing a particular mind or body state, for instance, by way of a biological entrainment process.

In the event that the subject's current mind state(s) and body state(s) are or appear to be conducive to or synergistic with successful functional development activity sequence performance, learning, or neural reorganization associated therewith, embodiments of the present disclosure can adaptively adjust one or more functional development activity sequence parameters during the subject's performance, attempted performance, or assisted performance of a functional development activity sequence in order to facilitate, reinforce, and/or accelerate the subject's functional development. If the subject's current mind state and/or body state(s) are or appear to be a hindrance to or non-synergistic with successful functional development activity sequence performance or associated neural reorganization, embodiments of the disclosure can adaptively (a) adjust functional development activity sequence parameters in a manner that increases a likelihood of successful functional development activity sequence performance and related favorable neural reorganization; and/or (b) transition to a mind state or body state regulation, relaxation, training, or exercise mode directed to respectively (re)aligning the subject's current mind state or body state relative to reference or target mind state parameters or reference or target body state parameters. Such (re)alignment of the subject's mind state or body state can respectively (re)establish a mind state or body state that is expected to be conducive to or synergistic with activity sequence performance, functional development, or desirable neural reorganization.

Some embodiments of the present disclosure are further configured to selectively generate adjunct device control signals, and output such signals to one or more types of adjunct activity promotion devices that can facilitate or assist a subject's performance of functional development activity sequences. Adjunct activity promotion devices can include, for instance, a functional electrical stimulation (FES) device and/or a robotic orthosis, as further described below. Certain embodiments are additionally or alternatively configured to monitor or record a subject's mind signals and body signals by way of a portable or wearable adjunct monitoring device during one or more time intervals in which a subject is engaged in normal daily activities (e.g., activities of daily living (ADL), or a sport or game related activity), and provide real time, near-real time, or delayed feedback to the subject, a therapist, or an instructor that indicates an extent to which the subject's mind state and body state are, were, or remained conducive to daily activity performance, functional development, learning, or neural reorganization during such time intervals.

Various embodiments of the present disclosure facilitate the synergistic coordination, management, or regulation of a subject's neurocognitive state, neuroaffective state, and body or physiological state with the subject's attention, intention, will, and efforts directed to developing or (re)learning one or more functional abilities while the subject engages in a functional development activity sequence. Such synergistic unification of a subject's mind state, body state, attention, intention, volition, and efforts can enhance the subject's potential to experience one or more of cognitive learning, affective learning, and physical learning corresponding to a desirable or intended type of subject functional development or neural reorganization.

Embodiments of the present disclosure can significantly or dramatically increase the rate and/or categorical scope of subject functional development or learning, and correspondingly increase subject motivation and reduce subject frustration, thereby facilitating or driving enhanced functional performance gains over time. Correspondingly, embodiments of the disclosure may reinforce neural reward mechanisms within the subject, which can further enhance subject motivation, functional development, learning, and/or desirable neural reorganization.

Embodiments of the present disclosure can facilitate or effectuate the enhanced rehabilitation or development of abilities in subjects experiencing various types of acute or chronic functional shortcomings, inadequacies, impairment, or dysregulation, which can arise in association with motor, sensory, or sensorimotor dysfunction; psychological, mental, or cognitive dysfunction; and/or psychiatric, affective, or emotional dysfunction. As non-limiting representative examples, particular embodiments of the disclosure can enhance subject rehabilitation or functional development in a manner that alleviates, at least moderately overcomes, compensates for, or substantially, essentially, or completely overcomes one or more types of symptoms or dysfunction associated with stroke or traumatic brain injury (e.g., loss of motor control, such as fine hand function control; Broca's or expressive aphasia; Wernicke's or receptive aphasia; and/or depression following neurologic damage); learning, developmental, or behavioral disorders (e.g., dyslexia, Attention Deficit Hyperactivity Disorder (ADHD), Autism Spectrum Disorder (ASD), or Down syndrome); speech disorders (e.g., stuttering) or language disorders; cognitive impairment (e.g., associated with neurodegenerative disorders such as dementia); affective disorders (e.g., Major Depressive Disorder (MDD)); anxiety disorders (e.g., Post Traumatic Stress Disorder (PTSD) or a phobia); addiction or dependency disorders (e.g., an addiction to a substance or activity); personality disorders (e.g., borderline personality disorder); and/or other conditions. Embodiments of the present disclosure can additionally or alternatively facilitate or effectuate enhanced skills development, learning, and associated neural reorganization in normal, healthy, or unimpaired subjects.

Representative embodiments of the disclosure for addressing one or more of the foregoing problems associated with conventional assistive systems and techniques for rehabilitation or functional development are described hereafter with reference to FIGS. 1 to 15. In the description that follows, like, analogous, or generally analogous reference numerals indicate like, analogous, or generally analogous elements or process portions. Additionally, the recitation of a given reference numeral shown in a particular FIG. can indicate the simultaneous consideration of another FIG. in which the reference numeral or an analogue or counterpart thereto is shown. Furthermore, the use of "/" herein is understood to mean "and/or" unless otherwise indicated.

As used herein, the term "subject" can refer to essentially any individual or system user (e.g., a human or a primate) that can benefit from enhanced functional development. For instance, a subject can be a current or former patient of a medical professional authorized to provide care or guidance relative to a type of subject condition, disorder, or functional deficit (e.g., a neurologist or a therapist). Alternatively, a subject can be a healthy or functionally unimpaired individual. A subject can interact with systems, devices, or processes in accordance with embodiments of the present disclosure in order to facilitate or enhance their development of one or more physical, cognitive, and/or emotional capabilities.

In the description herein, the phrase "functional development" can encompass one or more of a subject's rehabilitation; development of new skills or capabilities; enhancement of existing skills or capabilities; and maintenance of existing skills or capabilities. Correspondingly, the phrase "functional development activity sequence" can encompass audio and/or visual information that is presentable to the subject and which is intended to facilitate or effectuate one or more of the subject's rehabilitation; development of new skills or capabilities; enhancement of existing skills or capabilities; and maintenance of existing skills or capabilities.

In the present disclosure, the term "set" corresponds to or is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in *An Introduction to Mathematical Reasoning Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a signal, a function or functional process, or a value depending upon the type of set under consideration.

Architectural Overview

Figure 2A:
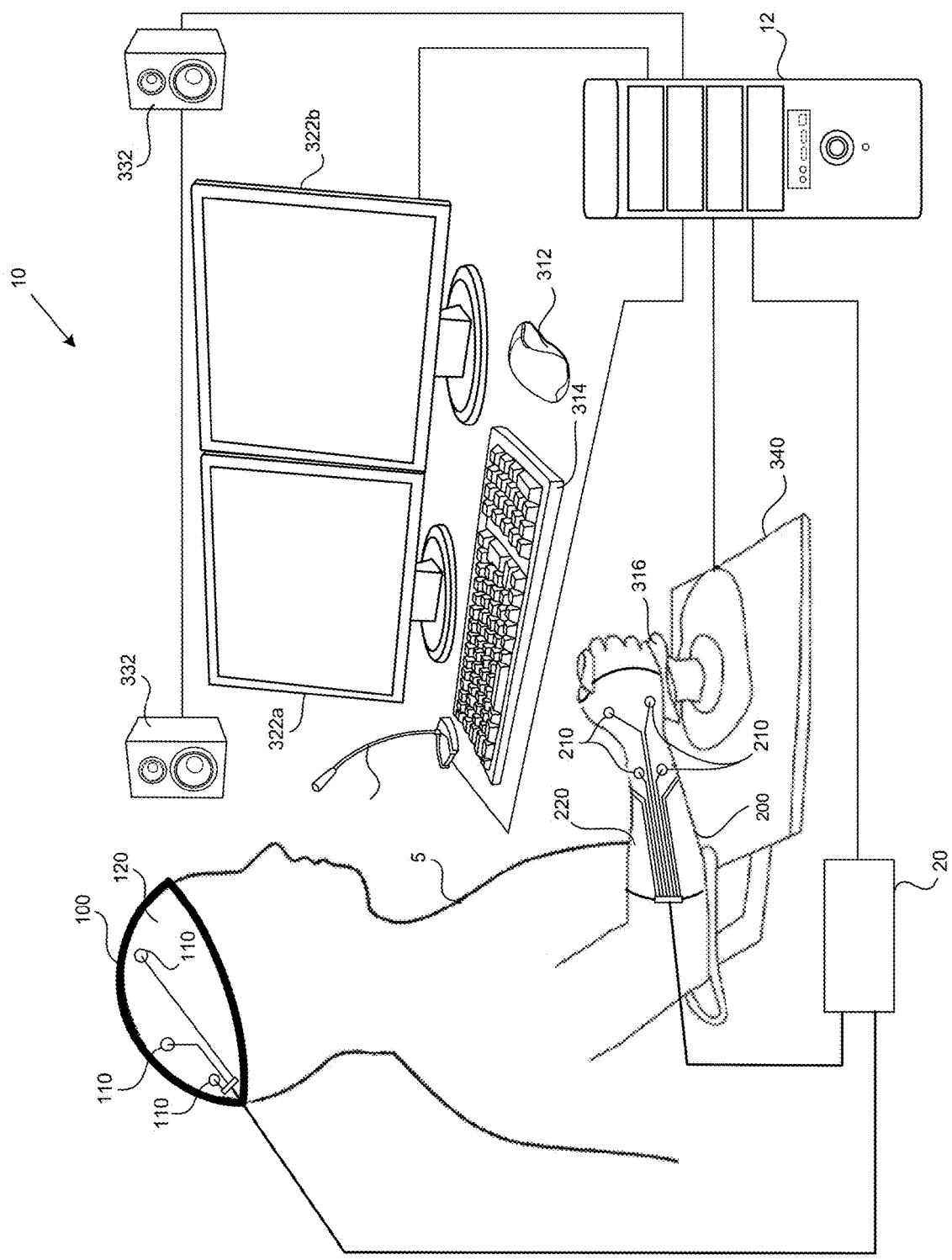
Figure 2C:
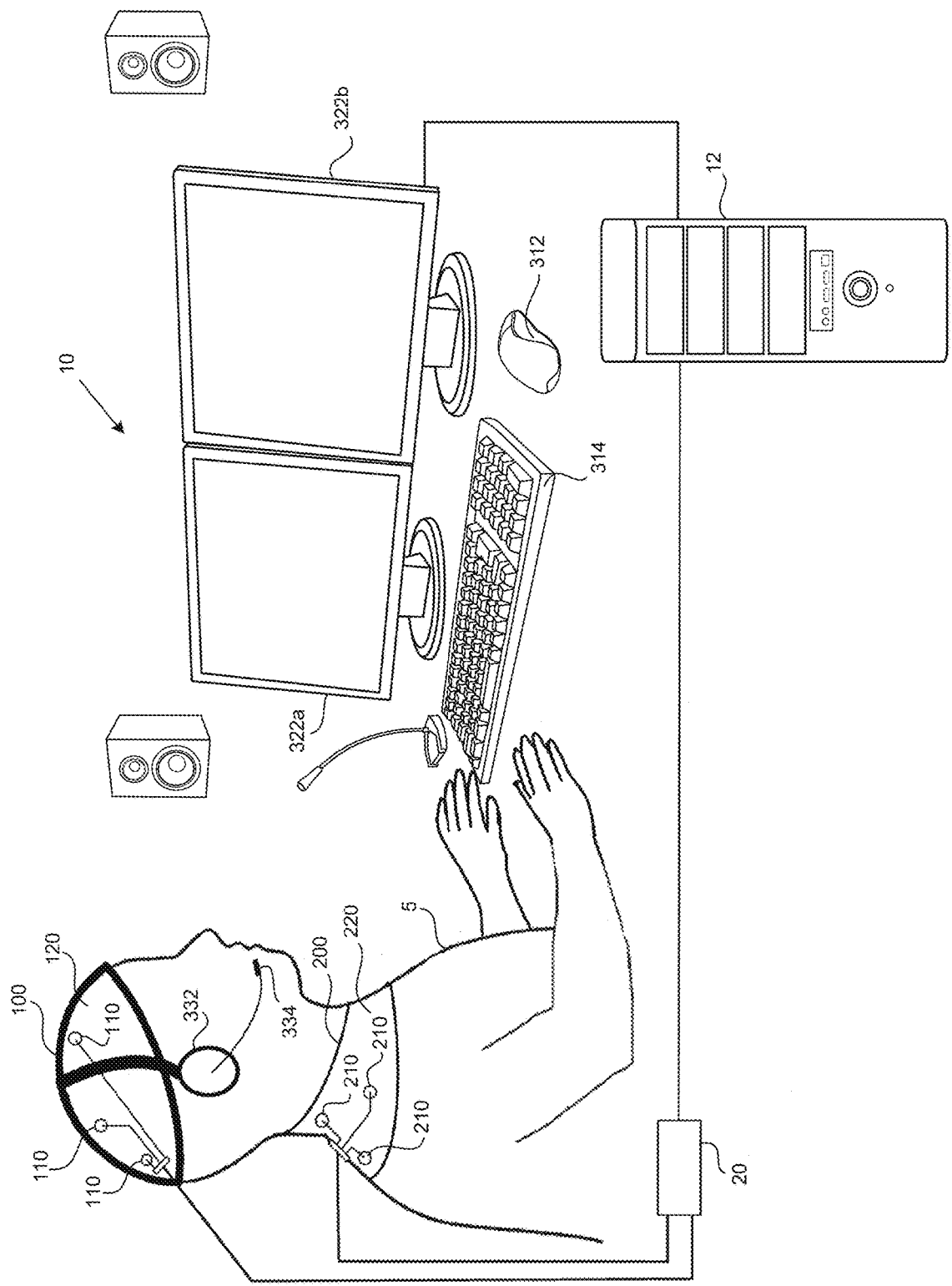

FIG. 1 is a block diagram of a system or platform 10 for unified and/or synergistic neurological-physiological rehabilitation and/or functional development according to particular embodiments of the disclosure. FIGS. 2A-2C are schematic illustrations of subjects 5 interacting with representative embodiments of systems 10 configured to facilitate particular types of neurological-physiological rehabilitation and/or functional development in accordance with the present disclosure. More particularly, FIG. 2A is a schematic illustration of a subject 5 interacting with a representative embodiment of a system 10 configured to facilitate the rehabilitation or development of upper extremity motor function, such as hand, wrist, and/or forearm control; and FIG. 2B depicts a representative implementation of the system 10 of FIG. 2A. FIG. 2C is a schematic illustration of a subject 5 interacting with a representative embodiment of a system 10 configured to facilitate the rehabilitation or development of one or more types of cognitive and/or emotional functions. Various aspects of systems 10 shown in FIGS. 2A-2C are further described in detail below.

Referring again to FIG. 1, in an embodiment a system 10 includes a signal acquisition unit 20 coupled to a set of mind signal capture apparatuses or devices 100 and a set of body signal capture apparatuses or devices 200; at least one processing unit 30; one or more data storage units 40, upon or within which a set of local databases 42 can reside; and a subject interaction unit 300 configured to (a) receive particular types of subject input and/or detect particular types of subject actions or behaviours, and (b) present or provide one or more types of feedback (e.g., biofeedback) to the subject. The system 10 further includes a memory 700 in which program instructions and/or data that facilitate or enable unified neurological-physiological rehabilitation and/or functional development processes in accordance with particular embodiments of the disclosure, as further described in detail below.

The system 10 can additionally include a set of adjunct apparatus and/or remote system interfaces 50 that facilitates wire based and/or wireless communication with adjunct activity promotion systems, subsystems, apparatuses, or devices 500; adjunct subject monitoring systems, subsystems, apparatuses, or devices 600; and/or remote systems, apparatuses, or devices such as unified neurological-physiological rehabilitation and/or functional development systems 10, remote instructor or therapist systems 80, remote activity sequence servers or databases 82, and/or other types of external or remote systems or devices 84 (e.g., a mobile telephone, a tablet computer, or an electronic game appliance). Communication with such adjunct or remote systems or devices can occur by way of a networked computing infrastructure 90, which can include one or more of a local area network (LAN), a wide area network (WAN), the Internet, and/or a mobile telephone network.

The system 10 detects, captures, acquires, or monitors mind signals and body signals from a subject by way of the set of mind signal capture apparatuses or devices 100, the set of body signal capture apparatuses or devices 200, and the signal acquisition unit 20. In various embodiments, the signal acquisition unit 20 includes hardware (e.g., analog to digital (A/D) converters, signal and/or data storage elements, and a possibly a controller or control unit), and any associated software (e.g., firmware) configured to sample mind signals and body signals. The signal acquisition unit 20 can further include hardware and/or software configured to perform particular signal filtering or signal conditioning operations upon captured signals.

The set of mind signal capture apparatuses or devices 100 includes a number of apparatuses, devices, elements, or structures configured to detect, capture, acquire, or monitor mind signals, and the set of body signal capture apparatuses or devices 200 includes a number of apparatuses, devices, elements, or structures configured to detect, capture, acquire, or monitor body signals. In various embodiments, the set of mind signal capture apparatuses or devices 100 includes a number of electrodes configured to detect electroencephalographic (EEG) signals generated by neural populations within the subject's brain (e.g., cortical neural populations), and the set of body signal capture apparatuses or devices 200 includes a number of electrodes configured to detect electromyographic (EMG) signals arising from extra-cranial neural activity (e.g., neuromuscular activity). Particular embodiments configured to capture EEG and EMG signals can be implemented by way of technologically simple, readily available, inexpensive components, as further described below.

Captured EEG signals can correspond to neural populations that are relevant to the generation or determination of mind state indicators. Additionally, captured EEG signals can correspond to neural populations that are relevant to the detection, generation, or determination of certain types of subject performance signals (e.g., in a manner that depends upon a type of functional development activity sequence under consideration). Captured EMG signals can correspond to neuromuscular pathways that are relevant to the generation or determination of body state indicators, and in several embodiments, captured EMG signals can correspond to neuromuscular pathways that are relevant to the detection, generation, or determination of subject performance signals.

Depending upon embodiment details, the set of mind signal capture apparatuses or devices 100 and/or the set of body signal capture apparatuses or devices 200 can be configured to detect, capture, acquire, or monitor additional or other types of signals. For instance, in certain embodiments, the set of mind signal capture apparatuses or devices 100 can be configured to capture magnetoencephalographic (MEG) signals, intracranial near infrared (NIR) signals, and/or functional imaging (e.g., functional Magnetic Resonance Imaging (fMRI)) signals. In particular embodiments, the set of mind signal capture apparatuses or devices 100 and/or the set of body signal capture devices 200 can be configured to capture other types of signals that can be correlated or associated with or indicative of the subject's mind state and/or body state, such as heart rate, blood oxygenation, blood pressure signals, or skin conductance signals. In any given embodiment, the set of mind signal capture apparatuses or devices 100 and the set of body signal capture apparatuses or devices 200 include hardware and/or software suitable for capturing, acquiring, or sampling a given type of mind signal or body signal under consideration, respectively.

The processing unit 30 includes one or more instruction processing devices (e.g., at least one microprocessor and/or microcontroller) capable of executing stored program instructions. Additionally or alternatively, the processing unit 30 can include one or more state machines. The data storage unit 40 includes one or more types of fixed and/or removable data storage devices or elements, as well as storage media corresponding thereto. For instance, the data storage unit 40 can include a hard disk drive, a DVD or CD-ROM drive, an SD card, and/or a USB flash drive. The memory 700 includes one or more types of volatile and/or nonvolatile memory, such as a register set, one or more buffers, Random Access Memory (RAM), and Read Only Memory (ROM) configured to store program instructions and data.

Portions of the data storage unit 40 and/or the memory 700 can form one or more computer programmable or readable media upon or within which software modules reside that include program instruction sets directed to performing particular unified neurological-physiological rehabilitation and/or functional development operations in accordance with embodiments of the disclosure. In general, portions of such software modules when executed can facilitate or enable one or more of (a) the acquisition, retrieval, processing, and/or analysis of a subject's mind signals and body signals; (b) the subject based or subject specific calibration of certain system parameters, which can include reference mind state parameters and reference body state parameters; (c) the estimation, determination, and/or analysis of the subject's current and/or past mind state(s) and body state(s), such as by way of the generation of mind state indicators and body state indicators; (d) the acquisition, retrieval, processing, and/or analysis of subject performance signals; (e) the generation of certain types of functional activity cues; (f) the generation of adjunct activity promotion device control signals; (g) the adaptive management of functional development activity sequence presentation to the subject based upon the subject's mind state, body state, and/or activity performance results; (h) the selective provision of mind state exercises and body state exercises to the subject; (i) the provision of biofeedback to the subject; and (j) the transfer of signals or data to or from external or remote systems or devices in accordance with embodiments of the disclosure.

In various embodiments, the memory 700 includes an operating system 702 and possibly application environment software 704. The application environment software 704 can provide a graphical programming environment and associated resources, database(s), tools, and/or toolkits directed to the development, testing, simulation, and/or operation of measurement, test, or control systems (e.g., an embedded system configured to perform particular unified neurological-physiological rehabilitation and/or functional development operations according to an embodiment of the disclosure). In a representative implementation, the application environment software 704 includes LabVIEW (National Instruments Corporation, Austin, Tex., USA).

The memory 700 additionally includes a system management module 720 that is configured to manage, coordinate, direct, and/or control aspects of unified neurological-physiological rehabilitation and/or functional development operations in accordance with embodiments of the disclosure. In various embodiments, the system management module 720 includes a calibration module 730, a state analysis module 740, a biofeedback module 750, a mind state exercise module 760, a body state exercise module 762, and a mind-body adaptive activity module 770. The calibration module 730 can include a mind state calibration module 732 and a body state calibration module 734; and the state analysis module 740 can include a mind state analysis module 742 and a body state analysis module 744.

In several embodiments, the system management module 720 also includes at least one of a cue generation module 780, an adjunct signal generation module 782, and a subject performance module 790. The cue generation module 780 can manage the generation of visual, auditory, and/or kinesthetic stimuli that can guide or time particular types of subject actions or behaviors during the subject's visualization, attempted performance, or performance of a functional development activity sequence, mind state exercise, and/or body state exercise. The adjunct signal generation module 782 can manage the generation of adjunct apparatus or device control signals directed to one or more adjunct activity promotion devices 500 that facilitate the subject's performance of functional development activity sequences.

The subject performance module 790 can manage the acquisition, retrieval, generation, storage, and/or analysis of subject performance signals. In general, subject performance signals correspond to one or both of (a) an indication of whether the subject is engaging or attempting to engage in a functional development activity sequence, a mind state exercise, and/or body state exercise; and (b) a level of subject proficiency (e.g., a proficiency metric) associated with the subject's attempted performance or performance of a functional development activity sequence, mind state exercise, and/or body state exercise. Depending upon embodiment details, subject performance signals can be based upon subject input, captured mind signals, captured body signals, and/or other types of signals (e.g., a sensed subject behavior or action, such as subject body part motion).

Particular operations supported or performed by the system management module 720 are further described in detail below. In a representative implementation, portions of the system management module 720 can be associated with, based upon, or interfaced with graphical blocks corresponding to the application environment software 704.

The memory 700 includes a signal and parameter memory 710 in which mind signals, body signals, and subject performance signals can reside, as well as processed versions of such signals. Certain system parameters (e.g., subject based or subject specific system operation or calibration parameters) can also reside within the signal and parameter memory 710. The memory 700 also includes a signal processing module 706 configured to process or analyze mind signals, body signals, and possibly subject performance signals. In various embodiments, the signal processing module 706 is configured to selectively or programmably perform time domain, frequency domain, and/or spatial domain operations upon mind signals and body signals, as further detailed below. Depending upon embodiment details, one or more portions of the signal processing module 706 can be provided by the application environment software 704.

The memory 700 additionally includes a subject state memory 712 in which a set of mind state indicators and a set of body state indicators can reside, and a possibly reference state memory 714 in which a set of reference or target mind state parameters and/or a set of reference or target body state parameters can reside. Mind state indicators, reference mind state parameters, body state indicators, and/or reference body state parameters can additionally be stored upon a local and/or a remote database 42, 82. Mind state indicators can represent aspects of a subject's mental state at particular times (e.g., on a real time, near-real time, or periodic basis), and body state indicators can correspondingly represent aspects of the subject's body state at particular times. Reference mind state parameters and reference body state parameters can respectively correspond to or represent one or more mind states and one or more body states that are expected to synergistically enhance functional development activity sequence performance, learning, and favorable, beneficial, or therapeutic neural reorganization. Representative types of mind state indicators, reference mind state parameters, body state indicators, and reference body state parameters are described in detail below.

The memory 700 further includes an activity memory 716 in which portions of one or more audio and/or visual functional development activity sequences, mind state exercises, and/or body state exercises can reside. Particular functional development activity sequences, mind state exercises, or body state exercises can additionally reside upon a local database 42 and/or a remote database 82. As further described in detail below, the system management module 720 can selectively and adaptively direct the presentation of functional development activity sequences, mind state exercises, and/or body state exercises to the subject based upon or in response to subject input, the values of particular subject mind state indicators, the values of particular subject body state indicators, and/or the values of particular subject performance signals.

Functional development activity sequences, mind state exercises, body state exercises, and biofeedback are presented or communicated to the subject by way of the subject interaction unit 300, which is configured to provide a set of user interfaces by which the subject a) can progressively or dynamically interact with the system 10 and engage or attempt to engage in rehabilitative or functional development activity sequences, mind state exercises, or body state exercises; and b) is provided with biofeedback. In various embodiments the subject interaction unit 300 includes a set of input devices 310, a visual interface 320, an audio or auditory interface 330, and a kinesthetic interface 340.

The set of input devices 310 can include one or more wireless and/or wire-based devices configured to detect, sense, receive, or capture signals from (a) subject manipulable, movable, or actuatable apparatuses or devices; and/or (b) sensing devices or elements within the subject's environment. For instance, the set of input devices 310 can include a text entry device (e.g., a computer keyboard); a pointing device (e.g., a computer mouse or trackball); a joystick; a proximity, presence, touch, or pressure sensitive device (e.g., a touchpad or drawing tablet, or a set of motion sensors); a game controller; an optical signal or image capture or sensing device (e.g., a camera); an action or gesture sensing or responsive device (e.g., a gesture responsive game controller); and/or other type of device (e.g., a music-enabled device such as a musical keyboard). Depending upon embodiment details, particular input devices 310 can be associated with or form portions of one or more user interfaces 320, 330, 340.

The visual interface 320 can include one or more display devices, such as a computer monitor (e.g., a flat panel display) configured to present or output visual or optical signals. The visual interface 320 can also include or be coupled to a graphics processor configured to render video, animations, images, graphics, symbols, and/or text upon such electronic display devices. In multiple embodiments, the visual interface 320 provides a graphical user interface (GUI) configured to present visual content, information, or signals corresponding to functional development activity sequences, mind state exercises, body state exercises, and biofeedback to the subject, as further detailed below.

The audio interface 330 can include one or more audio signal output devices, such as a set of headphones or a set of speakers; and associated audio signal hardware and/or software (e.g., firmware). The audio interface 330 can present audio content, information, or signals corresponding to one or more of functional development activity sequences, mind state exercises, body state exercises, and biofeedback to the subject. The audio interface 330 can additionally include a set of audio signal input devices, such as a microphone.

The kinesthetic interface 340 can include one or more apparatuses or devices configured to provide, deliver, or apply kinesthetic, proprioceptive, and/or haptic signals to the subject, where such signals can include motion or force related signals, vibratory signals, and/or tactile signals. Kinesthetic signals can be provided to particular portions of the subject's body by way of a kinesthetic apparatus or device that includes one or more transducers and/or actuators configured to generate or output such signals. In representative embodiments, a kinesthetic device can include a computer keyboard, a mouse, a joystick, a game controller, a rumble pad, a musical keyboard, or other type of input device 310 that carries a set of such transducers or actuators. The kinesthetic interface 340 can apply kinesthetic signals to the subject, which can correspond to functional development activity sequences, mind state exercises, body state exercises, and/or biofeedback.

A system 10 in accordance with an embodiment of the disclosure additionally includes a number of signal transfer or data communication interfaces. For instance, each of the signal acquisition unit 20, the adjunct apparatus/remote system interface 50, and the activity interface unit 300 can include or be coupled to one or more signal transfer interfaces that facilitate or enable the transfer of signals or data to and/or from the memory 700 to support unified neurological-physiological rehabilitation and/or functional development operations in accordance with embodiments of the disclosure. Such signal transfer interfaces can include one or more of a serial port, a USB port, an Ethernet interface configured to operate in accordance with a standard network information transfer protocol (e.g., TCP/IP), and/or another type of interface. A system 10 can further include a set of common buses or communication pathways 15 by which local and/or remote signal transfer or exchange between system elements can occur.

Aspects of Representative Reference Mind State Parameters and Body State Parameters In various embodiments, the system 10 captures or acquires mind signals and body signals from a subject in association with portions of a system calibration process, (which occurs prior to or outside of the subject's engagement in functional development activities), and respectively generates reference mind state parameters and reference body state parameters therefrom. Reference mind state parameters correspond to mind state indicator levels or intensities (e.g., minimum or threshold levels or intensities) against which mind state indicators generated while the subject engages in functional development activity sequences or mind state exercises can be compared, measured, referenced, or graded to facilitate the estimation or determination of aspects of the subject's current mind state. Reference body state parameters correspond to body state indicator levels or intensities (e.g., minimum or threshold levels or intensities) against which body state indicators generated while the subject engages in functional development activity sequences or body state exercises can be compared, measured, referenced, or graded to facilitate the estimation or determination of aspects of the subject's current body state.

In a representative embodiment, during a first portion of a calibration process the system 10 presents the subject with a relaxation sequence or routine (e.g., which can include audio and/or visual signals) that can guide the subject toward or to a relaxed, at-rest, or baseline mind state. That is, the relaxation sequence can facilitate the subject's establishment of a relaxed, at-rest, or baseline mental state. At particular time intervals or points during the relaxation sequence, the system 10 captures mind signals, which can be referred to as at-rest mind signals. The system 10 generates or calculates a set of at-rest mind state indicators under consideration using the at-rest mind signals, and generates, determines, or defines a set of reference mind state parameters therefrom. In some embodiments, a particular reference mind state parameter can be generated using a predetermined, programmable, or selectable multiplier applied to a corresponding at-rest mind state indicator, for instance, a multiplier of approximately 120%-180% (e.g., about 150%), such that the reference mind state parameter has a level or intensity that exceeds the corresponding at-rest mind indicator by approximately 20%-80% (e.g., about 50%). In a representative embodiment, a set of reference mind state parameters can include one or more EEG signal amplitude threshold parameters, one or more EEG signal frequency ratio threshold parameters, and/or one or more EEG signal power component threshold parameters.

During the course of the subject's engagement in functional development activity sequences, the subject is presented with biofeedback that can convey whether the level or intensity of a given mind state indicator exceeds, approximately equals, or is less than a corresponding reference mind state parameter, thereby conveying an extent to which the subject's mind state when actively engaged in functional development activity sequences is shifted toward, into, or away from the at-rest mind state and/or a mental state that is expected to be conducive to functional development, learning, and/or beneficial neural reorganization. Similarly, during the course of the subject's engagement in mind state exercises, the subject is presented with biofeedback that can convey whether the subjects mind state is shifted toward, into, or away from the at-rest mind state and/or a mental state that is expected to be conducive to functional development, learning, and/or beneficial neural reorganization.

In a representative embodiment, during a second portion of a calibration process the system 10 directs the subject (e.g., by way of audio and/or visual signals) to attempt to maximally move or activate one or more body parts in predetermined manners (e.g., corresponding to extension or flexion), while the system concurrently captures body signals (e.g., EMG signals) corresponding to such body parts (e.g., muscles associated with the movement of a given type of body part, such as a finger, hand, or wrist). The system 10 generates a set of maximal volitional contraction (MVC)

body state indicators from such body signals, and correspondingly generates, determines, or estimates a set of reference MVC body state parameters therefrom, such as a set of muscle contraction threshold parameters. An MVC body state indicator can correspond to or be a maximum or largest body signal level (e.g., an EMG signal level) that the subject can generate during a volitional contraction of a particular muscle under consideration; and an associated muscle contraction threshold parameter can correspond to or be a threshold or minimum body signal level (e.g., an EMG signal level) that the system 10 can utilize to recognize or count a muscle contraction as significant, successful, or relevant with respect to an activity or task under consideration. In several embodiments, an MVC body state indicator can be generated as an average generated from multiple captured body signals, such as multiple subject contractions or attempted contractions of the muscle under consideration.

A reference MVC body state parameter such as a muscle contraction threshold parameter (e.g., a muscle contraction amplitude threshold parameter) can be generated using a predetermined, programmable, or selectable multiplier applied to an appropriate MVC body state indicator, for instance, a multiplier of approximately 20%-80% (e.g., about 50%), such that the muscle contraction threshold parameter has a level or intensity that is a desired fraction of the corresponding MVC body state indicator, for instance, 20%-80% (e.g., about 50%) of the MVC body state indicator. For instance, a muscle contraction threshold parameter that is generated as approximately 20% of an MVC body state indicator can represent an EMG measure (e.g., an EMG amplitude measure of muscle contraction) that is at least approximately 20% of an EMG measure of the subject's maximum volitional contraction of a muscle under consideration. Such a muscle contraction threshold parameter can represent a threshold or minimum EMG signal level for categorizing the subject's contraction or attempted contraction of a given muscle as significant, successful, or relevant, as further described below. MVC body state indicators and muscle contraction threshold parameters can differ from one muscle to another, and/or one subject to another.

During the course of the subject's engagement in functional development activity sequences or body state exercises, the subject is presented with biofeedback that can convey the level or intensity of a given body state indicator relative or in relation to an associated or correlated reference body state parameter. Such biofeedback can convey an extent to which subject activation of a particular muscle compares to a desired fraction of a maximum volitional muscle activation level or intensity.

Aspects of Representative Subject Performance Signals

In general, the nature or type(s) of subject performance signals acquired or generated depends upon a type of task corresponding to a functional development activity sequence, mind state exercise, or body state exercise under consideration at any given time. In embodiments in which a task or activity is directed to bodily movement, subject performance signals include body performance signals indicative of the subject's movement or attempted movement of a body part under consideration. Such signals can include EMG based signals and/or other types of signals indicative of movement, for instance, signals generated by accelerometers worn by the subject or signals generated by motion sensors in the subject's environment.

In a representative embodiment, one type of body performance signal is a relevant volitional contraction (RVC) signal, which can be defined as (a) a set of current EMG measures or signal levels corresponding to the subject's current or most recent contraction or attempted contraction of a particular muscle involved in a type of movement under consideration, minus (b) a muscle contraction threshold parameter corresponding to this muscle, where the muscle contraction threshold parameter represents a threshold or minimum EMG measure or signal level that should be attained or exceeded in order for the subject's contraction or attempted contraction of this muscle to be considered significant, meaningful, successful, or relevant. When an RVC signal corresponding to a particular muscle has a value that is greater than or equal to zero, a current or most recent contraction or attempted contraction of the muscle can be categorized or defined as a relevant or successful muscle contraction. Similarly, when an RVC signal corresponding to the muscle has a value that is less than zero, the current or most recent contraction or attempted contraction of the muscle can be categorized as insignificant, non-meaningful, unsuccessful, or non-relevant.

In embodiments in which a task is directed to mental (e.g., cognitive or emotional) activity, subject performance signals can include mind performance signals, which can be EEG based signals corresponding to brain areas associated with task performance. In a representative embodiment, such EEG based signals can correspond to a portion of the prefrontal cortex (e.g., the left and/or right dorsolateral prefrontal cortex (DLPFC)), the parietal cortex, the superior temporal gyrus, or another brain area.

Subject performance signals can also include one or more types of subject performance metrics, such as a number of times a condition was satisfied or a task was successfully performed during a given time period, and/or a rate at which the subject attempted or performed a task. In embodiments directed to bodily movement, subject performance metrics can be estimated or determined by an analysis of EMG measures or signals. For instance, in a representative implementation, one type of subject performance metric is an RVC signal count (e.g., a cumulative RVC signal count) with respect to a given period of time (e.g., a current duration of a functional development activity sequence or therapy session), indicating for a muscle corresponding to the RVC signal a number of relevant or successful contractions that occurred during the time period under consideration. Any given functional development activity sequence or therapy session can be associated with a certain number of tasks or activities that the subject is to perform or attempt to perform, such that for any given muscle under consideration an ideal or perfect RVC signal count (e.g., a muscle activation score of 100% relevant volitional contractions) for the functional development activity sequence or therapy session can be estimated, determined, or known.

Subject performance metrics can also be generated by way of the reception and analysis of other types of signals that are correlated with subject movement, such as particular types of subject input and/or sensed signals within the subject's external environment. In certain embodiments, subject performance metrics can be based upon subject input received by way of one or more input devices 310 (e.g., a keyboard, a mouse, a joystick, or a game controller) or kinesthetic devices 340 configured for subject input, sensing, or feedback, the system management module 720 can acquire or generate subject performance signals corresponding to a level of proficiency associated with the subject's performance or attempted performance of a functional development activity sequence, mind state exercise, or body state exercise under consideration. Subject manipulation of an input device 310 or kinesthetic device 340 can occur in association with the presentation of audio and/or visual information or signals to the subject by way of the audio interface 330 and the visual interface 320, respectively.

Subject performance metrics can also include a set of mind state maintenance scores and/or body state maintenance scores that respectively correspond to an analysis of captured mind state indicators and body state indicators relative to reference mind state parameters and reference body state parameters. Mind state maintenance scores and body state maintenance scores can provide an indication of whether the subject maintained their mind state and body state in a condition suitable for realizing therapeutic objectives or improved functional performance while observing, visualizing, attempting to perform, or performing a task under consideration. Subject performance metrics can additionally or alternatively include other types of signals, such as subject scores on particular types of tests or questionnaires, or subject speech signals.

In multiple embodiments, particular types of subject performance signals can be correlated with or based upon one or more mind state indicators, body state indicators, and/or mind-body synergy indices or indicators, which are further described in detail hereafter.

Aspects of Representative Mind State Indicators and Body State Indicators

A system 10 in accordance with an embodiment of the disclosure can acquire or sample (e.g., periodically or essentially continuously) particular types of mind signals and body signals. The system's mind state analysis module 742, body state analysis module 744, and/or signal processing module 706 can filter and/or process such acquired signals to generate mind state indicators and body state indicators that respectively convey or correspond to the subject's current or recent mind state(s) and body state(s). Depending upon embodiment details, an extent or type of subject functional impairment under consideration, and/or one or more types of functional development activity sequences available for subject selection (e.g., directed to alleviating or overcoming such functional impairment, maintaining a level of functional capability; or extending or developing a functional capability of an unimpaired subject), the system 10 can generate particular types of mind state indicators and body state indicators.

Mind state indicators can include raw, filtered, and/or processed signals that convey whether aspects of the subject's mental state (e.g., cognitive and/or emotional states) are conducive, expected to be conducive, sub-optimal, or expected to be sub-optimal with respect to (a) the subject's performance of a functional development activity sequence under consideration; (b) enhanced learning or favourable (e.g., therapeutic) neural reorganization; and/or (c) maintenance of functional capabilities or performance gains. In various embodiments, mind state indicators include EEG based signals that convey or measure an extent or expected extent to which the subject's mental activity corresponds to some or each of a level of stress or anxiety, a level of relaxation, and a level of mental attention or focus.

Such EEG based mind state indicators can be based up, correlated with, and/or include one or more of (a) a relative alpha measure, (e.g., alpha band power density relative to absolute band power (ABP) across delta, theta, alpha, and beta bands); (b) a beta to alpha ratio (e.g., beta band power relative to alpha band power); (c) a delta to alpha ratio (e.g., delta band power relative to alpha band power); (d) a theta to beta ratio (e.g., theta band power relative to beta band power); (e) one or more measures of interhemispheric symmetry or asymmetry, which can indicate an extent to which EEG signal magnitude or spectral content is balanced between corollary brain areas in the left and right brain hemispheres; (f) a sensorimotor, mu rhythm, coherence (e.g., cortico-cortical coherence), or other type of neural synchronization measure, which can correspond to an extent to which particular neural populations (e.g., pyramidal and/or mirror neurons) are synchronized or desynchronized; (g) a movement related cortical potential (MRCP) measure; and (h) another measure or ratio that is correlated with EEG signals (e.g., gamma band activity) acquired or retrieved from the subject.

In multiple embodiments, the system 10 can utilize particular mind signals and/or mind state indicators as primitives or operands that serve as inputs to a set of mathematical and/or logical algorithms or functions that generate or output one or more additional or other mind state indicators. In some embodiments, such additional or other mind state indicators can be referred to as combined, compound, amalgamated, or composite mind state indicators.

A representative example of a composite mind state indicator is a mind state alignment indicator $M_A$ that defines a ratio between a mean relative alpha band power measure $\overline{P_\alpha}$ and a delta-to-alpha measure DAR referenced to a particular time t, normalized to a baseline or at rest ratio between the mean relative alpha measure $\overline{P_\alpha}$ and the delta-to-alpha measure DAR. Mathematically, $M_A$ at time t can be expressed as follows:

$$M_A(t) = \{\overline{P_\alpha}/DAR\}_t / \{\overline{P_\alpha}/DAR\}_{rest} \qquad (1)$$

In various situations, as a mean relative alpha band power measure $\overline{P_\alpha}$ increases, a subject's degree, extent, or level of relaxation and/or positive affect can be expected to increase, which is expected to be conducive to the subject's functional development. Additionally, as a delta-to-alpha measure DAR decreases, a subject's degree, extent, or level of alertness can be expected to increase, which is also expected to be conducive to the subject's functional development. Thus, as the mind state alignment indicator $M_A$ increases away from a hypothetical minimum value of zero, it can be expected that the subject's mind state becomes increasingly more conducive to functional development, learning, and/or beneficial neural reorganization.

At any given time t, the value of the mind state alignment indicator $M_A$ provides a manner of estimating, determining, or indicating whether the subject's internal cognitive and/or emotional states are facilitatory with respect to functional development and/or maintenance. Furthermore, the capture, storage, and/or analysis of mind state alignment indicator $M_A$ values across time provides a manner of tracking or analyzing an extent to which the subject's cognitive and/or emotional states varied during functional development activities, mind state exercises, and/or body state exercises. The value of the mind state alignment indicator $M_A$ at a particular time t can be referred to as a mind state alignment measure.

In general, the type(s) of mind state indicator(s) (which can include composite mind state indicators) generated by the system 10 can correspond to the nature and/or extent of a subject's functional impairment, for instance, as determined or estimated by one or more standard measures or tests of functional capability; relative comparison to the functional capabilities of healthy, normal, or unimpaired individuals; and/or EEG recordings performed upon the subject. The relevance or potential relevance of particular mind state indicators with respect to achieving beneficial neuroplasticity, functional development, or functional maintenance in view of the nature and/or extent of the subject's functional impairment can be based upon one or more of clinician or therapist experience (e.g., with regard to one or more subjects' functional development or functional maintenance results), EEG recordings performed on the subject, and EEG studies involving normal and/or impaired subjects. Such EEG studies can correspond to one or more of the following references:

a) "Continuous quantitative EEG monitoring in hemispheric stroke patients using the brain symmetry index," M. J. A. M. Van Putten, D. L. J. Tavy, *Stroke* 35 (2004), 2489-2492;

b) "Quantitative EEG parameters for monitoring and biofeedback during rehabilitation after stroke," S. Kanna, J. Heng, Proceedings of *IEEE/ASME International Conference on Advanced Intelligent Mechatronics, AIM* 2009, 1689-1694;

c) "The development of a quantitative electroencephalographic scanning process for attention deficit-hyperactivity disorder: reliability and validity studies," V. J. Monastra, J. F. Lubar, M. Linden, *Neuropsychology* 15(1), 136-144 (2001);

d) "Effects of stimulant medications on the EEG of children with attention deficit-hyperactivity disorder," A. R. Clarke, R. J. Barry, D. Bond, R. McCarthy, M. Selikowitz, *Psychopharmacology* 164, 277-284 (2002); and e) "The EEG in the normal elderly: A contribution to the interpretation of ageing and dementia," S. Giaquinto, G. Nolfe, *Electroencephalography and Clinical Neurophysiology* 96, 540-546 (1986).

In representative embodiments, for subjects experiencing functional impairment as a result of neurological damage due to stroke or traumatic brain injury, mind state indicators be based upon or include one or more of a relative alpha measure, a delta to alpha ratio, and a hemispheric asymmetry measure. For subjects experiencing functional impairment associated with learning disabilities, mind state indicators can be based upon or include one or more of a frontal lobe theta to beta ratio, a frontal lobe beta to alpha ratio, and an overall alpha band power measure.

In some embodiments, associations or mappings between the type(s) and/or extent of subject functional impairment under consideration and one or more trial sets of mind state indicators can be stored in a local or remote database 42, 82. In such embodiments, the system 10 can identify, determine, or select (e.g., automatically or in response to clinician or therapist input) an initial or default set of mind state indicators from among the trial sets of mind state indicators. The system can utilize the initial set of mind state indicators to monitor or determine the subject's mind state across an initial number of functional development sessions or during an initial time period (e.g., a number of days or week) in which the subject engages functional development activity sequences. Based upon the subject's functional development or functional maintenance results, the system 10 can utilize a prior or most recent set of mind state indicators (e.g., if subject functional development results are satisfactory), or select a new, different, or next set of mind state indicators (e.g., if subject functional development results are unsatisfactory). In certain embodiments, the system 10 can test different sets of mind state indicators to identify a set of mind state indicators that presently facilitates a highest level of subject functional development or maintenance. Such a set of mind state indicators can be stored in a local or remote database 42, 82, and may be defined as subject specific mind state indicators.

Body state indicators can include raw and/or processed signals that can convey or indicate whether particular portions of the subject's body are in a state that is conducive to facilitating or hindering (a) the subject's performance of a functional development activity sequence under consideration and/or (b) learning or favourable neural reorganization.

For a functional development activity sequence that involves the subject's movement or attempted movement of one or more body parts, in various embodiments body state indicators include EMG based signals indicative of the selective activation of muscles or muscle groups that control the movement of a body part under consideration, and can include EMG based signals that measure an extent of co-contraction between opposing muscles, which would hinder or prevents successful or efficient body part movement. For a functional development activity sequence directed to the restoration or development of cognitive or emotional function, body state indicators can include EMG based signals indicative of a level of bodily stress or relaxation corresponding to one or more body parts. For instance, body state indicators can be based upon or include EMG signals corresponding to subject neck, shoulder, and/or chest muscles.

In multiple embodiments, the system 10 can utilize particular body signals and/or body state indicators as primitives or operands that serve as inputs to a set of mathematical and/or logical algorithms or functions that generate or output one or additional or other body state indicators. In particular embodiments, such additional or other body state indicators can be referred to as combined, compound, amalgamated, or composite body state indicators.

A body state alignment indicator can correspond to an extent or expected extent to which a subject's body state is conducive (or counterproductive) with respect to successful performance of a functional development activity under consideration. In a representative embodiment directed to the development or restoration of the subject's ability to perform compound, complex, or intricate movement sequences associated with one or more muscle groups, a body state alignment indicator $B_A$ can be defined as a measure of an extent or expected extent to which agonist muscle contraction(s) relevant to a movement sequence under consideration at time t are dominant or subordinate with respect to antagonist muscle contraction(s) expected to be counterproductive to the movement sequence under consideration at time t. Such an agonist-antagonist muscle contraction measure can be normalized to a baseline measure of agonist muscle contraction.

Mathematically, a body alignment indicator $B_A$ of this type can be defined as follows:

$$B_A(t) = \{VC(t)_{agonist} - VC(t)_{antagonist}\}/VC(t)_{resting\ agonist} \quad (2)$$

where $VC(t)_{agonist}$ is a current or recent EMG measure of voluntary target agonist muscle contraction at time t, relative to a muscle contraction threshold parameter corresponding to the target agonist muscle. For instance, $VC(t)_{agonist}$ can correspond to or be an EMG signal level measuring an extent of target agonist muscle contraction at time t, minus a target agonist muscle contraction threshold parameter (e.g., a multiplier of 0.2 applied to an MVC body state indicator corresponding to the target agonist muscle, which provides a baseline EMG measure of maximum voluntary target agonist muscle contraction, for instance, as determined in association with a system calibration process). Analogously, $VC(t)_{antagonist}$ can correspond to or be an EMG measure of voluntary target antagonist muscle contraction at time t, relative to a muscle contraction threshold parameter corresponding to the target antagonist muscle. For instance, $VC(t)_{antagonist}$ can be an EMG signal level measuring an extent of target antagonist muscle contraction at time t, minus a target antagonist muscle contraction threshold parameter (e.g., a multiplier of 0.2 times an MVC body state indicator corresponding to the target antagonist muscle, which provides a baseline EMG measure of maximum voluntary target antagonist muscle contraction).

$B_A(t)$ will have a value that tends towards or equals approximately zero if co-contraction of target agonist-antagonist muscles is severe, which corresponds to body state that is counterproductive with respect to a type of functional development activity sequence under consideration. $B_A(t)$ will have a value that tends toward or approximately equals 1, indicating a body state that is conducive to the functional development activity sequence under consideration, if a target antagonist muscle is well relaxed, particularly in the event that the $VC(t)_{antagonist}$ approximately equals its corresponding target antagonist muscle threshold contraction parameter. The value of $B_A$ at a particular time t can be referred to as a body state alignment measure.

Target agonist and antagonist muscles can include or be the dominant extensor and flexor muscles for a particular type of action or motion that is relevant in the context of a functional development activity sequence under consideration. For instance, in a representative implementation directed to developing or restoring wrist extension capability, the extensor carpi ulnaris can be the target agonist muscle, and the flexor carpi ulnaris can be the target antagonist muscle.

Aspects of Representative Mind—Body Synergy Indices, Indicators, or Measures

In several embodiments, the system 10 can further transform or operate upon raw and/or processed mind signals and body signals, including one or more mind state indicators or body state indicators described above, to generate a set of mind-body synergy indices, indicators, or measures. A mind-body synergy index, indicator, or measure can provide an estimation or indication of whether the subject's mind state(s) and body state(s) are cooperatively coordinated, aligned, attuned, unified, or harmonized in a manner that is expected to be correlated with or result in substantial, rapid, sudden, nonlinear, surprising, spontaneous, and/or lasting gains in the subject's functional performance or development. Thus, a mind-body synergy index, indicator, or measure can correspond to an extent or an expected extent to which the subject's mind state and body state synergistically reinforce or complement each other as well as the subject's performance, attempted performance, visualized performance, or observed performance of a functional development activity sequence under consideration, and learning or favourable neural reorganization associated therewith. A mind-body synergy index, indicator, or measure can convey an extent or expected extent to which the subject is operating in or maintaining a peak performance and/or optimized learning state.

In particular embodiments, the system 10 can utilize particular mind state indicators and particular body state indicators as primitives or operands that serve as inputs to a set of mathematical and/or logical algorithms or functions that generate or output one or more mind-body synergy indices, indicators, or measures. In a representative embodiment, a set of mind-body synergy indices, indicators, or measures includes a Breakthrough Index (BTI) or measure, which corresponds or is expected to correspond to a likelihood that the subject's mind state and body state can synergistically facilitate or drive substantial, accelerated, sudden, nonlinear, surprising, spontaneous, and/or lasting gains in functional performance or functional capability, for instance, in a manner that corresponds to a likelihood that the subject can experience a functional development burst, spurt, or surge.

In an embodiment, a BTI corresponding to a time period T can be mathematically defined as follows:

$$BTI_T = \sum_{\tau=o}^{T} SVC \Big/ \sum_{\tau=0}^{T} RVC \qquad (3)$$

where (a) $BTI_T$ can have a value between 0 and 1, inclusive (e.g., $0.00 \leq BTI_T \leq 1.00$); (b) T is a time period corresponding to a therapy session or a time taken for a particular action or task within a functional development activity sequence; (c) RVC is a relevant voluntary muscle contraction signal as described above, which occurs during time period T; and (d) SVC is a synergistic voluntary muscle contraction signal that occurs during time period T, as described in detail hereafter.

In various embodiments, the categorization or definition of a voluntary muscle contraction as synergistic involves satisfaction of the following conditions:
(a) the muscle contraction should or must be a relevant or successful muscle contraction (e.g., an RVC) corresponding to a body signal measure (e.g., an EMG signal measure) that satisfies a threshold condition, e.g., which exceeds a minimum or threshold muscle contraction signal value (e.g., a muscle contraction threshold parameter); and
(b) the muscle contraction should or must have occurred during or be temporally associated with the subject's attainment or maintenance of each of a mind state and a body state that are conducive to activity or task performance, learning, and/or favourable neural reorganization.

Thus, a synergistic voluntary contraction (SVC) can be defined as a voluntary muscle contraction having a magnitude that meets or exceeds a minimum or threshold value such as a muscle contraction threshold parameter associated with a muscle under consideration, and which occurs when each of the subject's mind state and body state cooperatively facilitate or are conducive to an enhanced, significantly enhanced, or greatly enhanced likelihood of successful activity or task performance, functional development, and/or learning.

In various embodiments, an SVC signal corresponds to an RVC signal that occurs when (a) a set of mind state indicators corresponds to, signifies, or evinces an alert and relaxed mind state; and (b) a set of body state indicators corresponds to, signifies, or evinces an aware and relaxed body state. In multiple embodiments, an RVC signal is categorized or defined as an SVC signal when each of the following conditions is satisfied:
(a) $M_A(t)$ meets or exceeds a minimum or threshold mind state alignment indicator value $M_{A\ threshold}$, thereby satisfying a predetermined, selectable, or programmably generated mind state alignment condition or criterion; and
(b) $B_A(t)$ meets or exceeds a minimum or threshold body state alignment indicator value $B_{A\ threshold}$, thereby satisfying a predetermined, selectable, or programmably generated body state alignment condition or criterion.

One or both of $M_{A\ threshold}$ and $B_{A\ threshold}$ can depend upon embodiment details; the nature, extent, or severity of a type of subject impairment or dysfunction under consideration; and/or subject specific measurements or observations, such as level of subject fatigue or subject motivation at a particular time. In several embodiments, $M_{A\ threshold}$ can be based upon or correlated with resting state EEG signals acquired from one or more healthy or unimpaired individuals, and/or resting state EEG signals obtained from one or more impaired individuals. Similarly, $B_{A\ threshold}$ can be based upon or correlated with EMG signals acquired from one or more healthy or unimpaired individuals, and/or EMG signals acquired from one or more impaired individuals. One or both of $M_{A\ threshold}$ and $B_{A\ threshold}$ can be estimated, established, or determined in a programmable or selectable manner, for instance, in response to clinician or therapist input, or based upon a recent history of subject functional development activity sequence performance.

In a representative implementation, $M_{A\ threshold}$ is defined to have a value between approximately 0.20 and approximately 0.50, where 0.20 can be used for severely impaired or highly anxious subjects, and 0.50 can be used for moderately impaired or generally relaxed subjects. Additionally, $B_{A\ threshold}$ is defined to have a value between approximately 0.20 and approximately 0.50, where 0.20 can be used for severely impaired or at least somewhat or moderately fatigued subjects, and 0.50 can be used for moderately impaired or non-fatigued subjects. In such an implementation, for moderately impaired, relaxed, or non-fatigued subjects, an SVC signal corresponding to time t can be generated in response to the existence or occurrence of an RVC signal at time t that occurs simultaneous or essentially simultaneous with $M_A(t)$ having a value greater than or equal to 0.50 (i.e., $M_A(t) \geq 0.50$ when the RVC signal occurs) and $B_A(t)$ having a value greater than or equal to 0.50 (i.e., $B_A(t) \geq 0.50$ when the RVC signal occurs). For severely impaired, anxious, or at least somewhat fatigued subjects, an SVC signal corresponding to time t can be generated in response to the existence or occurrence of an RVC signal at time t simultaneous or essentially simultaneous with $M_A(t) \geq 0.20$ and $B_A(t) \geq 0.20$.

Multiple variations upon the above SVC signal generation conditions can exist. For instance, with respect to a moderately impaired subject that remains mentally alert and relaxed, yet exhibits at least some degree of muscle fatigue at time t, an SVC signal corresponding to time t can be generated in response to the occurrence of an RVC signal at time t coincident or generally coincident with $M_A(t) \geq 0.50$ and $B_A(t) \geq 0.20$. Analogously, for a moderately impaired subject that is mentally anxious, yet exhibits essentially no muscle fatigue at time t, an SVC signal corresponding to time t can be generated in response to the occurrence of an RVC signal at time t coincident or generally coincident with $M_A(t) \geq 0.20$ and $B_A(t) \geq 0.50$. Furthermore, one or both of $M_{A\ threshold}$ and $B_{A\ threshold}$ can have values other than 0.20 or 0.50, for instance, essentially any value between 0.20 and 0.50 (e.g., approximately 0.30, 0.35, 0.40, or 0.45), or some other value (e.g., approximately 0.10 or 0.60) depending upon embodiment details; the nature, extent, or severity of a type of subject impairment or dysfunction under consideration; and/or subject specific measurements or observations. Moreover, the values of one or both of $M_{A\ threshold}$ and $B_{A\ threshold}$ can be established, determined, or selected to remain constant during a set of functional development activity sequences under consideration or a therapy session, or dynamically or adaptively updated or adjusted based upon subject specific measurements or indicators (e.g., current or recent mind state indicators, body state indicators, and/or subject performance metrics) or observations (e.g., clinician or therapist observations of subject anxiety, frustration, fatigue, or performance level) during functional development activity sequence presentation or a therapy session.

In view of the foregoing, $BTI_T$ can be defined as a cumulative or total number of synergistic voluntary muscle contractions that occurred during time period T, normalized to a cumulative or total number of relevant voluntary muscle contractions that occurred during time period T. Within time period T, at any given time t following the onset or initiation of a therapy session or functional development activity sequence presentation, a current BTI value can be mathematically defined as follows:

$$BTI(t) = \sum_{\tau=0}^{t \leq T} SVC \bigg/ \sum_{\tau=0}^{t \leq T} RVC \qquad (4)$$

where BTI(t) can exhibit a value between 0 and 1, inclusive.

In various embodiments, biofeedback presented to the subject includes visual and/or audio biofeedback that is based upon, correlated with, or indicative of BTI(t). When the subject is able to maintain or sustain a functional state in which BTI(t) remains close, generally close, or approximately equal to 1.00 (e.g., BTI(t) $\geq$ 0.80, 0.90, or 0.95), it is expected that the subject is continuously functioning in a near-optimal or essentially ideal state that exhibits a significant, enhanced, or high likelihood of facilitating or enabling non-incremental spurts or bursts in the subject's functional development, recovery, or learning. In contrast to prior assistive systems and techniques for functional development, embodiments of the present disclosure can provide a quantitative or quantifiable measure of a likelihood or expectation that a subject can experience such non-incremental or burst type functional development results.

In view of the foregoing, a value of BTI(t) and/or $BTI_T$ that is near or approximately equal to 1.00 can indicate that the subject's mind and body are synergistically unified or integrated in a manner that facilitates or enables maximization of the subject's potential for functional development, functional maintenance, learning, and/or neural reorganization, including the potential to attain breakthrough, non-incremental, nonlinear, or spontaneous burst type results.

Because the provision of one or more types of biofeedback to the subject based upon BTI(t) in accordance with embodiments of the present disclosure can result in the subject realizing a unification of their mind state and body state in a manner that is expected to significantly increase the likelihood of realizing significant, surprisingly strong, unexpected, and/or lasting gains in functional capabilities, the provision of biofeedback correlated with or based upon BTI(t) can reinforce or drive neural reward mechanisms associated with the successful realization of functional performance gains. Embodiments of the present disclosure can thus avoid or aid in overcoming subject discouragement, frustration, or lack of motivation that commonly characterize prior assistive systems and techniques for functional development; and/or limited, inadequate, or poor functional development results associated with prior assistive systems and techniques.

Embodiments of the present disclosure described above are directed to training or retraining subject muscle activation synergies associated with movement patterns or sequences, such as compound, complex, and/or intricate movement sequences. Such embodiments generate signals or data corresponding to subject activation of the dominant agonist-antagonist muscles that are known or expected to be involved in exerting primary or substantial control over such movement patterns or sequences, for instance, in healthy or unimpaired individuals. Embodiments of the present disclosure can thus facilitate or enable the subject's development, restoration, and/or maintenance of muscle activation synergies that involve volitional, selective control of dominant agonist-antagonist muscle contractions in a manner that corresponds to true functional recovery, for instance, by way of the subject's learning to coordinate or activate and/or relax biomechanically correct muscles at appropriate times such that the subject can develop the ability to perform a particular compound, complex, or intricate movement pattern or sequence in a reliable, smooth, or increasingly or substantially natural manner.

Additionally or alternatively, various embodiments of the present disclosure can generate information, signals, data analogous to information, signals, and/or data described above (e.g., body state alignment indicators) corresponding to non-dominant or secondary agonist-antagonist muscles that may be involved in controlling compound, complex, or intricate movements in association with control exerted by dominant agonist-antagonist muscles. In some embodiments, a consolidated body state alignment indicator can be mathematically defined as follows:

$$B_{A\ Consolidated}(t)=B_{A1}(t)+B_{A2}(t)+B_{A3}(t)+\ldots \quad (5)$$

where $B_{A1}(t)$ is a body state alignment indicator corresponding to a dominant agonist-antagonist muscle group, $B_{A1}(t)$ is a body state alignment indicator corresponding to a non-dominant or auxiliary agonist-antagonist muscle group, $B_{A3}(t)$ is a body state alignment indicator corresponding to another non-dominant or auxiliary agonist-antagonist muscle group, and so on.

Depending upon embodiment details, subject progress, and/or subject or clinician selection or preferences, once a subject has interacted with the system 10 and learned or relearned how to selectively control a set of dominant agonist-antagonist muscles under consideration, the subject can either develop or apply their own additional movement control synergies and strategies to further develop, improve, or refine particular compound, complex, or intricate movement skills; and/or further interact with the system 10 to learn or relearn one or more manners of selectively controlling a set of non-dominant agonist-antagonist muscles associated with a movement pattern or sequence under consideration, or another movement pattern or sequence related thereto.

Following the subject's learning or relearning of selective volitional control over dominant agonist-antagonist muscles associated with a movement pattern or sequence under consideration, particular embodiments of the present disclosure can present dominant and/or non-dominant agonist and/or antagonist muscle strength training routines, exercises, and/or games to the subject. For instance, strength training routines, exercises, and/or games can involve the gripping, grasping, pinching, and corresponding release of objects.

Various embodiments of the present disclosure are at least initially, and possibly primarily, directed to developing or restoring movement sequence pattern synergies, that is, the development or restoration of synergistic, volitionally selective agonist-antagonist muscle activation patterns that facilitate or enable the subject's learn or relearn of compound, complex, or intricate movement patterns. Such an approach to developing or restoring subject functional capabilities is in contrast to prior assistive approaches to functional development or restoration, which overwhelmingly rely upon strength training alone (often including strength training very early following the occurrence of neurologic damage), which can result in the development of counterproductive or non-synergistic muscle activation patterns that limit or prevent functional development or recovery, for instance, as a result of strength training induced sustained muscle tension.

Prior assistive systems and techniques for functional development or restoration additionally fail to provide biofeedback to the subject in a manner that can facilitate or enable enhanced, accelerated, and/or lasting functional development or restoration as a result of making the subject aware of productive/synergistic and/or non-optimal/non-synergistic (a) body state information including agonist-antagonist muscle activation information; (b) mind state information; and (c) mind-body unification, integration, or mutual reinforcement or cooperation information, one or more of which the subject can volitionally adjust or self correct (e.g., while engaged in functional development activity sequences) in order to increase or maximize a likelihood of experiencing enhanced, accelerated, non-incremental, and/or lasting functional gains.

Aspects of Representative System Embodiments and Subject-System Interaction

FIG. 2A is a schematic illustration of a subject 5 using or interacting with a representative system 10 for unified neurological-physiological rehabilitation and/or functional development according to an embodiment of the disclosure. In the embodiment shown, the system 10 includes a mind signal capture device 100, a body signal capture device 200, and a signal acquisition unit 20 coupled to a computer system or computing device 12 (e.g., a desktop, laptop, or tablet computer) configured to support or provide particular system elements described above with reference to FIG. 1, including a set of input devices 310, a visual interface 320, an audio interface 330, and possibly a kinesthetic interface 340.

The system's mind signal capture device 100 includes a number of EEG electrodes 110 configured to detect EEG signals corresponding to particular neural populations within of the subject's brain. The mind signal capture device 100 can be a wireless or wire-based device that includes a head mountable or wearable article, device, structure, or frame 120 configured to carry EEG electrodes 110 relative to a set of subject scalp locations that is relevant to the generation or determination of mind state indicators, and possibly the generation or determination of subject performance signals. A head mountable article or device 120 can correspond to, be based upon, or include a helmet, cap, or visor (e.g., a baseball type cap); a mesh or net; an EEG capable computer input device or game controller (e.g., an EPOC Neuroheadset, Emotiv Systems Pty Ltd, New South Wales, AU); or another type of structure that carries or supports a number of EEG electrodes 110.

In general, the number of EEG channels that the mind signal capture device 110 is configured to capture, and the particular 10-20 EEG montage locations from which EEG signals are captured, depends upon a type of subject dysfunction or impairment under consideration. In some embodiments directed to developing or maintaining hand function following stroke or traumatic brain injury, or enhancing learning abilities in subjects experiencing learning disorders, the mind signal capture device 100 is configured to capture 8 channels of EEG data. In particular embodiments directed to facilitating functional recovery in subjects experiencing sleep disorders or mild cognitive impairment, the mind signal capture device 100 is configured to capture more channels of EEG data, for instance, 19 channels of EEG data.

In multiple embodiments, the EEG electrodes 110 can be positioned relative to particular scalp locations associated with neural populations of interest in accordance with the standard 10-20 EEG montage. In a representative implementation, the mind signal capture device 100 includes EEG electrodes 110 positioned relative to or at F3, F4, C3, C4, P3, P4, O1, and O2 for monitoring EEG signals relating to the recovery or maintenance of hand function following stroke or traumatic brain injury. The mind signal capture device 100 can include EEG electrodes 110 positioned relative to or at Fp1, Fp2, F3, F4, P5, P6, O1, and O2 for monitoring EEG signals relating to the recovery or maintenance of function in subjects experiencing learning disabilities.

In various embodiments, a body signal capture device 200 includes a number of surface EMG electrodes 210 configured to detect EMG signals corresponding to particular subject muscles or muscle groups that are relevant to the generation or determination of body state indicators as well as subject performance signals. In an embodiment such as that shown in FIG. 2A, EMG electrodes 210 can be positioned to detect EMG signals generated in association with subject control or attempted control of forearm and/or hand muscles relevant to aspects of hand function, such as fine motor function. In multiple embodiments, at least some of the EMG electrodes 210 are carried by an article, device, or structure 210 that can be fitted to or worn by the subject. In a representative implementation, the body signal capture device 200 includes EMG electrodes 210 positioned to detect EMG signals corresponding to at least some of the subject's extensor carpi ulnaris; flexor carpi ulnaris; extensor digitorum; flexor digitorum profundus; pronator teres; supinator; and opponens policis.

The visual interface 320 includes at least one, and possibly multiple, display devices 322 configured to selectively present visual information corresponding to biofeedback, functional activity development sequences, mind state exercises, and body state exercises to the subject 5. For instance, in some embodiments, the visual interface can include a first display device 322a configured to selectively provide visual information corresponding to functional development activity sequences, mind state exercises, and body state exercises to the subject 5; and a second display device 322b configured to provide visual biofeedback information to the subject 5. Aspects of various types of information that can be provided by a representative visual interface 320 are described in detail below with respect to FIGS. 3A-5A.

The set of input devices 310 includes at least one of a mouse 312, a keyboard 314, and a joystick 316 by which the subject 5 can perform or attempt to perform functional development activities relevant to hand, wrist, and/or forearm motor control (e.g., fine motor control such as finger and/or wrist extension and flexion). Additionally, the audio interface 330 includes a set of speakers or headphones 332, and a microphone 334.

FIG. 2B is an illustration of a subject 5 interacting with a representative implementation of the system 10 of FIG. 2A according to an embodiment of the disclosure. In FIG. 2B, the mind signal capture device 100 includes a baseball type cap or visor 120 that is configured to carry EEG electrodes 110 relative to or at some or each of the aforementioned scalp locations. The body signal capture device 200 includes a wearable sleeve 220 configured to carry EMG electrodes 210 relative to or at some or each of the aforementioned forearm and/or hand muscle locations. In several embodiments, the sleeve 220 is flexible or expandable as well as inexpensive. Moreover, one or more portions of the sleeve 220 can be semi-rigid for easier handling with one hand, such that a subject with an impaired hand can don the sleeve 220 with no or minimal assistance.

In a representative implementation, the sleeve 220 is a dual layer medical grade fabric anti-edema tubing that forms an arm glove which carries a set of EMG electrodes 210. More particularly, the sleeve 220 can have a dual layer washable structure, in which an inner layer carries button-on or snap-on EMG electrodes 210 and associated signal transfer wiring or cabling, an outer layer provides sufficient electrode skin pressure to enable good electrode-skin contact in the absence of conductive gel. The pressure exerted by one or more sets of EMG electrodes 210 upon the subject's skin can be predetermined based upon elastic sleeve material characteristics, or can be adjustable using a pressure adjustment mechanism corresponding to each EMG electrode 210 or sets of EMG electrodes 210 in order to accommodate an enhanced or maximum range of arm sizes and compensate for wear and tear or degradation as a result of repeated use or washings. A ground electrode can be fixed with a pre-gelled conductive patch, for instance, at or proximate to the subject's elbow.

Various embodiments of systems 10 in accordance with the present disclosure can facilitate the development or restoration of subject motor and/or sensory function. For instance, systems 10 such as those shown in FIG. 2A or 2B can facilitate the development or rehabilitation of subject hand function following neurologic damage (e.g., resulting from stroke or traumatic brain injury) that has affected hand related motor and/or sensory neural populations. In such embodiments, captured mind signals can include EEG signals corresponding to some or all of the aforementioned 10-20 montage locations, from which mind state indicators can be generated. Captured body signals can include EMG signals corresponding to at least some of the aforementioned hand and wrist muscles, from which body state indicators can be generated.

Functional development activity sequences directed to hand function can be presented to the subject 5 by way of the visual interface 320 and possibly the audio interface 330, and can include visual information (e.g., videos) demonstrating one or more types of wrist, hand, or finger related activities, tasks, actions, or motions that the subject is to perform, attempt to perform, or visualize performing. Subject performance signals acquired during the subject's involvement in such functional development activities can include EMG signals corresponding to the activation of one or more of the aforementioned forearm and/or hand muscles. In certain embodiments, subject performance signals can additionally include EEG signals associated with subject hand function, such as EEG signals acquired from EEG electrodes 110 positioned at scalp locations corresponding to particular portions of the subject's motor cortex, premotor cortex, or sensory cortex.

FIG. 2C is a schematic illustration of a subject 5 using or interacting with a system 10 for unified neurological-physiological rehabilitation and/or functional development according to another embodiment of the disclosure, which can be configured to facilitate the restoration, normalization, or development of one or more types of cognitive and/or emotional function.

In the embodiment shown, the mind signal capture device 100 includes a head mountable device 120 that carries EEG electrodes 110 positioned relative to or at scalp locations corresponding to neural populations that are relevant to the generation or determination of mind state indicators, such one or more scalp locations indicated above. In certain embodiments, the mind signal capture device 100 additionally includes EEG electrodes 110 positioned with respect to scalp locations corresponding to neural populations that are relevant to the subject's performance or attempted performance of a cognitive and/or emotional function under consideration, from which corresponding subject performance signals can be detected, generated, or determined. For instance, the mind signal capture device 100 can include EEG electrodes 110 positioned relative to cortical neural populations corresponding to portions of the left and/or right DLPFC in embodiments directed to normalization of emotional function in a subject 5 experiencing symptoms of MDD or bipolar disorder. For a subject 5 experiencing speech or language deficits, the mind signal capture device 100 can include EEG electrodes 100 positioned relative to speech related cortical neural populations, such as one or both of Wernicke's area and Broca's area.

A set of body signal capture devices 200 can include one or more types of devices configured to detect or capture body signals that can correspond to a level of bodily tension or stress. For instance, a set of body signal capture devices 200 can include a shoulder or neck mountable or wearable article or device 220 that carries a set of EMG electrodes 220 configured to detect EMG signals generated by particular shoulder or neck muscles; a pulse oximeter configured to detect subject heart rate; and/or another type of device, such as a skin conductance monitor.

A functional development activity sequence can involve subject engagement in tasks or activities that are relevant to the development, normalization, or restoration of subject functions corresponding to a clinical indication under consideration. For instance, for a subject 5 experiencing symptoms of MDD or another type of neuropsychiatric condition, a functional activity development sequence can include virtual reality scenarios. For such a subject 5, a functional development activity sequence can additionally or alternatively include an interactive or online individual or group therapy/teaching/training session, such as a Cognitive Behavioural Therapy (CBT) or Dialectical Behavioural Therapy (DBT) session. For a subject 5 experiencing speech or language deficits, a functional development activity can include speech therapy exercises, which can occur on a stand alone or an interactive basis with a remote speech therapist.

Figure 2D:
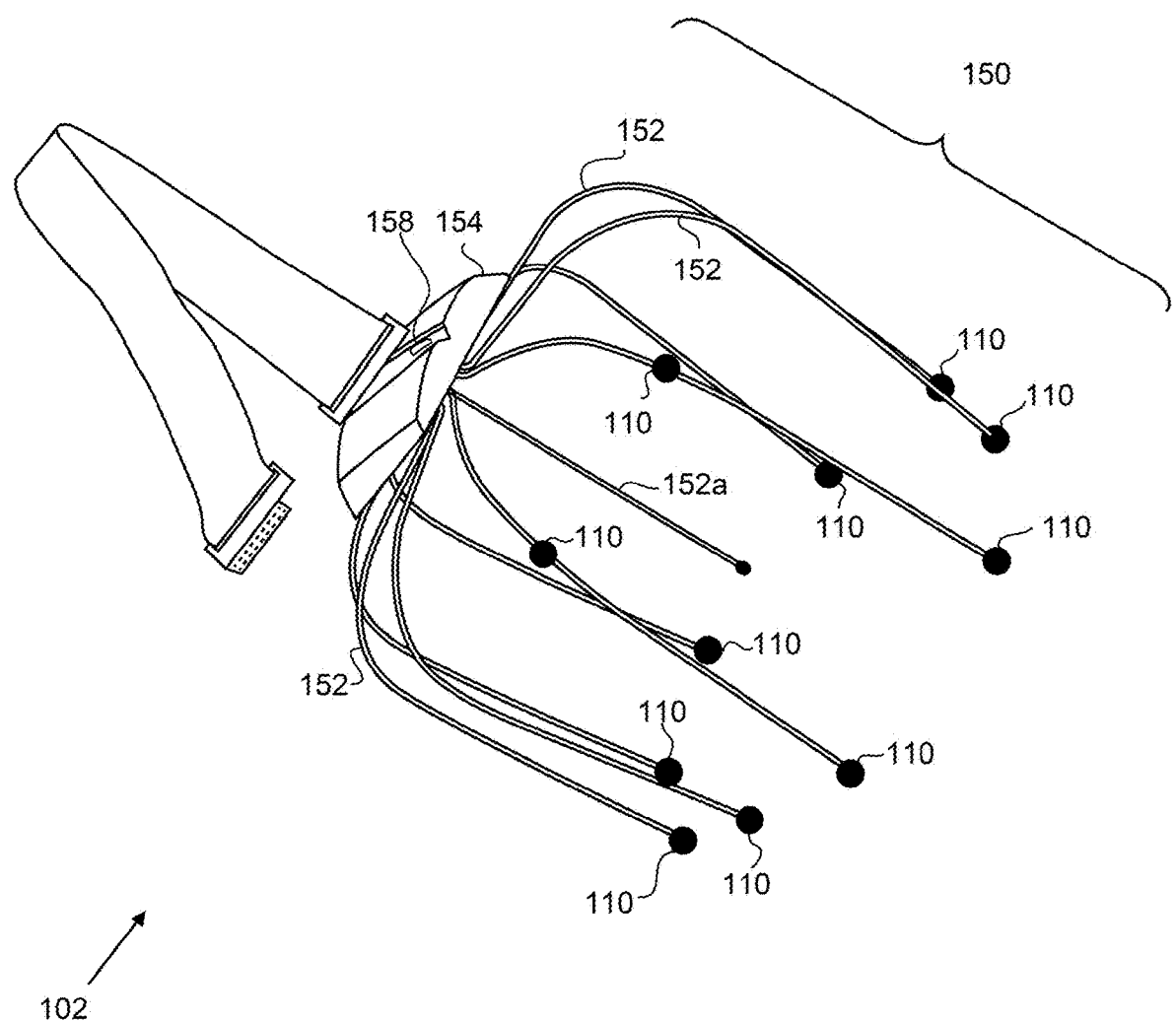
FIG. 2D is a schematic illustration of a representative EEG signal capture device 102 according to another embodiment of the disclosure.

Subject performance signals in embodiments directed to cognitive or emotional function development, normalization, or restoration can include EEG signals, subject speech signals, a cognitive or emotional skills assessment score (e.g., corresponding to a Beck depression inventory), and/or mind state maintenance and body state maintenance scores.
Additional/Other Types of Mind Signal or Body Signal Capture Devices Systems such as those described above can include various types of mind signal capture devices 100 and/or body signal capture devices 200. For instance, FIG. 2D is a schematic illustration of a representative EEG signal capture device 102 according to another embodiment of the disclosure. In an embodiment, such an EEG signal capture device 102 includes a plurality of tines 152 that are coupled to a hub structure 154. The tines 152 form a flexible or semi-flexible frame 150 that is configured to slidably mount upon the subject's head in a manner that is identical, essentially identical, or analogous to that of a handheld scalp massager having a number of flexible tines, prongs, or fingers (e.g., ball-tipped wire tines), such that spring type tension can retain the tines 152 in a desired position upon the subject's head.

The frame 150 carries a set of EEG electrodes 110 at locations on the tines 152 that correspond or are expected to correspond to particular (e.g., predetermined) 10-20 EEG montage locations. The tines 152 themselves can be electrically insulated or nonconductive. At least one reference tine 152a can serve as a position reference relative to at least one subject anatomical structure, such that the EEG electrodes 110 can be positioned with respect to portions of the subject's scalp in a consistent, repeatable manner. For instance, correct positioning of the frame 150 upon the subject's scalp can correspond to a reference tine 152a positioning immediately behind the subject's left ear. The EEG electrodes 110 are coupled to a signal transfer interface 158, which can be a wireless or wire-based interface carried by the hub structure 154 for communicating EEG signals to a signal acquisition unit 20.

Figure 2E:
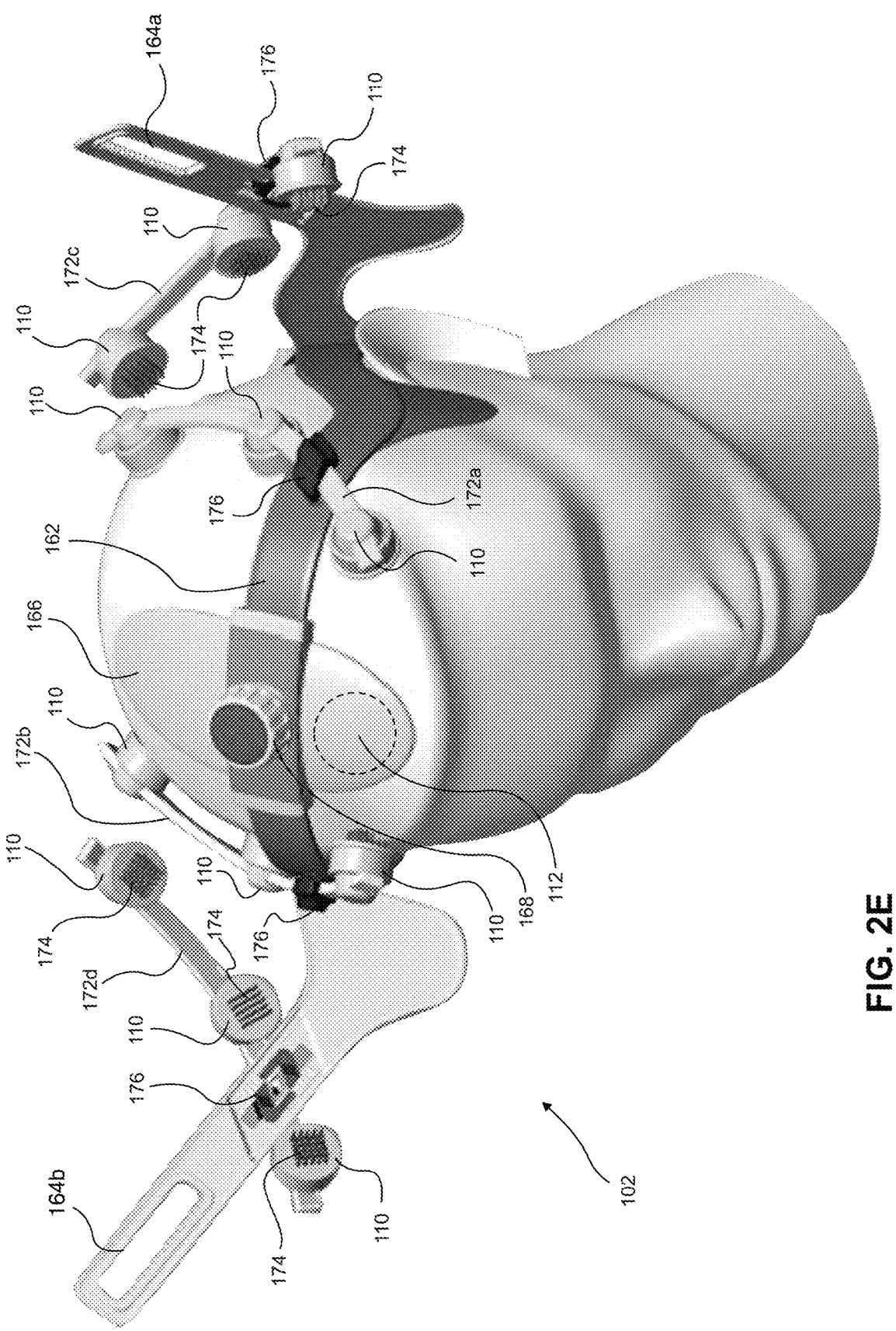
FIG. 2E is a schematic illustration of an EEG signal capture device according to another embodiment of the disclosure.

FIG. 2E is a schematic illustration of an EEG signal capture device 102 according to another embodiment of the disclosure. The device includes a single flexible band or band assembly 162 which when worn will rest on a wearer's head, extending above and across the wearer's head and tapering downward on each side of the head slightly in front of the ear before it rests above the ear, and then further extending to the back of the wearer's head. The flexible band 162 is configured for fittable or adjustable (e.g., size/shape adjustable) engagement with a subject's head.

In various embodiments, an opening 164 is located at or proximate each of two ends of the band to accommodate a jog dial (not shown) for adjustment according to the size of the wearer's head. A central pad 166 which rests on the top of the wearer's head includes a ground electrode 112 which is coupled to a substantially central position of the flexible band 162, and is adjustable between a substantially frontal and a substantially centre-back position of the head via a jog dial 168.

Coupled to the flexible band 162 on each of the left and right sides of the wearer's head via a coupling fixture is a first accessory strip 172a and a second accessory strip 172b respectively. Each of the first and second accessory strips 172a, 172b carries a plurality of EEG electrodes 110. Each electrode 110 is fitted on the strip through insertion sites of on a body of the electrode 110 so that the strip can be passed or strung along or through a portion of the EEG electrode 110.

In an embodiment, the EEG electrodes 110 include dry EEG electrodes. Each of the EEG electrodes 110 can include multiple EEG sensing elements, such as an array (e.g. a 5×5 array) of sensor pins 174. Within the array of sensor pins 174, some or all of the EEG sensing elements can be resiliently biased, e.g., spring loaded, to facilitate conformity to scalp topology/head profile and reliable EEG signal detection. The sensor pins 174 can be made using a highly conductive material, for instance, gold plated silver, or gold plating on any high conductivity material like copper or aluminum. The EEG electrodes 110 can be connected to signal amplifiers, which can be carried by the EEG electrodes 110 themselves or disposed external to or remote from the EEG electrodes 110. The wiring within the device 102 runs from the electrodes 110 to the connector (not shown) of the device 102 at the back of the subject's head.

In an embodiment the coupling fixture 176 on each of the strips 172a, 172b is disposed between the first and second electrodes relative to the front of the head. The fixture 176 coupled to the flexible band 162 on each side is adjustable between a substantially higher position (towards the central pad) on the flexible band 162 and a substantially lower position (towards the wearer's ear) on the flexible band 162. Each of the EEG electrodes 110 disposed along or on the strip 172a,b is position-adjustable along the length of the strip 172a,b.

A further third and fourth accessory strips 172c,d carrying a plurality of EEG electrodes 110, similar to the first and second accessory strips 172a,b, can be coupled to each end of the band 162 nearer to the inner side of each of the openings 164 respectively, via a coupling fixture 176 on each strip. The coupling fixture 176 is disposed between a first electrode and a second electrode on each strip, of which a first electrode 110 is nearest to the end of the strip. The coupling fixture 176 of each of the third and fourth strips 172c,d is adjustable along a section of the length of the band 162 at each of the ends before the opening. Each of the EEG electrodes 110 on the third and fourth strips 172c,d is further adjustable along the length of the appropriate strip 172c,d.

Figure 2F:
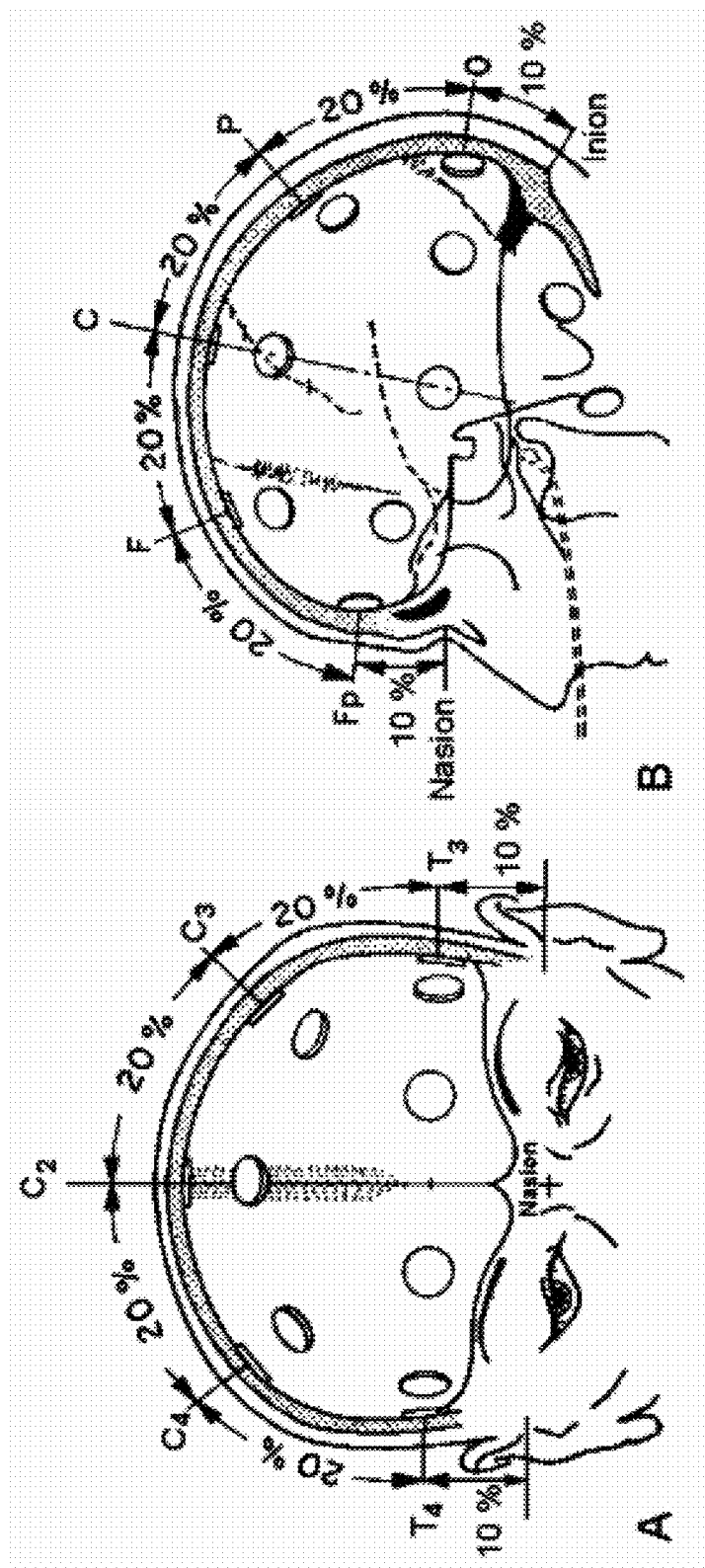
FIG. 2F is a schematic illustration showing measurements of a subject's head circumference and arc-wise or circular distance between nasion and inion.
Figure 2G:
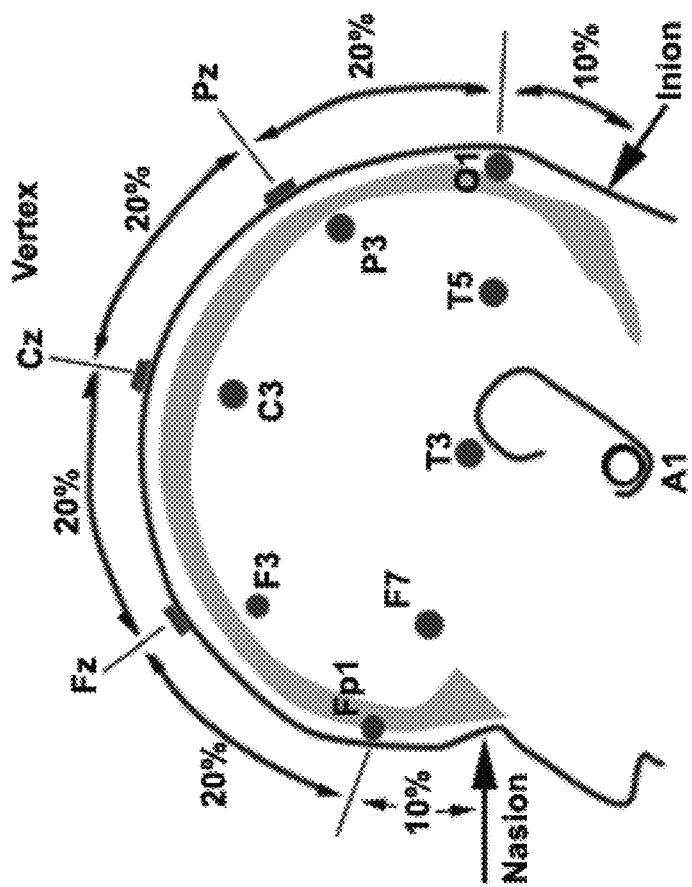
FIG. 2G is a conventional EEG configuration protocol corresponding to FIG. 2F.

The adjustment of the electrode positions can be based on 1) the subject's profile which includes at least measurements of the head circumference and arc-wise or circular distance between nasion and inion, as shown in FIG. 2F; and 2) a electrode distribution map (e.g. defined based upon, in support of, or with a conventional EEG configuration, montage, or protocol), as shown in FIG. 2G. A device 102 in accordance with various embodiments of the present disclosure can be shaped, dimensioned, tailored and/or adjustable to accommodate small, medium, and/or large head sizes, and/or expected anatomical head differences between different racial groups. In view of the foregoing, in various embodiments, EEG electrodes carried by an EEG signal capture device 102 can be adjustably, selectively, or slidably positioned in multiple directions, e.g., relative to or along each of an anterior-posterior direction as well as a superior-inferior direction, to facilitate adaptive accommodation of different head shapes, sizes, and topology.

Figure 2H:
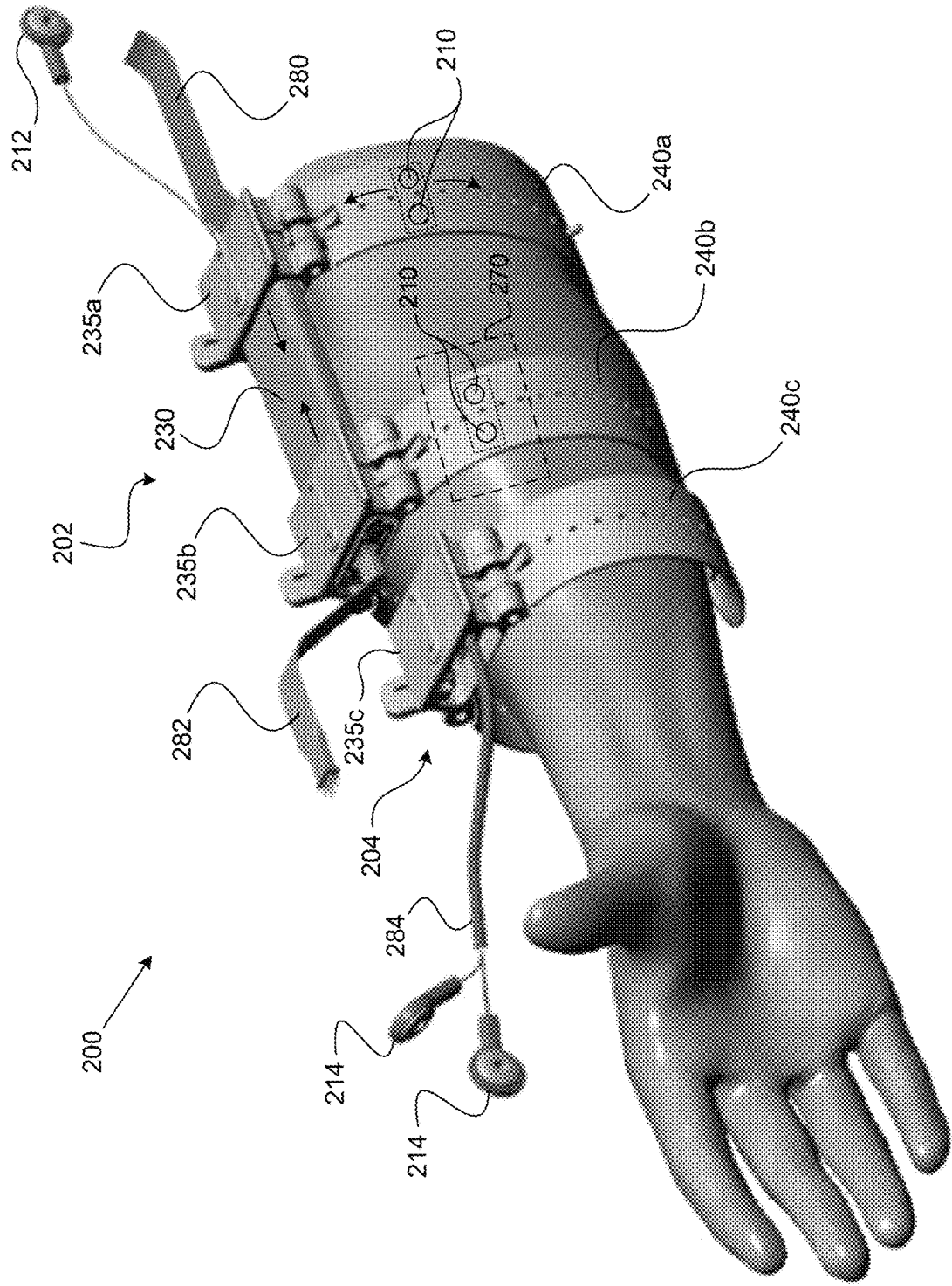
FIG. 2H is a schematic illustration of an adjustable and/or modular body signal capture apparatus according to an embodiment of the disclosure.

FIG. 2H is a schematic illustration of an adjustable and/or modular body signal capture apparatus or device 200 in accordance with an embodiment of the present disclosure. In an embodiment, such a body signal capture apparatus 200 includes a primary body signal capture apparatus or device 202, which can optionally be coupled to at least one auxiliary body signal capture apparatus or device (e.g., a secondary apparatus or device) 204. Each of the primary body signal capture apparatus 202 and the auxiliary body signal capture apparatus 204 can be adjustable for accommodating an individual subject's anatomical shape(s), dimension(s), and/or limitation(s). In addition, in various embodiments, the primary body signal capture apparatus 202 and the auxiliary body signal capture apparatus 204 are configured for single-hand fitting on, adaptation or adjustment to, and removal from a subject's body, such that a subject can put the primary and auxiliary body signal capture apparatuses 202, 204 on their body and remove such apparatuses 202, 204 from their body without assistance from another person, e.g., by way of the subject utilizing an unimpaired, substantially unimpaired, slightly impaired, or possibly moderately impaired hand. Thus, each portion of the adjustable/modular body signal capture apparatus 200 is configured such that a subject can don, adjust, wear, use (e.g., during functional development activities, body state training exercises, and activities of daily living), and doff the apparatus 200 independently and in a time efficient manner.

In several embodiments, the primary body signal capture apparatus 202 includes a main frame element, member, or bar 230; a set of spring loaded fasteners or clips 235a,b (e.g., a first and a second spring loaded clip 235a, 235b) coupled or couplable to the bar 230; and a set of wearer bands or straps 240a,b (e.g., one or more appendage straps, such as a first and a second forearm strap 240a,b) coupled to each spring loaded clip 235a,b. One or more of the straps 240a,b is configured for carrying at least one set of EMG electrodes or sensors 210 (e.g., the first strap 240a can carry a first set of EMG electrodes 210a, and the second strap 240b can carry a second set of EMG electrodes 210b). Such EMG electrodes 210 can be position adjustable along a portion of a strap length or curvature, as further detailed below.

The primary body signal capture apparatus 202 additionally carries or includes a set of electrical interfaces and electrical signal communication or routing elements (e.g., wiring). In various embodiments, the electrical signal communication/routing elements are carried by the bar 230. Depending upon embodiment details, particular electrical signal communication/routing elements can be configured for wire-based or wireless signal transfer. In a number of embodiments, the bar 230 is configured to facilitate signal communication between the primary and auxiliary body signal capture apparatuses 202, 204 and a signal acquisition unit 20. For instance, the bar 230 can carry at or proximate to a first end a first electrical interface configured for coupling to a first electrical signal communication link or cable (e.g., a first multi-wire planar cable) 280. The first electrical interface can further be configured for coupling to a reference, common, or ground electrode 212. The bar 230 can additionally carry at or proximate to a second end a second electrical interface configured for coupling to an auxiliary body signal capture apparatus 204, such as by way of a second electrical signal communication link or cable (e.g., a second multi-wire planar cable 282).

An auxiliary body signal capture apparatus 204 can include an auxiliary spring loaded fastener or clip 235c, and an auxiliary wearer band or strap 240c coupled thereto. The auxiliary body signal capture apparatus 204 is also configured for coupling to a set of electrical signal communication or routing elements. For instance, the auxiliary spring loaded clip 235c can carry a third electrical interface configured for coupling to the primary body signal capture apparatus' second electrical signal communication link 282, and which is further configured for coupling to a set of auxiliary electrodes (e.g., palm electrodes) 214 by way of a third communication link or wire 284.

In addition to the foregoing, the primary body signal capture apparatus 202 can couple to, be fitted over, or include one or more FES patches/electrodes 270. For instance, the second set of EMG electrodes 210b can be carried by and positioned relative to the length or curvature of the second strap 240b such that the second set of EMG electrodes 210b overlay and are in electrical signal communication with an FES patch 270. Consequently, the body signal capture apparatus 200 can be configured for each of EMG signal measurement and FES signal delivery, e.g., in a selectable or time segregated/multiplexed manner. In a representative implementation, FES signals can be delivered during or in association with functional development activities in accordance with an on-off protocol such as approximately 2-4 seconds on, 6-10 seconds off/rest. FES signals can additionally or alternatively be delivered during or in association with body part training exercises, for instance, in accordance with an on-off protocol such as approximately 15 seconds on, 10 or more seconds off/rest.

In some embodiments, a primary and/or an auxiliary body signal capture apparatus 202, 204 can also be couplable or coupled to one or more other types of body signal sensing devices or elements, such as a pulse oximeter (e.g., a finger-worn pulse oximeter), a temperature sensor, a skin conductance sensor, a sweat sensor, or other type of physiologic parameter sensor.

With respect to mounting the primary body signal capture apparatus 202 to a subject's body (e.g., a forearm), when the spring loaded clips 235a,b are in an open position, the subject can position the first and second straps 240a,b upon or partially around a portion of their body, such as a forearm corresponding to an impaired hand, using an unimpaired hand. At least one spring loaded clip 235a,b is displaceable or position-adjustable (e.g., slidably adjustable) along a lengthwise portion of the bar 230 to facilitate adjustability with or conformity to different body part sizes (e.g., different forearm sizes). For instance, the subject can use an unimpaired hand to adjust the position of the second clip 235b along the length of the bar 230 in a manner that accommodates the subject's individual anatomical structure. A set of EMG electrodes 210 is selectively displaceable along a portion of its corresponding strap 240 to facilitate subject specific EMG electrode positioning 210 for accommodating the subject's individual anatomy. When a spring loaded clip 235a,b is closed, the strap 240a,b corresponding to the clip 235a,b is secured to the subject's body, such that reliable electrical signal communication can occur between the EMG electrodes 210 and subject muscles over which the EMG electrodes 210 reside.

Aspects of Representative Visual Interfaces

During a subject's interaction with the system 10, the system selectively presents biofeedback, functional development activity sequences, body state exercises, and mind state exercises to the subject 5 by way of the subject interaction unit 300. More particularly, portions of the visual interface 320 selectively output visual information corresponding to subject biofeedback, functional development activity sequences, mind state exercises, and body state exercises.

Representative Biofeedback Visual Interfaces

Figure 3A:
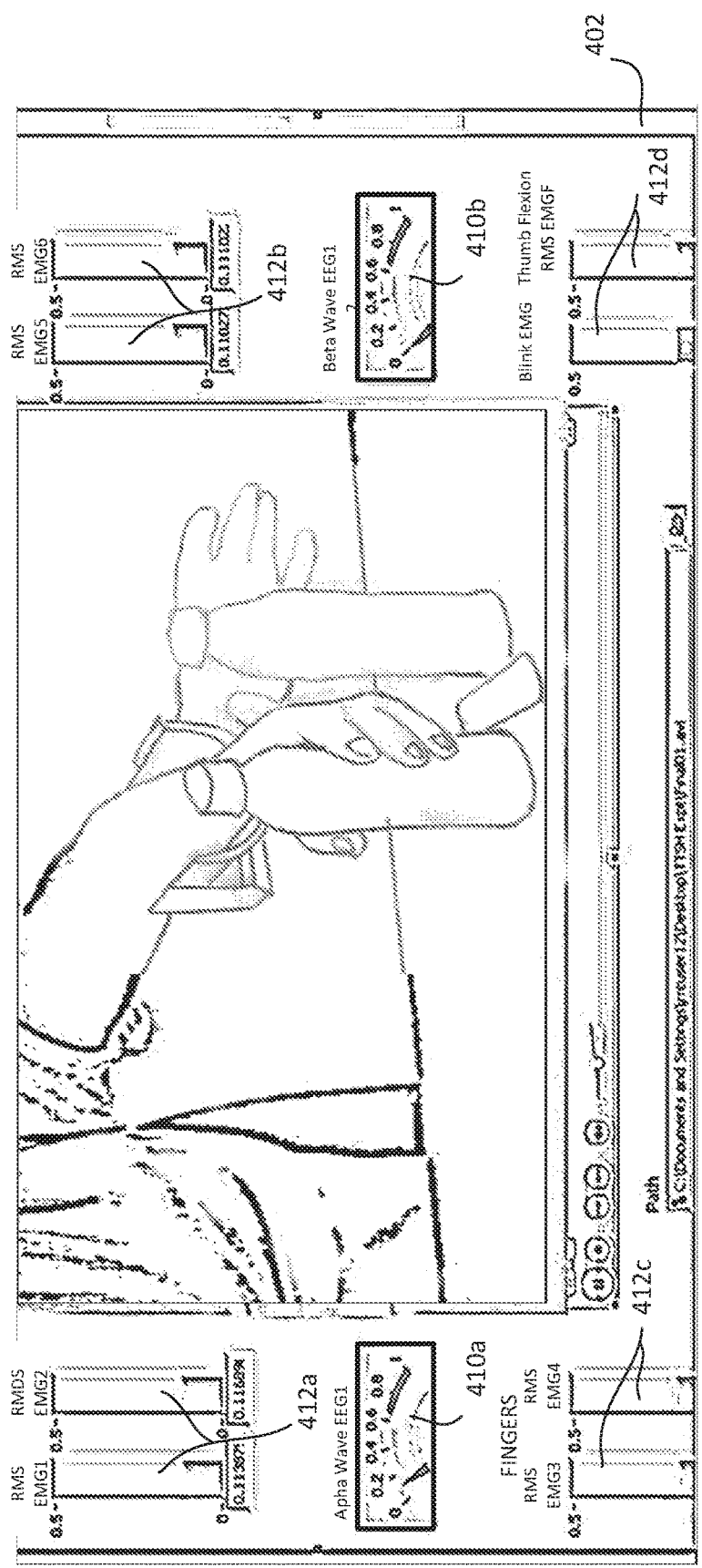
FIG. 3A depicts portions of a representative visual biofeedback interface according to an embodiment of the disclosure.

FIG. 3A depicts portions of a representative visual biofeedback interface 400 according to an embodiment of the disclosure. In various embodiments, a biofeedback interface 400 is configured to simultaneously present both neurological or mind state related biofeedback and physiological or body state related biofeedback. Depending upon embodiment details, a visual biofeedback interface 400 can be separate from or combined or integrated with one or more other types of interfaces, such as a functional development activity sequence interface, a mind state exercise interface, and/or a body state exercise interface. For instance, in some embodiments such as that shown in FIG. 3A, the biofeedback interface 400 is combined with a functional development activity sequence viewing interface or window, such that the biofeedback interface 400 and a functional development activity sequence viewing interface can be displayed by way of a single display device 322. In certain embodiments, a visual biofeedback interface 400 and a functional development activity sequence interface are presented or displayed using physically distinct or separate display devices, such as the first display device 322a and a second display device 322b described above with reference to FIGS. 2A-2C.

In an embodiment, the visual biofeedback interface 400 includes one or more graphical windows 402 in which a set of visual or graphical mind state feedback elements 410 and a set of visual or graphical body state feedback elements 412 are presented or displayed. In a representative embodiment, the set of visual mind state feedback elements 410 can include one or more meter type elements 410a,b configured to visually convey an extent to which aspects of the subject's current mind state remain conducive to functional maintenance, functional development, learning, and/or beneficial neuroplasticity. For instance, the set of visual mind state feedback elements 410 can include a first meter type element 410a configured to display first mind state indicator information such as an EEG measure correlated with current alpha band activity; and a second meter type element 410b configured to display second mind state indicator information such as an EEG measure correlated with current beta band activity. A set of visual mind state feedback elements 410 can additionally or alternatively be configured to present or display other mind state related information, such as visual representations of current values of particular mind state indicators (e.g., current mind state alignment indicators values $M_A(t)$).

A set of visual body state feedback elements 412 can include one or more meter type elements 430a-d configured to visually convey an extent to which aspects of the subject's current body state remain conducive to functional maintenance, functional development, learning, and/or beneficial neuroplasticity. A set of visual body state feedback elements 412 can include a first set of bar type display elements 412a configured to display first body state indicator information such an EMG measure correlated with wrist muscle activation; a second set of bar type display elements 412b configured to display second body state indicator information such as an EMG measure correlated with forearm muscle activation; a third set of bar type display elements 412c configured to display third body state indicator information such as an EMG measure correlated with finger muscle activation; and a fourth set of bar type display elements 412d configured to display fourth body state indicator information such as an EMG measure correlated with thumb muscle activation. Additionally or alternatively, a set of visual body state display elements 412 can be configured to present or display other body state related information, such as visual representations of current values of particular body state indicators (e.g., current body state alignment indicator values $B_A(t)$).

In some embodiments, one or more visual mind state feedback elements 410 can be color coded in accordance with current body state information, for instance, based upon the current values of one or more body state indicator values (e.g., a current body state alignment indicator value $B_A(t)$). Analogously, one or more visual body state feedback elements 412 can be color coded in accordance with current mind state information, for instance, based upon the current values of one or more mind state indicator values (e.g., a current mind state alignment indicator value $M_A(t)$). As a result, a subject can simultaneously ascertain both mind state and body state related information based upon viewing a single visual mind state feedback element 410 or a single visual body state feedback element 412, which can reduce or eliminate unnecessary distraction and facilitate more rapid or natural realization of synergistic mind and body states.

In multiple embodiments of the present disclosure, a visual biofeedback display interface 400 can additionally or alternatively include a set of visual feedback elements configured to convey mind-body alignment information. For instance, FIGS. 3B-3D are schematic illustrations of a representative embodiment of a visual mind-body alignment feedback element 414 configured to visually convey current mind state alignment and body state alignment related information to the subject. In an embodiment, a visual mind-body alignment feedback element 414 can include a plurality of visual mind-body alignment ranking elements 416*a-d*, as well as a visual representation of the subject 418 that is positioned relative to the visual mind-body alignment ranking elements 416*a-d* based upon a current $M_A(t)$ value and a current $B_A(t)$ value relative to a threshold mind state alignment indicator value $M_A$ threshold and a threshold body state alignment indicator value $B_{A\ threshold}$, respectively.

The visual mind-body alignment ranking elements 416*a-d* can be color coded relative to each other. For instance, a first visual mind-body alignment ranking element 416*a* can correspond to a green color; a second visual mind-body alignment ranking element 416*b* can correspond to a yellow color; a third visual mind-body alignment ranking element 416*c* can correspond to an orange color; and a fourth visual mind-body alignment ranking element 416*d* can correspond to a red color. The first visual mind-body alignment ranking element 416*a* can correspond to a mind-body alignment situation, condition, or state. A spatial arrangement and/or color coding of the second through fourth visual mind-body alignment ranking elements 416*b-d* relative to the first visual mind-body alignment ranking element 414*a* and each other can convey or correspond to progressively larger magnitudes of non-optimal mind-body alignment.

In a representative implementation, a visual mind-body alignment feedback element 414 can include or be a graphical pyramid type structure having multiple graphical tiers that serve as visual mind-body alignment ranking elements 416*a-d*. When current $M_A(t)$ and $B_A(t)$ values correspond to a synergistic alignment or unification of the subject's mind state and body state, the visual representation of the subject 418 can be positioned on top and in the center of the first mind-body alignment ranking element 416*a*, at a graphical location corresponding to the top of the pyramid structure at the pyramid structure's a lateral midpoint. Thus, FIG. 3B corresponds to a situation in which the subject's mind state and body state are aligned.

As the current $M_A(t)$ and $B_A(t)$ values relative to $M_{A\ threshold}$ and $B_{A\ threshold}$ respectively correspond to larger degrees or magnitudes of non-optimal alignment of the subject's mind state and body state, the visual representation of the subject 418 is positioned further away from the lateral midpoint of the pyramid, proximate to or upon a lateral end of a particular visual mind-body alignment ranking element 416*b-d* that corresponds to a current degree, extent, or magnitude of mind state-body state non-alignment. The positioning of the visual representation of the subject 518 at a particular lateral end (e.g., a left end or a right end) of a given visual mind-body alignment ranking element 416*b-d* can be based upon whether a degree, extent, or measure of non-optimal mind state alignment exceeds a degree, extent, or measure of non-optimal body state alignment. For instance, when a measure of mind state alignment non-optimality exceeds a measure of body state alignment non-optimality, the visual representation of the subject 418 can be positioned relative to a predetermined lateral end (e.g., a left end) of an appropriate visual mind-body alignment ranking element 416*b-d*.

Hence, FIG. 3C corresponds to a situation in which the subject's mind state and body state are non-optimal with respect to mind state-body state alignment, and the contribution of the subject's current mind state to such non-alignment exceeds the contribution of the subject's current body state to such non-alignment. FIG. 3D also corresponds to a situation in which the subject's mind state and body state are non-optimal with respect to mind state-body state alignment, and the contribution of the subject's current body state to such non-alignment exceeds the contribution of the subject's current mind state to such non-alignment. Moreover, the degree or magnitude of mind state-body state non-alignment shown in FIG. 3D exceeds the degree or magnitude of mind state-body state non-alignment shown in FIG. 3C.

In response to viewing current, real time, or near-real time mind-body alignment information, for instance, as conveyed by a visual mind-body alignment feedback element 414, the subject can volitionally adjust or adapt their mind state and/or body state in a manner that increases a likelihood that the subject's mind state and body state become aligned.

Representative Functional Development Activity Sequence Interfaces

Figure 4A:
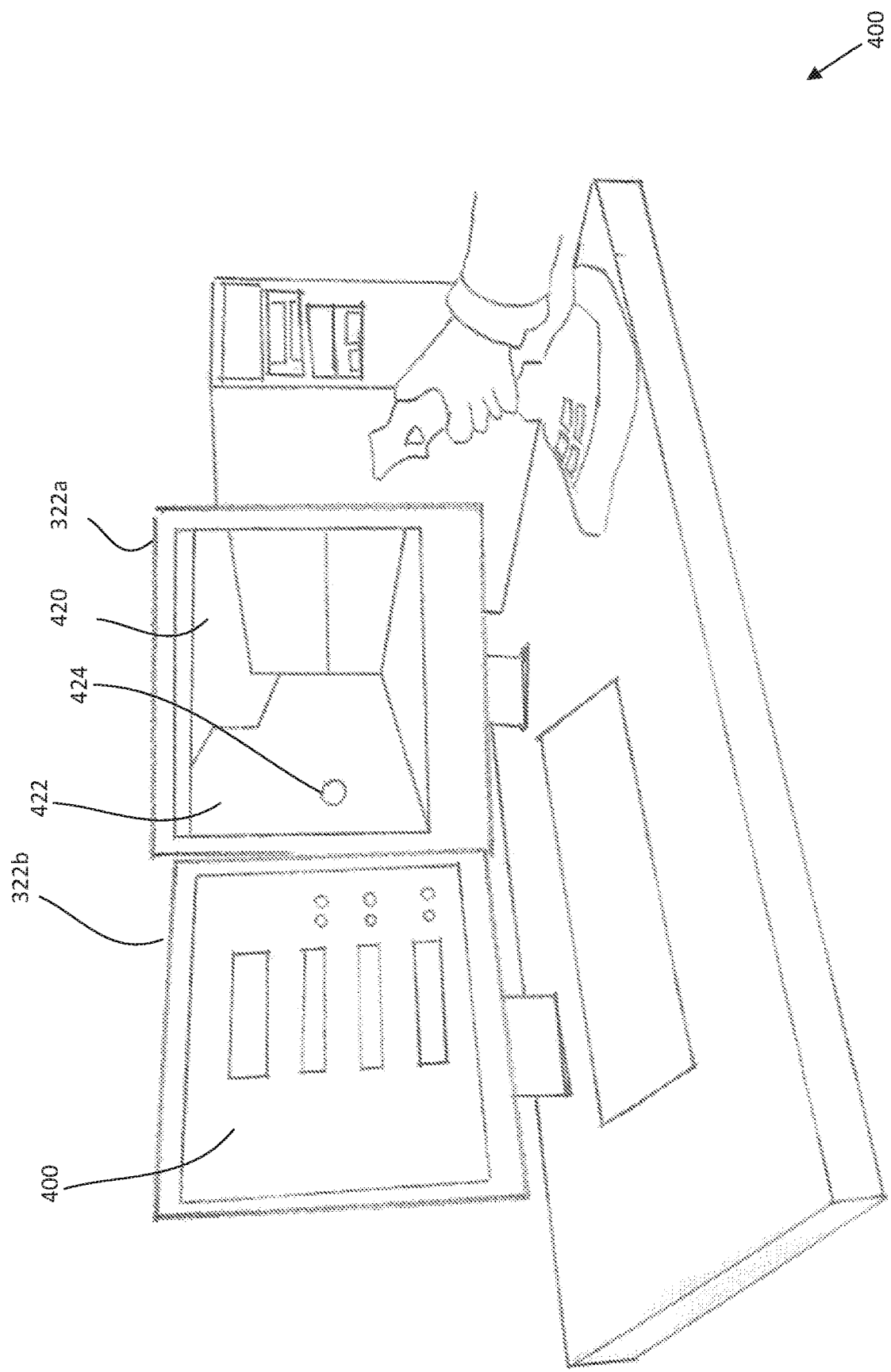

FIG. 4A depicts a representative first functional development activity sequence interface 420 according to an embodiment of the disclosure. In the embodiment shown in FIG. 4A, the first functional development activity sequence interface 420 is presented by a first display device 322*a*, and a visual biofeedback interface 400 is presented by a second display device 322*b*. In an embodiment, the first functional development activity sequence interface 420 includes a visual window 422 that presents one or more visual or graphical objects 424 such as a ball to the subject. The visual biofeedback interface 400 outputs visual information that conveys the subject's current mind state and body state, such as a current relative alpha band power level indicating an extent to which the subject's mind state corresponds to a state of relaxed attention.

In a representative implementation, the subject is instructed to follow or attempt to follow a particular displayed object 424 using an input device 310 such as a joystick. One or more motion parameters corresponding to a graphical object 424 under consideration 424 (e.g., speed of travel) are responsive to a current mind state indicator value, for instance, the current value of an EEG measure such as a relative alpha band power measure. More particularly, in response to a higher relative alpha band power measure, the graphical object 424 under consideration moves more slowly and/or in a more easily controllable manner. Correspondingly, as the current relative alpha band power measure increases, indicating that the subject is attaining or maintaining a relaxed yet alert mind state, the likelihood that the subject can successfully control or follow the motion of the graphical object 424 increases. The subject can experience improved hand-eye coordination simultaneous with relaxed attention training.

FIG. 4B depicts a representative second functional development activity sequence interface 430 according to another embodiment of the disclosure. In the embodiment shown, the second functional development activity sequence interface 430 provides or presents functional development activity sequences to the subject, which can include a first visual set, sequence, or series of functional development activities or tasks 432*a* and a second visual set, sequence, or series of functional development activities or tasks 432*b*. For instance, the first visual set of functional development activities 432*aa* can involve picking up and moving a bottle 434, and the second visual set of functional development activities 432*b* can involve holding and manipulating a pair of chopsticks 436 (e.g., to pick up, move, and release an object using the chopsticks 436). One or both of the first and second visual sets of functional development activities 432*a-b* can involve spatially moving or manipulating objects or items with respect to the location or position of a spatial marker 438. Each visual set of functional development activities 432*a-b* can be displayed to the subject by way of one or more display devices 322, in a manner analogous to that described above. Simultaneous with the display of a given visual set of functional development activities 432a-b, mind state biofeedback and body state biofeedback are displayed to the subject by way of a visual biofeedback interface 400, for instance, in a manner analogous or similar to that described above.

Visual functional development activities 432 can include videos and/or animations that present at least one model body part performing one or more types of target motions/movements that the subject is to imitate or attempt to imitate. In general, any given set of visual functional development activities 432 can be presented to the subject in a "mirror image" manner. Thus, a movement, motion, action, or task performed by a left appendage (e.g., left hand or arm) of an individual demonstrating or performing a task within a set of visual functional development activities 432 under consideration is intended to be mirrored, imitated, or followed by subject movement or attempted movement of their corresponding right appendage.

A given activity or task within a visual set of functional development activities 432 is presented at a particular activity rate, speed, or intensity that the subject is to match or attempt to match. As a result, subject spatial control over aspects of appendage motion, temporal control over aspects of appendage motion, and subject mental attention can be integrated during the subject's performance or attempted performance of a functional development activity sequence under consideration. As further described in detail below, an activity intensity associated with functional development activity sequence presentation can be dynamically adapted based upon aspects of the subject's mind state and body state.

While or in association with performing or attempting to perform, follow, or imitate a visual set of functional development activities 432, the subject can view a visual biofeedback interface 400 to check current mind state indicator values and/or body state indicator values, and volitionally adjust or adapt their mind state and/or body state based upon such biofeedback in a manner that increases a likelihood of successful performance of a functional development activity or task under consideration. Upon completion of one visual set of functional activity sequences 432a, a next visual set of functional development activity sequences 432b can be presented to the subject.

Representative Mind State Exercise and Body State Exercise Interfaces

Figure 5A:
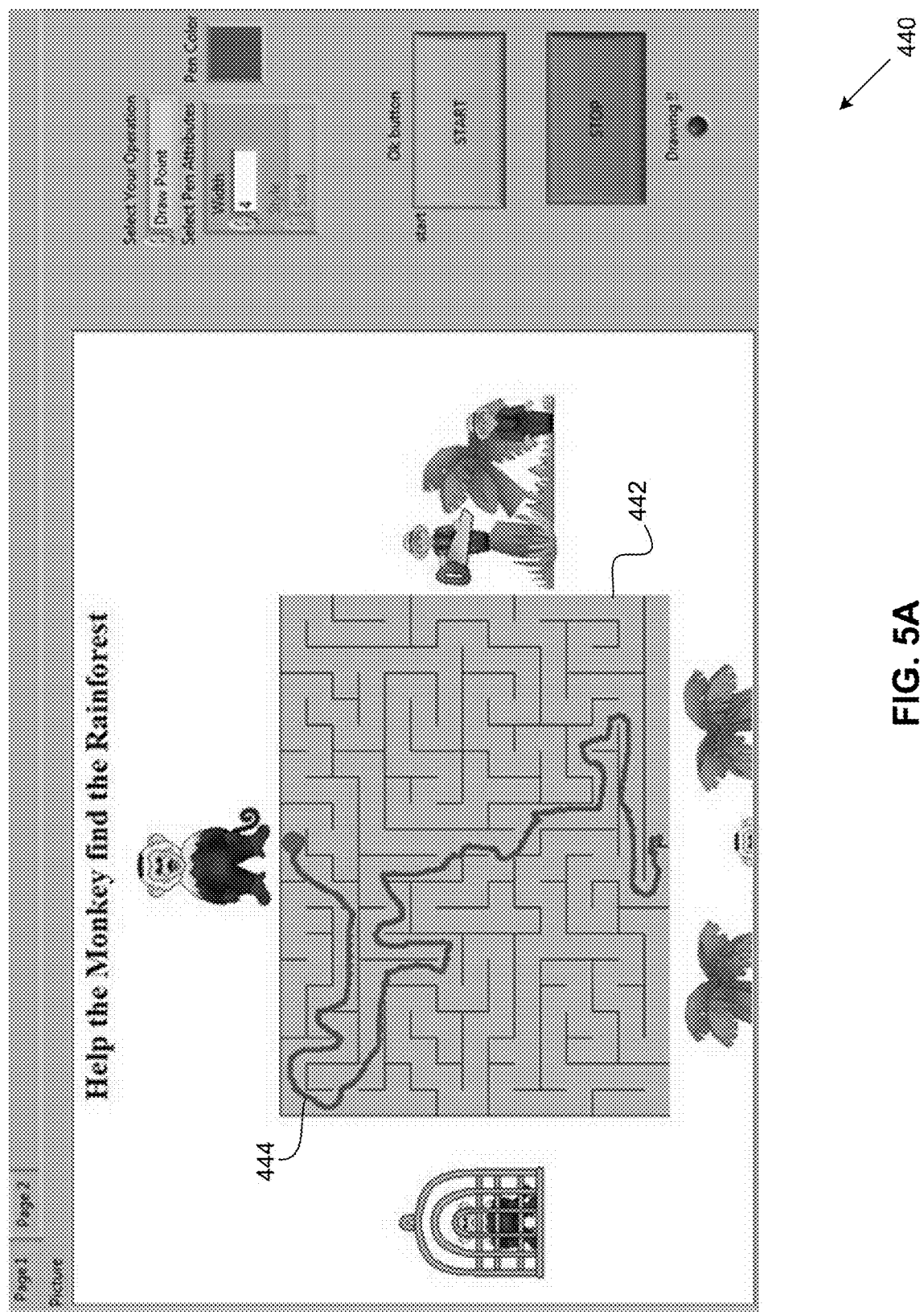
FIGS. 5A and 5B respectively depict a representative first mind state training or exercise interface according to an embodiment of the disclosure and a representative second mind state training or exercise interface according to an embodiment of the disclosure.

FIG. 5A depicts a representative first mind state training or exercise interface 440 according to an embodiment of the disclosure. In an embodiment, the first mind state exercise interface 440 includes a first visual or graphical mind state training exercise or game such as a maze 442 that the subject is to navigate using an input device 310 that serves as a drawing tool. The maze can have a background colour that depends upon a current value of a mind state indicator. Additionally, subject motion of the drawing tool results in the generation of a graphical line 444 having a colour that depends upon a current value of a mind state indicator. Depending upon a manner in which the subject maintains or fails to maintain current values of one or more mind state indicators relative to a set of target training values or value ranges, the background colour of the maze 442 relative to the colour of the graphical line 444 can change, making maze navigation easier or more difficult.

In a representative implementation, the maze 442 can initially have a green background colour, and the graphical line 444 can have a red colour. If the subject maintains a current value of mind state alignment indicator $M_A(t)$ within a first range of values that is near of generally a value of 1.00 (e.g., above a target minimum training value of approximately 0.75), such that the subject's mind state is characterized by a high relative alpha band power measure (e.g., $\overline{P_\alpha}$) and a low DAR measure, the green background colour of the maze 442 is maintained, and the visual contrast between the background colour of the maze 442 and the colour of the graphical line 444 facilitates successful identification of a path to a maze exit, and/or timely navigation through the maze.

If the current value of the mind state alignment indicator $M_A(t)$ falls or drops such that it is within a second range of values (e.g., between approximately 0.50 and 0.75), the background colour of the maze 442 changes to yellow or orange. As a result, the visual contrast between the background colour of the maze 442 and the colour of the graphical line 444 decreases, making identification of a path to the maze exit and/or timely maze navigation more difficult. Finally, if the current value of the mind state alignment indicator MA(t) falls or drops such that it is within a third range of values (e.g., below approximately 0.50), the background colour of the maze 442 to a shade of red that approximately or closely matches the colour of the graphical line 444, making identification of a path to the maze exit and/or timely maze navigation even more difficult (e.g., very difficult).

Thus, successful and/or timely maze navigation is facilitated as the subject realizes and maintains mind state alignment indicator values $M_A(t)$ at or above a target training value. A mind state training exercise or game such as that described above can simultaneously train overall subject relaxation, attention, and analytical ability, as well as motor coordination associated with graphical line drawing in response to input device manipulation.

Figure 5B:
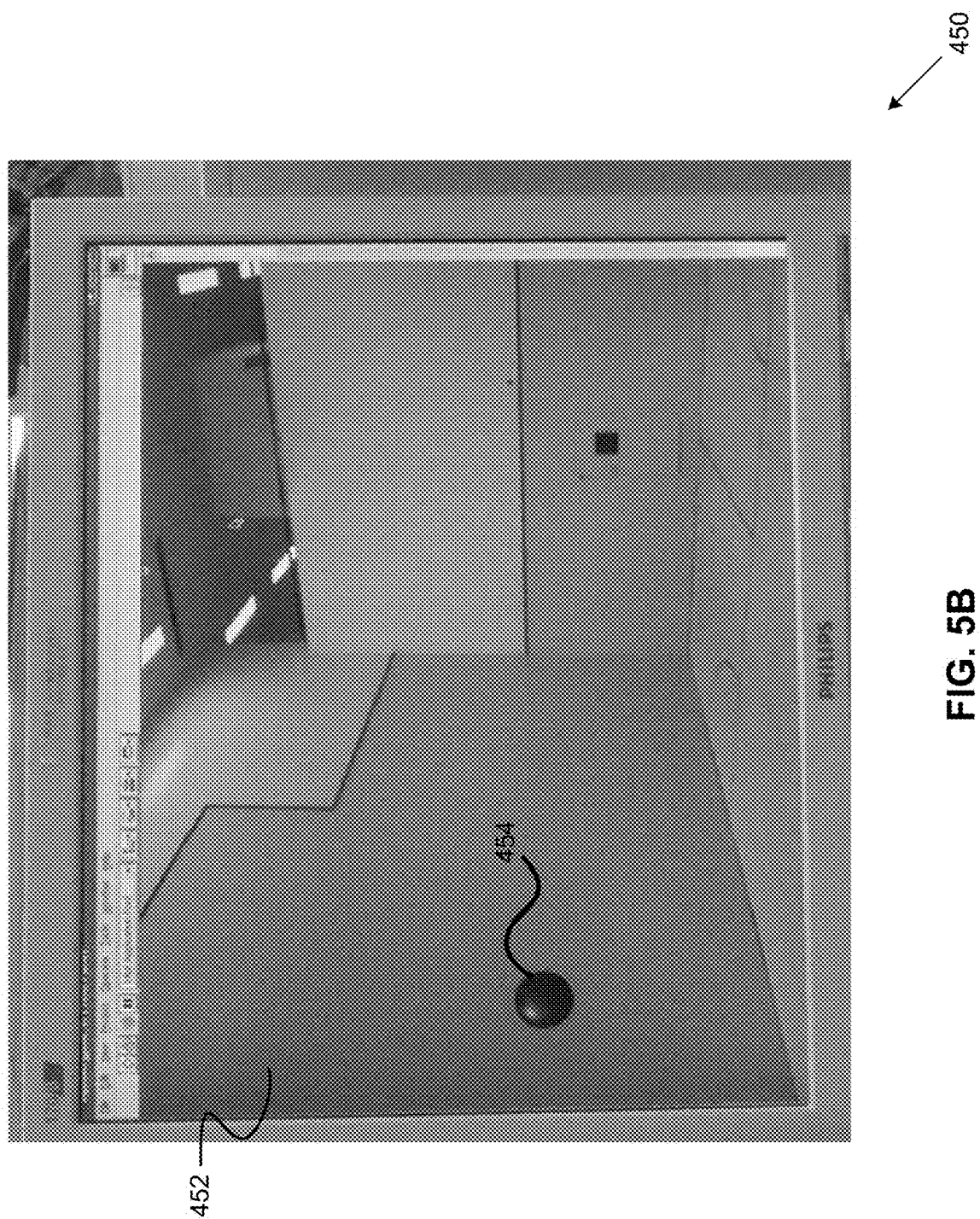

FIG. 5B depicts a representative second mind state training or exercise interface 450 according to an embodiment of the disclosure. In an embodiment, the second mind state exercise interface 450 includes a second visual or graphical mind state training game or exercise such as a ball game 452 in which motion parameters (e.g., speed of travel, or rate of acceleration following a bounce) corresponding to a graphical ball 454 are responsive to the current values of one or more mind state parameters. In a representative implementation, the speed of the ball 454 is inversely related to the value of a DAR measure. Thus, a lower DAR measure results in faster ball travel, and a higher DAR measure results in slower ball travel. The objective of the ball game 452 can be to control the speed of the ball such that the ball 454 moves as fast as possible, corresponding to the user maintaining current DAR values at or below a target training DAR value, which can be associated with increased alertness or less drowsiness. A reduced or low DAR value can be a natural outcome of relaxation training.

In various embodiments, one or more aspects of subject performance on mind state training routines, exercises, or games (e.g., game scores and/or completion times) are analyzed and/or stored (e.g., in a local or remote database 42, 82) as mind state training performance metrics. As a result, a subject history of mind state training performance can be generated, maintained, or accessed. As further described below, the system 10 can adaptively transition from the presentation of functional development activity sequences to mind state training routines, exercises, or games based upon the current value(s) of the subject's mind state indicator(s). When such a transition occurs, the system 10 can selectively present one or more mind state training routines, exercises, or games to the subject based upon the subject's known mind state training performance. More particularly, the system 10 can selectively present at least one mind state training routine, exercise, or game associated with (a) a highest or best expectation or likelihood of transitioning or restoring the subject's mind state to a target mind state that facilitates subject performance of functional development activity sequences, learning, or beneficial neural reorganization; and/or (b) a most rapid transition or restoration of the subject's mind state to such a target mind state.

Figure 6A:
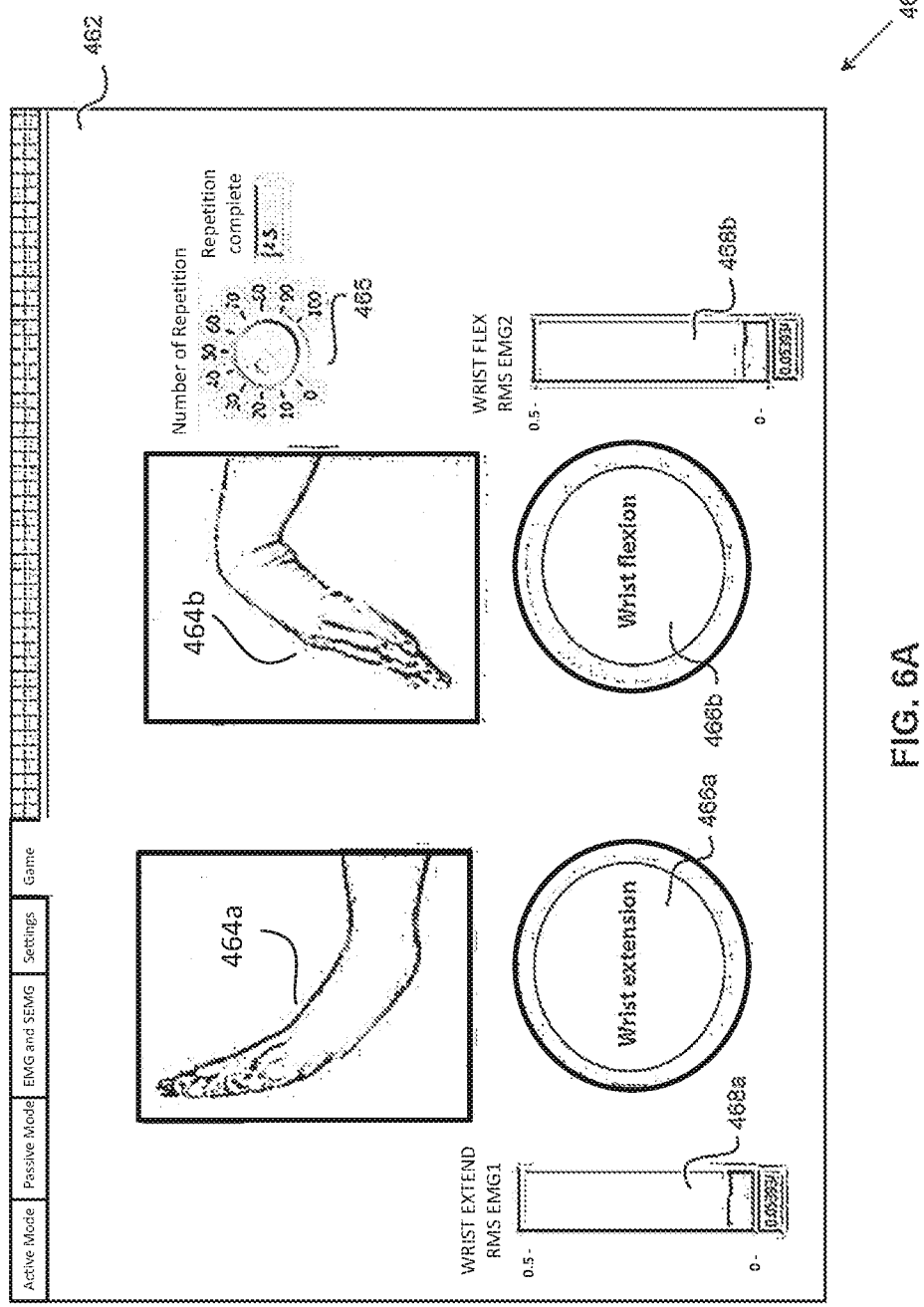
FIGS. 6A and 6B respectively depict a representative first body state training or exercise interface according to an embodiment of the disclosure and a representative second body state training or exercise interface according to an embodiment of the disclosure.

FIG. 6A depicts a representative first body state training or exercise interface 460 according to an embodiment of the disclosure. In an embodiment, the first body state exercise interface 460 includes a graphical window 462 in which a first body part action or exercise 464a and a second body part action or exercise 464b are visually presented to the user. The first and second body part exercises 464a-b can correspond to the extension and flexion of particular muscles (e.g., forearm or wrist muscles). A first and a second initiation trigger 466a-b such as graphical lamps can selectively provide a visual indication of when the subject is to initiate the first or second body part exercise 464a-b, and a first and a second graphical indicator element 468a-b can convey an extent of muscle activation (e.g., an EMG measure or signal level) to the subject. A graphical selector element or dial 465 facilitates selection or input (e.g., subject or clinician input) of a number of action or exercise repetitions.

After one of the initiation triggers 466a-b indicates that the subject is to perform or attempt to perform a corresponding body part action or exercise 464a-b, if the appropriate graphical indicator element 468a-b indicates a sub-optimal or inadequate amount of muscle activation when the subject performs or attempts to perform the body part action or exercise 464a-b, the subject may not be properly activating one or more muscles, or may be using a compensatory strategy for certain types or aspects of motion rather than a biomechanically correct strategy. Based upon visual information conveyed by the graphical indicator elements 468a-b, the subject can train the activation and control of particular muscles in a manner that facilitates the subject's performance of motions or movement sequences in a biomechanically correct manner.

Figure 6B:
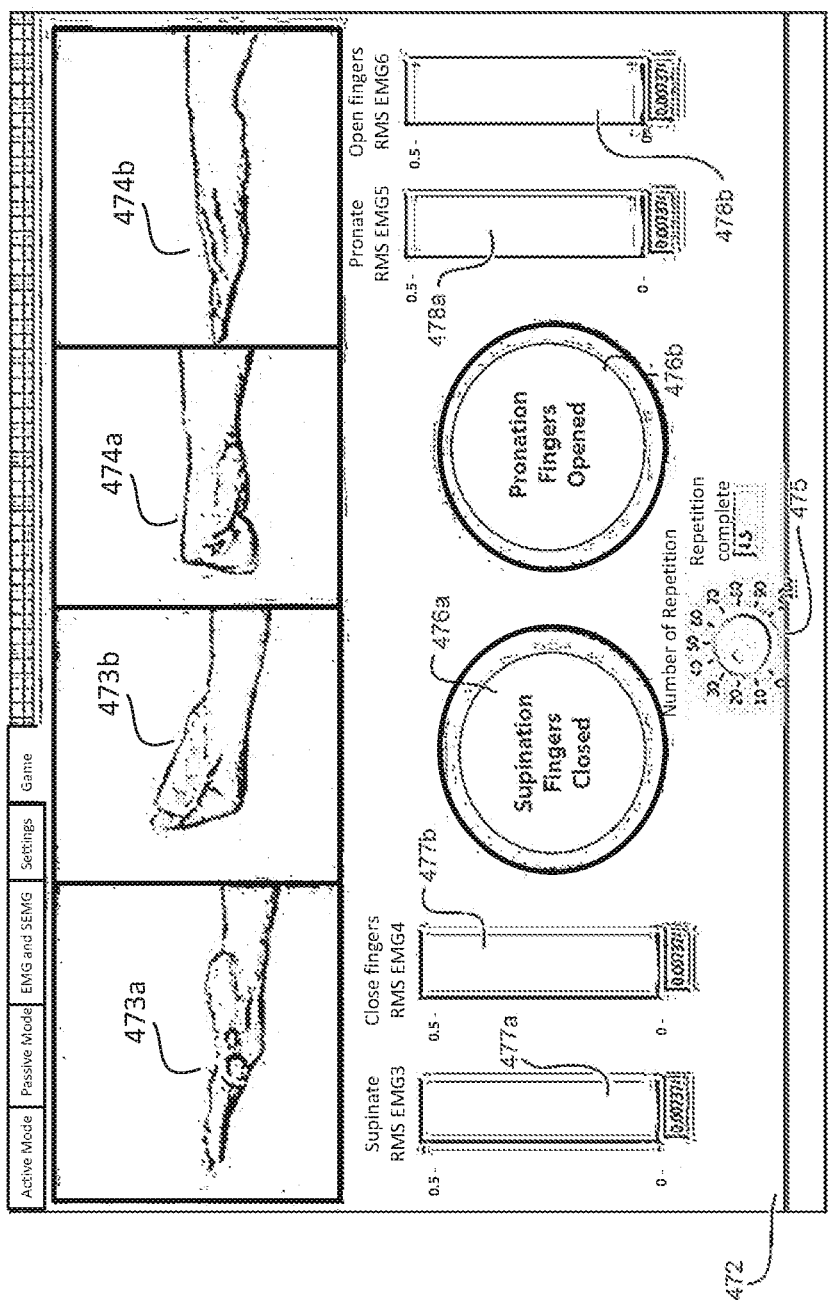

FIG. 6B depicts a representative second body state training or exercise interface 470 according to an embodiment of the disclosure. In an embodiment, the second body state exercise interface 470 includes a graphical window 472 in which a first muscle exercise sequence 473a-b (e.g., corresponding to a combined action of wrist supination and finger flexion) and a second muscle exercise sequence 474a-b (e.g., corresponding to a combined action of wrist pronation and finger extension) are presented to the subject. In a manner analogous to that described above, a first and a second activation trigger 476a-b (e.g., graphical lamps) can selectively indicate when the subject is to initiate the first muscle exercise sequence 473a-b and the second muscle exercise sequence 474a-b. A first set of graphical indicator elements 477a-b can convey an extent of muscle activation (e.g., EMG measures or signal levels) corresponding to the muscles involved in the first muscle exercise sequence 473a-b; and a second set of graphical indicator elements 478a-b can convey an extent of muscle activation (e.g., EMG measures or signal levels) corresponding to the muscles involved in the second muscle exercise sequence 474a-b. A graphical selector element or dial 475 facilitates selection or input of s number of action or exercise repetitions.

After the first or second initiation trigger 476a-b indicates that the subject is to perform or attempt to perform the first or second muscle activation sequence 473a-b, 474a-b, respectively, if the respective first set of graphical indicator elements 477a-b or second set of graphical indicator elements 478a-b indicates a sub-optimal or inadequate amount of muscle activation during subject engagement in the first or second muscle activation sequence 473a-b, 474a-b, the subject may be improperly activating one or more muscles, or may be using a compensatory strategy for certain aspects of motion rather than a biomechanically correct strategy. Based upon visual information conveyed by the first and second sets of graphical indicator elements 473a-b, 474a-b, the subject can train the activation and control of particular muscles in a manner that facilitates the subject's performance of motions or movement sequences in a biomechanically correct manner.

In various embodiments, one or more aspects of subject performance on body state training routines, exercises, or games (e.g., muscle activation measures or levels) are analyzed and/or stored (e.g., in a local or remote database 42, 82) as body state training performance metrics. As a result, a subject history of body state training performance can be generated, maintained, or accessed. As further described below, the system 10 can adaptively transition from the presentation of functional development activity sequences to body state training routines, exercises, or games based upon the current value(s) of the subject's body state indicator(s). When such a transition occurs, the system 10 can selectively present one or more body state training routines, exercises, or games to the subject based upon the subject's known body state training performance. More particularly, the system 10 can selectively present at least one body state training routine, exercise, or game associated with (a) a highest or best expectation or likelihood of transitioning or restoring the subject's body state to a target body state that facilitates subject performance of functional development activity sequences, learning, or beneficial neural reorganization; and/or (b) a most rapid transition or restoration of the subject's body state to such a target body state.

Aspects of Representative Adjunct Activity Promotion Devices

Various embodiments of the disclosure can include one or more types of adjunct apparatuses or devices 500 that can promote a subject's functional development, for instance, by aiding or assisting (e.g., on a selective or programmable basis) the subject's performance of functional development activity sequences. Such adjunct activity promotion devices can include robotic devices, and/or extrinsic signal application devices (e.g., configured to delivery functional electrical stimulation (FES), transcranial magnetic stimulation (TMS), transcranial direct stimulation (tDCS), or other types of electromagnetic signals to the subject 5).

In multiple embodiments, a body signal capture device 200 can include a number of electrodes configured to selectively apply electrical stimulation signals, such as Functional Electrical Stimulation (FES) signals, to particular subject muscles or muscle groups. In some embodiments, the electrical stimulation signals can be applied or delivered by way of EMG electrodes 210 that the body signal capture device 200 carries. Such a body signal capture device 200 can capture or acquire EMG signals at particular times, and selectively apply electrical stimulation signals at other times, for instance, in order to assist the subject in performing one or more types of tasks corresponding to a functional development activity sequence.

Figure 7A:
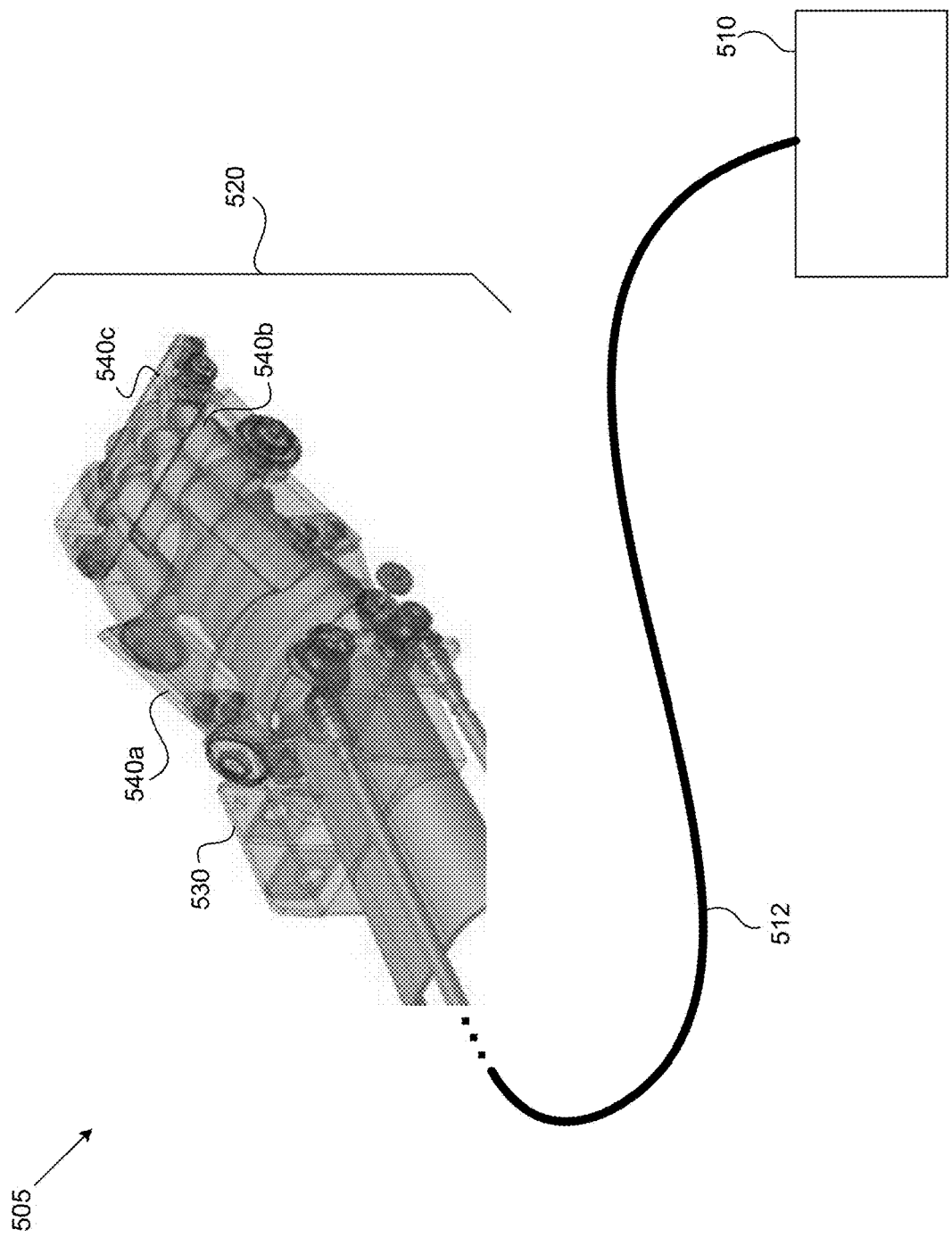
FIG. 7A is a schematic illustration of a representative robotic orthosis system, subsystem, or apparatus according to an embodiment of the disclosure.

FIG. 7A is a schematic illustration of a representative robotic orthosis system, subsystem, or apparatus 505 according to an embodiment of the disclosure, which can at least partially guide and/or assist a subject's performance of particular types of motions or movement sequences or patterns in a manner that is complementary or synergistic with respect to the subject's development or restoration of (a) volitionally selective muscle activation and relaxation abilities; and (b) reliable or smooth control of compound, complex, or intricate movements for a subject appendage under consideration.

The orthosis system 505 includes at least one motor, actuator, and/or drive assembly or mechanism 510 (hereafter motor) that is coupled to a subject wearable orthosis 520. In various embodiments, the wearable orthosis 520 excludes or is separate from the motor 510. That is, the wearable orthosis 520 need not carry and can omit or exclude the motor 510, which can be located separate or remote from the wearable orthosis 520. In several embodiments, the motor 510 can be separate or remote from the subject (e.g., positioned on a floor, table, or cart), or carried by a support device that can be worn on portion of the subject's body (e.g., a portion of the subject's waist or hips) that is distinct or separate from a bodily location (e.g., corresponding to portions of the subject's forearm, wrist, and/or hand) at which the wearable orthosis 520 is positioned. In multiple embodiments, the motor 510 and the wearable orthosis 520 are mechanically coupled by way of one or more flexible drive shafts 512 that are configured to transfer or deliver mechanical power (e.g., as a result of first rotational motion in a first direction, and second rotational motion in a second direction) provided by the motor 510 to the wearable orthosis 520, as further detailed below.

Various embodiments of the wearable orthosis 520 exhibit a modular design or construction that facilitates or enables ease of orthosis assembly and disassembly, and/or the selective inclusion or omission of particular orthosis modules, components, or elements based upon one or both of the subject's current functional state and the subject's progress in developing or restoring functional capabilities. As an extent or measure of the subject's functional capabilities increases or improves with time, particular modules, components, or elements can be removed or excluded from the wearable orthosis 520. As a result, an amount of additional weight that a subject appendage bears due to the presence of the wearable orthosis 520 can decrease over time, for instance, as the subject becomes progressively more proficient at certain types of activities, tasks, or motions.

The wearable orthosis 520 is typically intended to be carried by or worn on portions of a subject appendage or body part on which a body signal capture device 220 such as a wearable sleeve 220 that carries EMG electrodes 210 is worn. In certain embodiments, portions of the wearable orthosis 520 can apply or deliver one or more types of electrical stimulation signals (e.g., FES signals) to particular subject muscles.

In an embodiment, the wearable orthosis 520 includes a mechanical power interface module 530 coupled to one or more appendage motion modules 540a-c. The mechanical power interface module 530 is configured to couple to or receive at least one flexible drive shaft 512, and includes a number of mechanical power provision and/or conversion elements such as gears or gear mechanisms configured to apply or deliver mechanical power, force, and/or torque provided by a flexible drive shaft 512 to portions of particular appendage motion modules 524a-c. In various embodiments, the power provision and/or conversion elements are configured to convert rotational motion, force, power, or torque supplied by the flexible drive shaft(s) 512 into linear motion, force, or power that selectively controls the motion or displacement of appendage motion modules 540a-c relative to the power interface module 530 and/or each other.

The use of flexible shafts 512 also makes it possible to quickly decouple/couple one or more the motors 570 from the drive system for certain tasks or individuals. Without the motors 570 attached, it can also be used as an orthosis running solely on FES or muscular effort. This makes the design versatile not only for individual cases, but also enables continued use by the same patient through the various stages of recovery in a modular manner.

Specific aspects of a representative implementation of a wearable orthosis 510 directed to facilitating a subject's maintenance, development, rehabilitation, or restoration of hand, wrist, and/or forearm motion (e.g., in association with stroke rehabilitation therapy) in accordance with an embodiment of the disclosure are described in detail hereafter.

In an embodiment, the major composition of the materials used for in the construction of the orthosis is cast nylon. In other embodiments, the major composition of the materials used in the construction of the orthosis is at least one of cast nylon, acrylic and delrin. The materials used in the composition of rods, shafts and set screws can include stainless steel. Circlips, which can be used in the construction of the orthosis, can include carbon steel spring. The orthosis can also include bushes which can be made of brass or polytetrafluoroethylene. The bevel gears in the orthosis can be made of brass.

Figure 7B:
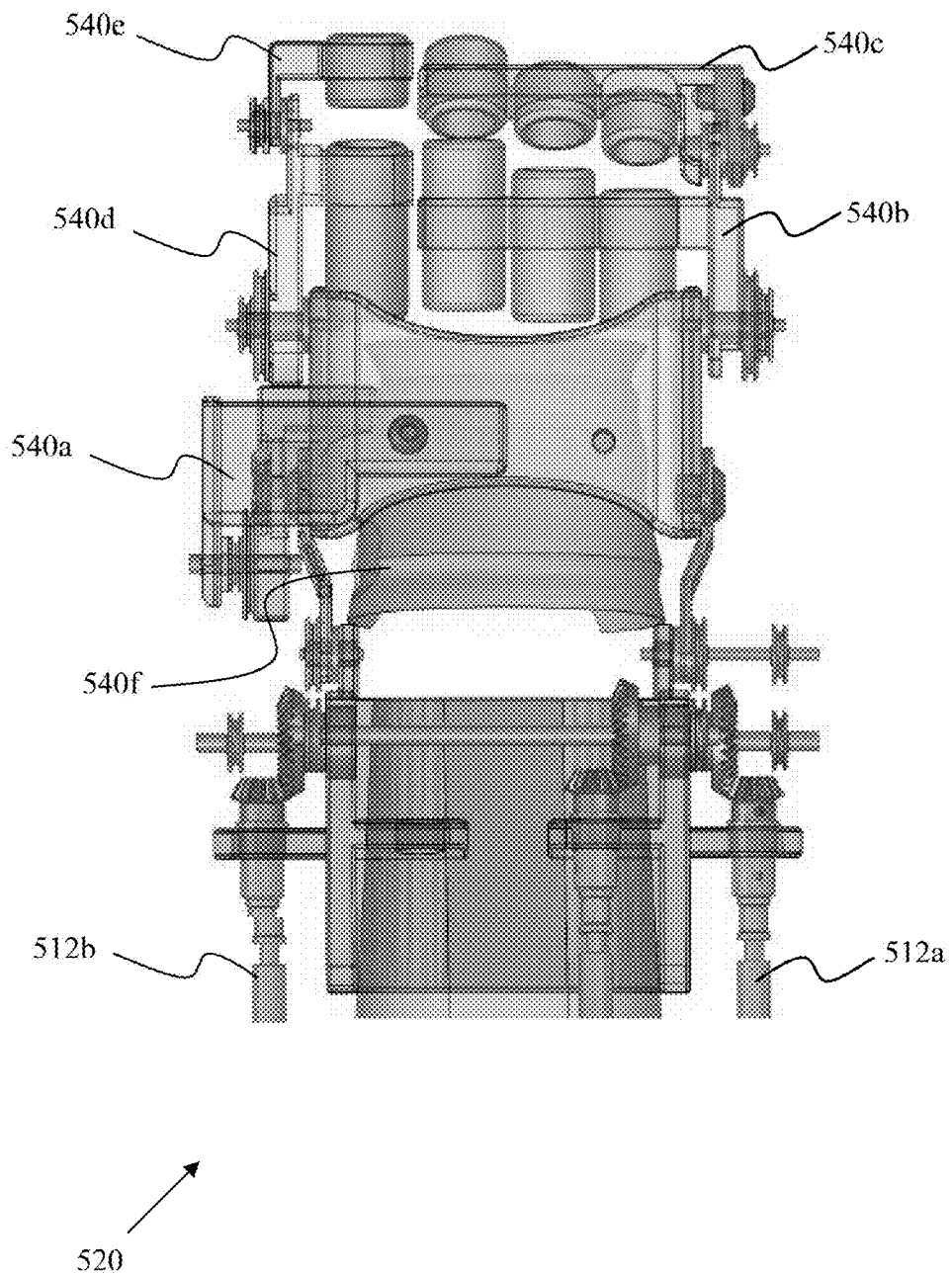
FIG. 7B shows an embodiment of a modular orthosis according to an embodiment of the present disclosure.

FIG. 7B shows an embodiment of a modular orthosis 520 according to an embodiment of the present disclosure, in which the various modules can be detached (e.g., if the particular patient has no use for it). It is reasonable to expect that initially, the patient will need to use all the parts to support various movements. As he or she improves, one or more joints may no longer need robotic assistance. At this stage it is important to reduce orthosis weight so that finer and finer movements become possible for the patient, and fatigue and imbalance due to orthosis weight is minimized. The modules 520 can be removed, for instance, starting from distal appendages. For example, the movement of the proximal interphalangeal joint (PIP) can be disabled by removing the modules 540b and 540d attached to the PIP, but in several embodiments if the module 540a responsible for the palmer abduction is removed, the movement of the PIP and the metacarpophalangeal joint (MCP) is immediately ruled out due to the design of the pulley and cable system. For the rotation of the MCP/PIP rotation middle, ring, and last finger, the modules 540d, 540e can be removed from distal downwards, but not from the wrist up, similar to the previous mechanism.

Figure 7C:
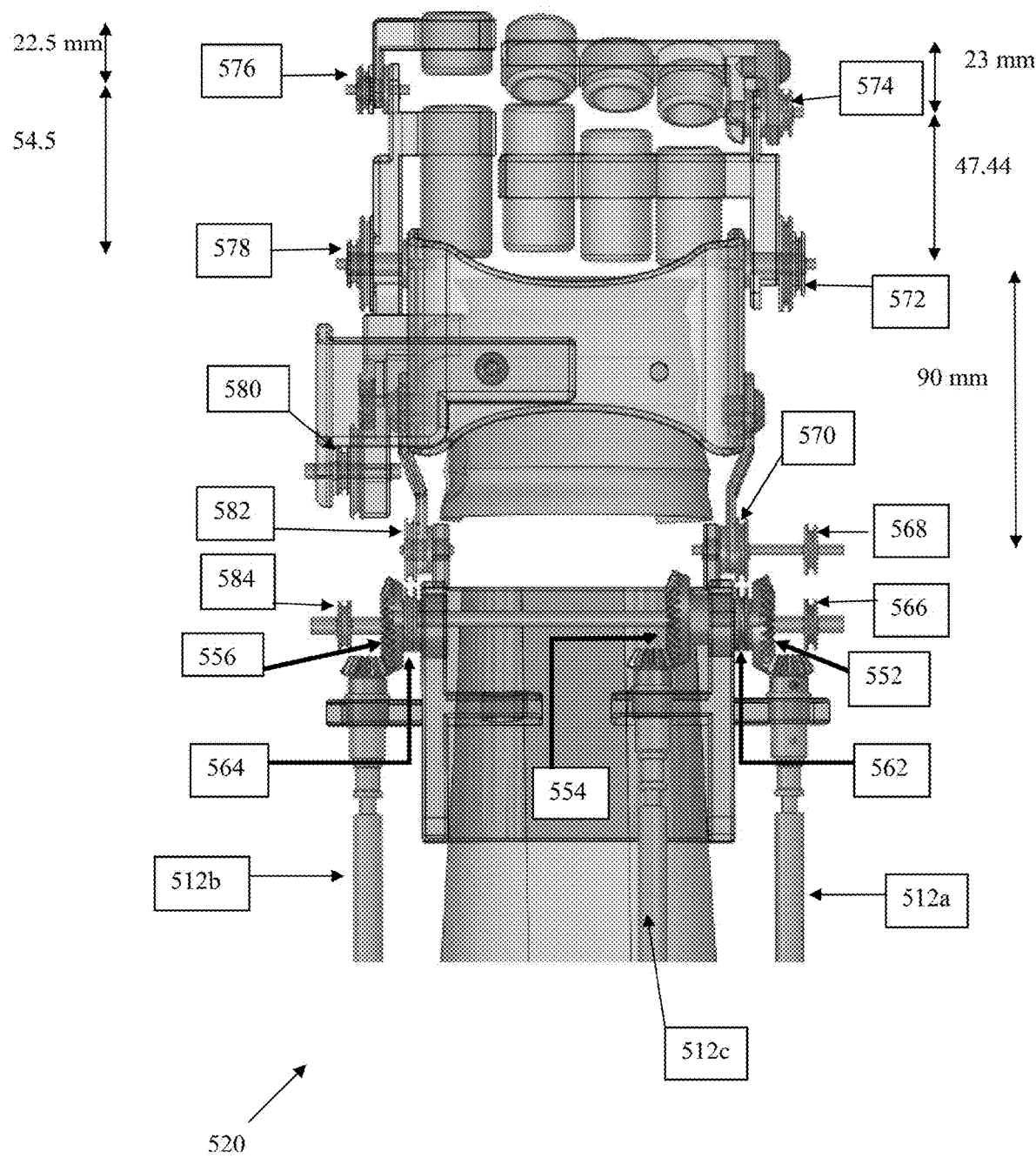
FIG. 7C is an embodiment of the orthosis of FIG. 7B, which identifies aspects of the orthosis.

FIG. 7C is an embodiment of the orthosis 520 of FIG. 7B, which identifies aspects of the orthosis 520 relevant for specific mechanical manipulation of the subject's hand, wrist, and/or forearm motion for facilitating the subject's maintenance, development, rehabilitation and restoration of such parts, as described in detail hereafter.

Rotation

The rotation of the fingers and wrist about their joints are based on certain prehension patterns, mainly the pinch and the cylindrical grasp.

Wrist Flexion and Extension

The drive to enable wrist flexion and extension are transmitted via the flexible shaft 512c to bevel gear 2 (554). As bevel gear 2 (554) rotates, pulley 1a (562) will rotate.

Pulley 1b (564) will rotate as well, as it is affixed to the same shaft. Both these pulleys are coupled to pulley 4 (570) and pulley 10 (582) respectively. This enables the wrist flexion and extension.

Flexion and Extension of Fingers (Middle, Ring and Last)

The main drive will be transmitted to pulleys 2 (566), 3 (568), 5 (572) and 6 (574) from bevel gear 1 (552). Bevel gear 1 (552) will rotate, and pulley 2 (566) will rotate with it. The cable is wound around pulley 2 (566) to pulley 3 (568), where it is wound around and extended to pulley 5 (572). As pulley 5 (572) rotates, the movement of the MCP will be enabled. A cable will be wound around the larger pulley of pulley 5 (572) to pulley 6 (574). Hence, as pulley 5 (572) rotates, pulley 6 (574) will rotate, and the movement of the PIP is enabled.

Palmar Abduction/Flexion and Extension of Index Finger

The rotation of bevel gear 3 (556) is responsible for the palmer abduction and the extension and flexion of the index finger. As bevel gear 3 (556) rotates, pulley 11 (584) rotates as well. A cable is wound from pulley 11 (584) to pulley 9 (580). The rotation of pulley 11 584 will result in the rotation of pulley 9 (580), which enables palmer abduction. A cable is wound from the larger pulley of pulley 9 (580), and it is connected to the smaller pulley of pulley 8 (578). The rotation of pulley 8 (578) will enable the rotation of the index finger MCP. The larger pulley of pulley 8 (578) will be connected to pulley 7 (576), and the rotation of pulley 7 (576) will enable the movement of the PIP of the index finger.

Extension and Flexion of the Thumb

Figure 7D:
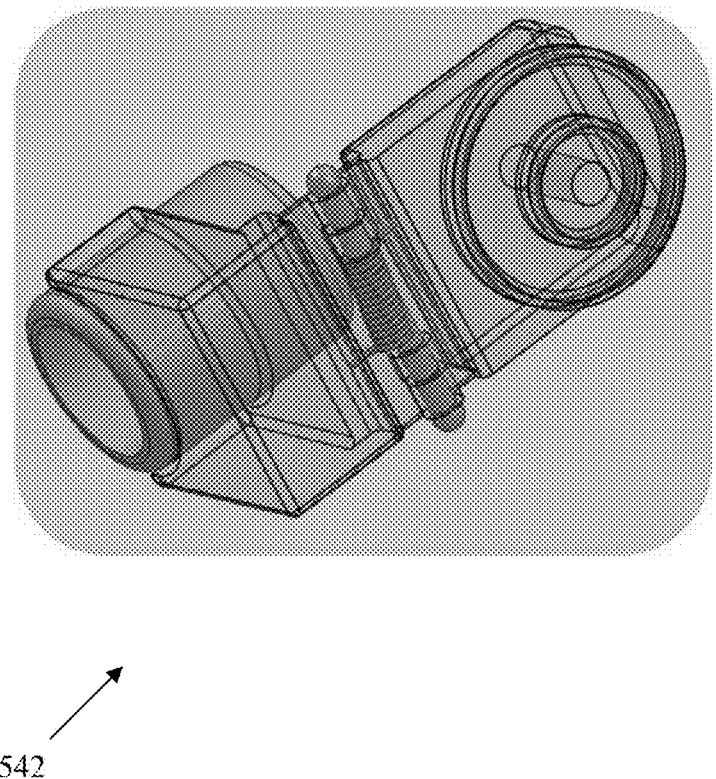
FIG. 7D shows a schematic illustration of a torsion spring for the thumb.

FIG. 7D shows a schematic illustration of a torsion spring 542 for the thumb. The hand orthosis was not designed to provide extension and flexion of the thumb MCP. Instead, it will allow voluntary extension and flexion of the thumb via a light torsion spring which will keep the thumb MCP in a slightly flexed or neutral position. Any extension will have to be voluntarily executed. In some cases, the setting can be kept in a "normally extended" position so that the subject will have to voluntarily flex it. This feature can be useful in some pinch and grasp variations like pinching between the thumb and the index finger or executing a three-finger pinch.

The orthosis allows for 12 degrees of freedom (DOF) of hand motion. The DOF for each of the major parts of the orthosis are as follows: 3 DOF for each of modules 540b and 540c; 1 DOF for each of modules 540e, 540d and 540a; and 1 DOF for each of the rotation of the wrist, and rotation for the supination and pronation of the forearm.

Motor Sizing and Selection

The motors can be chosen for the three main drives to bevel gears 1 552, 2 554 and 3 556 according to a maximum torque which can be applied to contracture joints as shown in Table 1. They have been established by Japanese researchers who collaborated with therapists to develop a robotic hand which simulated actual hand forces (Mouri, et al., 2007).

TABLE 1

Torques needed for the various joints in the human hand (Mouri, et al., 2007)

|  | Thumb (Nm) | Fingers (Nm) | Wrist (Nm) |
| --- | --- | --- | --- |
| 1st | 0.33 | 0.17 | 1.3 |
| 2nd | 0.29 | 0.29 | 3.0 |
| 3rd | 0.26 | 0.29 |  |
| 4th | 0.25 | 0.20 |  |

Referring to the above table, the values in relation to the $2^{nd}$ and $3^{rd}$ joints of the fingers represent the torque needed for the movement of the MCP and PIP of the fingers.

The value in relation to the $2^{nd}$ joint of the thumb represents the torque needed for the movement of palmer abduction. The value in relation to the $2^{nd}$ joint of the wrist, represents the torque needed for flexion and extension of the wrist.

Disregarding external forces such as frictional forces, the torques needed for the three motors are shown in Table 2.

TABLE 2

Required torques for transmission at output shaft of motors

|  | Torque (Nm) |
| --- | --- |
| Bevel Gear 1 | 1.1105 |
| Bevel Gear 2 | 1.3680 |
| Bevel Gear 3 | 1.4409 |

Considering possible external forces such as frictional forces and resistance from the patient especially if deformities and finger and wrist contractures are present, the motors that can provide 1.5-2.5 Nm of torque are selected.

Forearm Orthosis

Figure 7E:
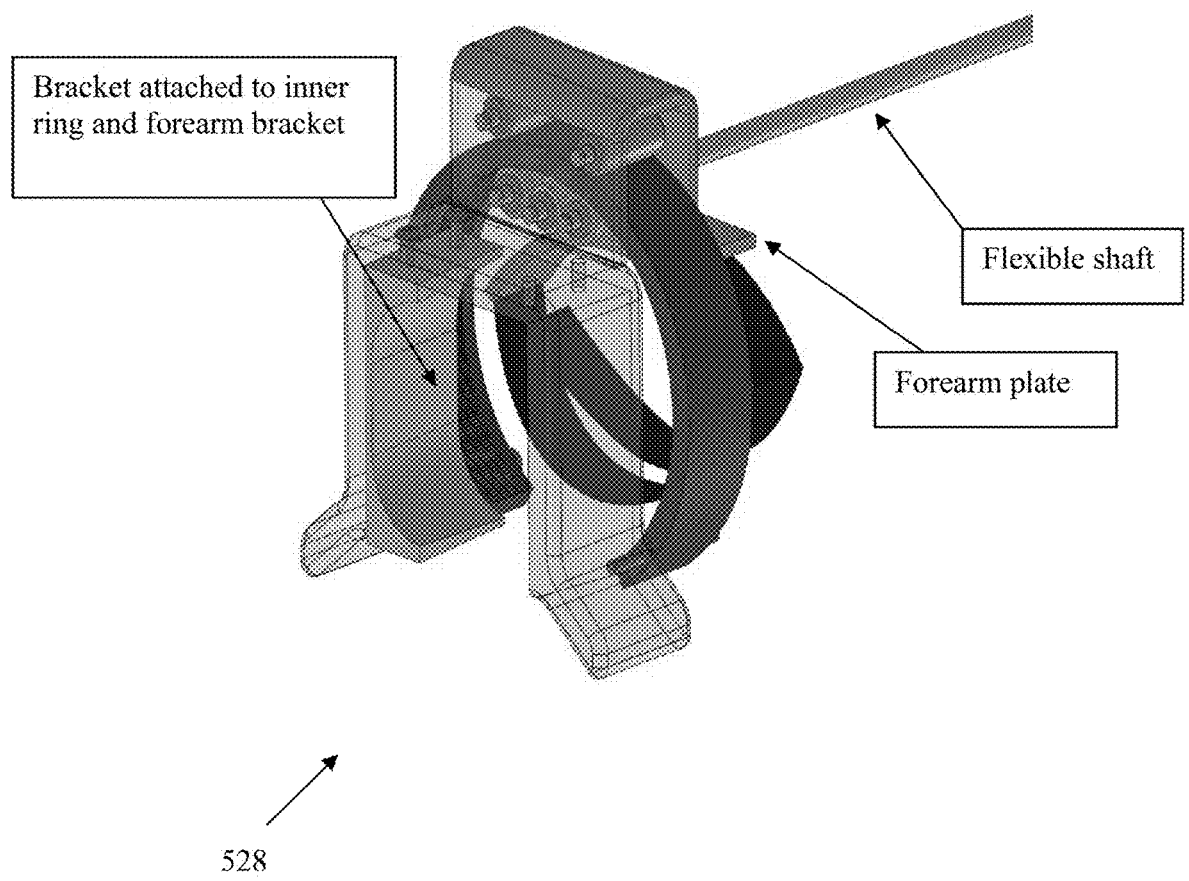
FIG. 7E shows a forearm orthosis according to an embodiment of the present disclosure.

FIG. 7E shows a forearm orthosis 528 according to an embodiment of the present disclosure. In an embodiment, a separate forearm orthosis 528 can be incorporated with the hand orthosis 520 for use together with the hand orthosis 520 whenever required by the subject. The aim of the forearm orthosis 528 is to provide the motion for supination and pronation of the arm. The forearm plate can be strapped to the upper forearm, while a forearm bracket of the hand orthosis 520 can be rotated as the semicircular gear rotates, thereby providing the motion of supination and pronation. Whenever necessary, an additional support can be provided at the upper arm through a hinged arrangement.

To attach the forearm orthosis 528 to the hand orthosis 520, a bracket can be attached to the forearm cast, and then attached to the inner ring from the top. A spring loaded mechanism further can enable the forearm bracket and the bracket for the inner ring to be locked in place The forearm orthosis 528 includes a semi-circular internal ring gear which is driven by a pinion actuated by motors, and with power transmitted via a flexible shaft. In a representative implementation, a driving gear in the forearm orthosis has 25 teeth, module of 1 and the semi-circular gear has 100 teeth, module of 1, at its full circular circumference. The torque needed is approximately twice that necessary for the flexion and extension of the wrist. Hence, a torque of about 2.736 Nm is in consideration. The motor is accordingly selected. With a gear ratio of 1:4, the torque transmitted to the semi-circular gear would be multiplied by 4.

Figure 7F:
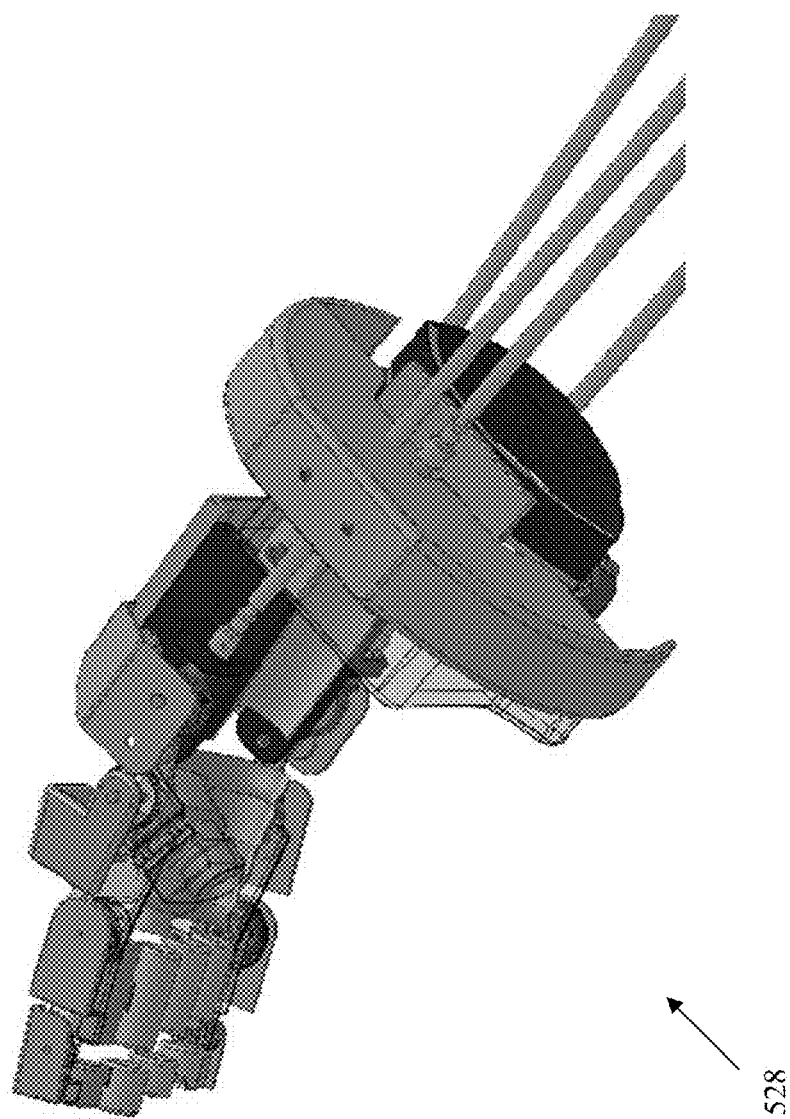
FIGS. 7F and 7G are schematic illustrations of representative embodiments of a hand-wrist-forearm orthosis in accordance with an embodiment of the present disclosure.
Figure 7G:
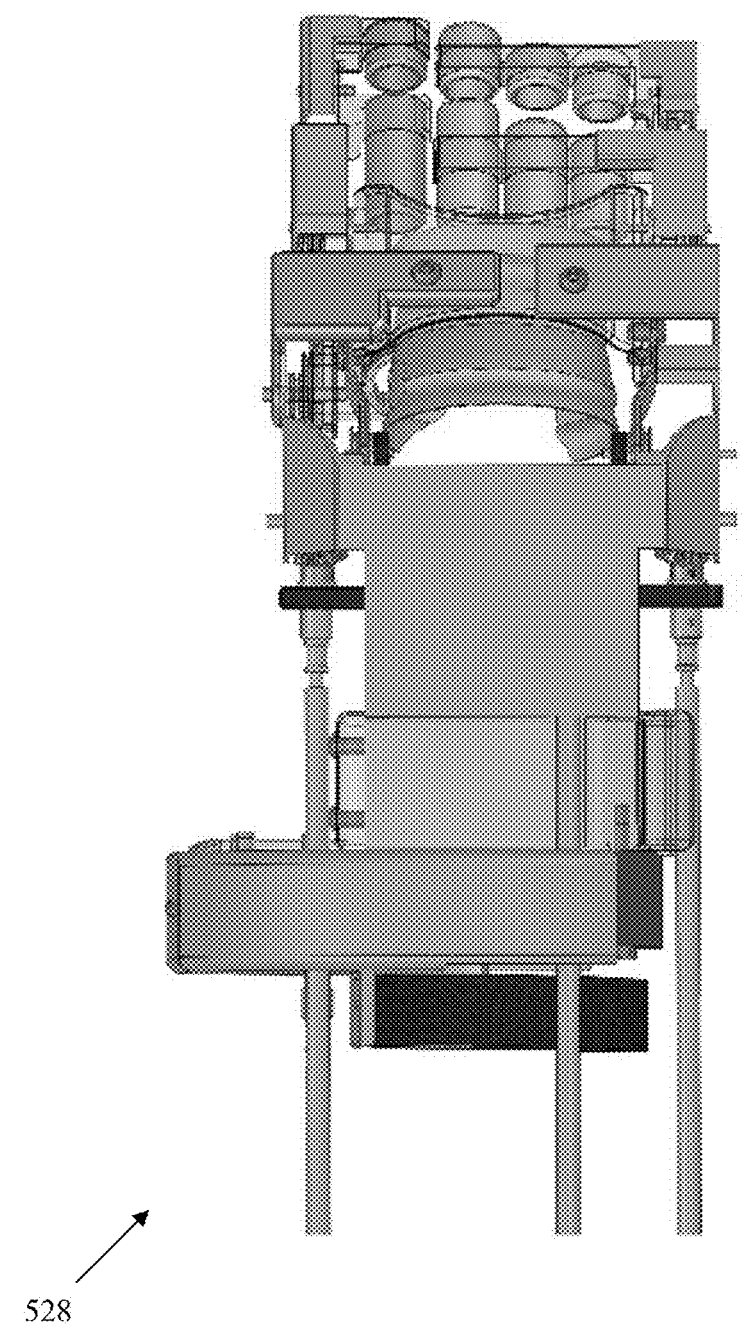

In view of or association with the foregoing, FIGS. 7F and 7G are schematic illustrations of representative embodiments of a hand-wrist-forearm orthosis 528 in accordance with an embodiment of the present disclosure.

In certain embodiments, the wearable orthosis 510 can carry or include one or more mechanical energy storage elements (e.g., spring or spring based elements) configured to selectively store and release mechanical energy in a manner that balances an amount of power, force, or torque provided by a flexible drive shaft 512 relative to a first direction of drive shaft rotation and a second direction of flexible drive shaft rotation. In specific embodiments, portions of the wearable orthosis 510 can carry or include one or more motors or actuators.

In various embodiments, in response to the detection of the activation of a particular muscle that results in a muscle activation measure or signal level (e.g., an EMG measure or signal level) which equals or exceeds a threshold measure or signal level, (e.g., corresponding to a volitional muscle contraction that generates an EMG measure or signal level above a threshold value, for instance, a volitional muscle contraction that results in the generation of an RVC signal), a portion of the system 10 such as an adjunct signal module 782 generates a set of motor control signals corresponding to the activated muscle. In some embodiments, a given muscle activation signal can be associated with one or more motor control signals by way of a set of muscle activation-motor control signal mappings, which can be stored in a data structure (e.g., a table) within the memory 700 or a local or remote database 42, 82.

Following the detection of muscle activation, motor control signals are communicated to the motor 510, which provides or delivers an appropriate amount of power, force, or torque to the mechanical power interface module 530 by way of one or more flexible drive shafts 512. Mechanical power, force, or torque is subsequently delivered or applied to portions of one or more appendage motion modules 540a-c, such that the wearable orthosis 510 carries or moves a subject body part corresponding to the activated muscle under consideration through a particular range of motion. A range of motion associated with a particular body part can be indicated by a predetermined, selectable, or programmably specified range of motion parameter.

When the subject is engaged in an action or task within a functional development activity sequence or a body state training exercise, in the event that the subject activates an incorrect muscle that would hinder or prevent successful activity or task performance, motor control signals corresponding to the incorrect muscle can be generated and communicated to the motor 510 in a manner analogous to that described above. The wearable orthosis 520 can subsequently carry or move a subject body part corresponding to the activation of the incorrect muscle along a path or in a direction that clearly indicates to the subject that their current muscle activation is incorrect and leads away from or will not result in successful performance of the activity or task. The subject can refer to a biofeedback interface 400 that provides visual biofeedback regarding current or recent muscle activation in order to recognize the reason underlying such poor or unsuccessful activity or task performance, and the subject can attempt to self-correct their muscle activation based upon such biofeedback in order to learn how to activate an appropriate, biomechanically correct muscle in order to successfully perform the activity or task under consideration.

In some embodiments, the robotic orthosis system 505 can additionally act as a passive motion system that carries or moves particular patient body parts through certain ranges of motion, for instance, as part of a warm-up routine, or in the event that the subject is unable to follow instructions (e.g., as a result of cognitive impairment) at a particular time.

Aspects of Adjunct Mind Signal and Body Signal Capture Devices

Some embodiments of the disclosure can include an adjunct mind signal and body signal capture apparatus or device 600 configured to capture mind signals and body signals apart from the subject's performance or attempted performance of functional development activity sequences, during the subject's performance or attempted performance of normal or desired day-to-day activities.

Figure 8A:
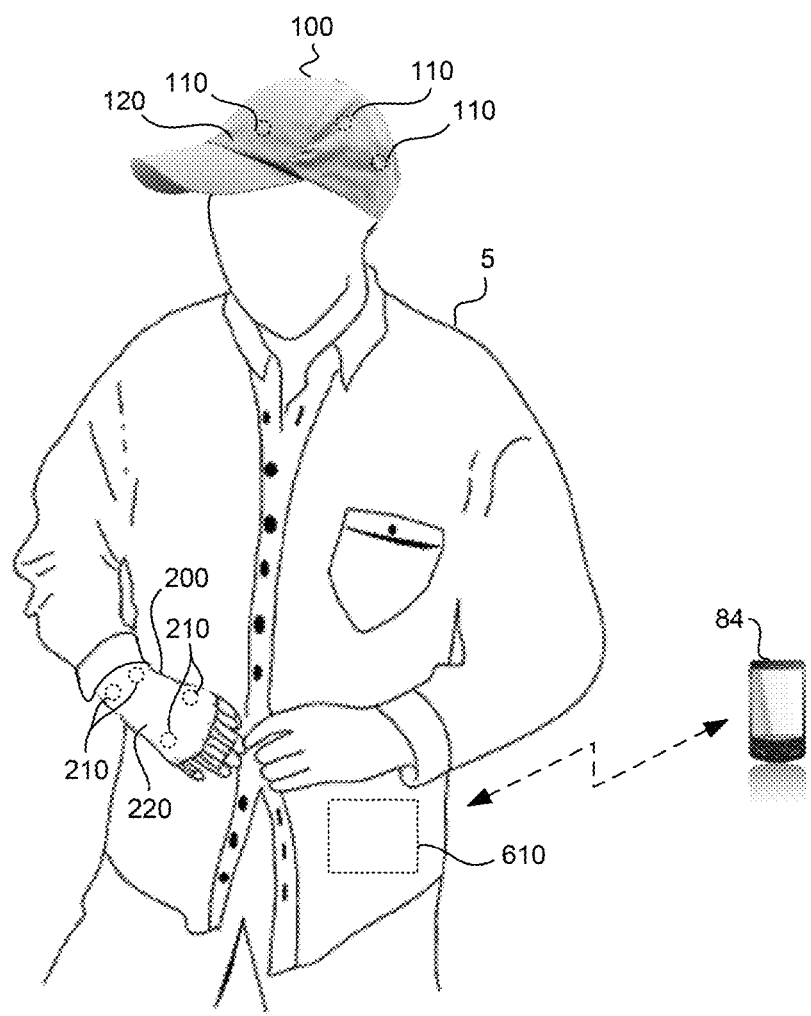
FIG. 8A is a schematic illustration of a representative portable mind signal/body signal capture apparatus or device according to an embodiment of the disclosure which can be worn, supported, or carried by a subject.

FIG. 8A is a schematic illustration of a representative portable mind signal/body signal capture system, subsystem, or apparatus 605 according to an embodiment of the disclosure that includes a portable mind signal/body signal capture device 610 that can be worn, supported, or carried by a subject 5. In an embodiment, the portable mind signal/body signal capture device 610 is a subject wearable device that is configured for wire based or wireless signal transfer with a mind signal capture device 100 and a body signal capture device 200. More particularly, the portable mind signal/body signal capture device 610 is configured to capture, store, monitor, and/or analyze mind signals and body signals during one or more time intervals within which the subject 5 performs or attempts to perform normal daily activities.

The portable mind signal/body signal capture device 610 is further configured for wire based and/or wireless transfer of captured mind signals and body signals, and possibly processed signals corresponding thereto (e.g., particular mind state indicators and body state indicators, and/or mind state maintenance scores and body state maintenance scores) to a system 10 for unified neurological-physiological rehabilitation and/or function development according to an embodiment of the disclosure. A portable mind signal/body signal capture device 610 can further be configured for wire based and/or wireless transfer of captured mind signals, captured body signals, mind state indicators, body state indicators to another type of remote or external device 84, such as a mobile telephone or a tablet or laptop computer. Such a remote or external device 84 can be configured to provide a biofeedback interface (e.g., which presents visual biofeedback information on a real time, near-real time, and/or delayed basis), such that the subject 5 or another individual can monitor or assess an extent to which the subject 5 has maintained their mind state and body state in alignment with an enhanced likelihood of normal activity performance, learning, or favorable neural reorganization.

Figure 8B:
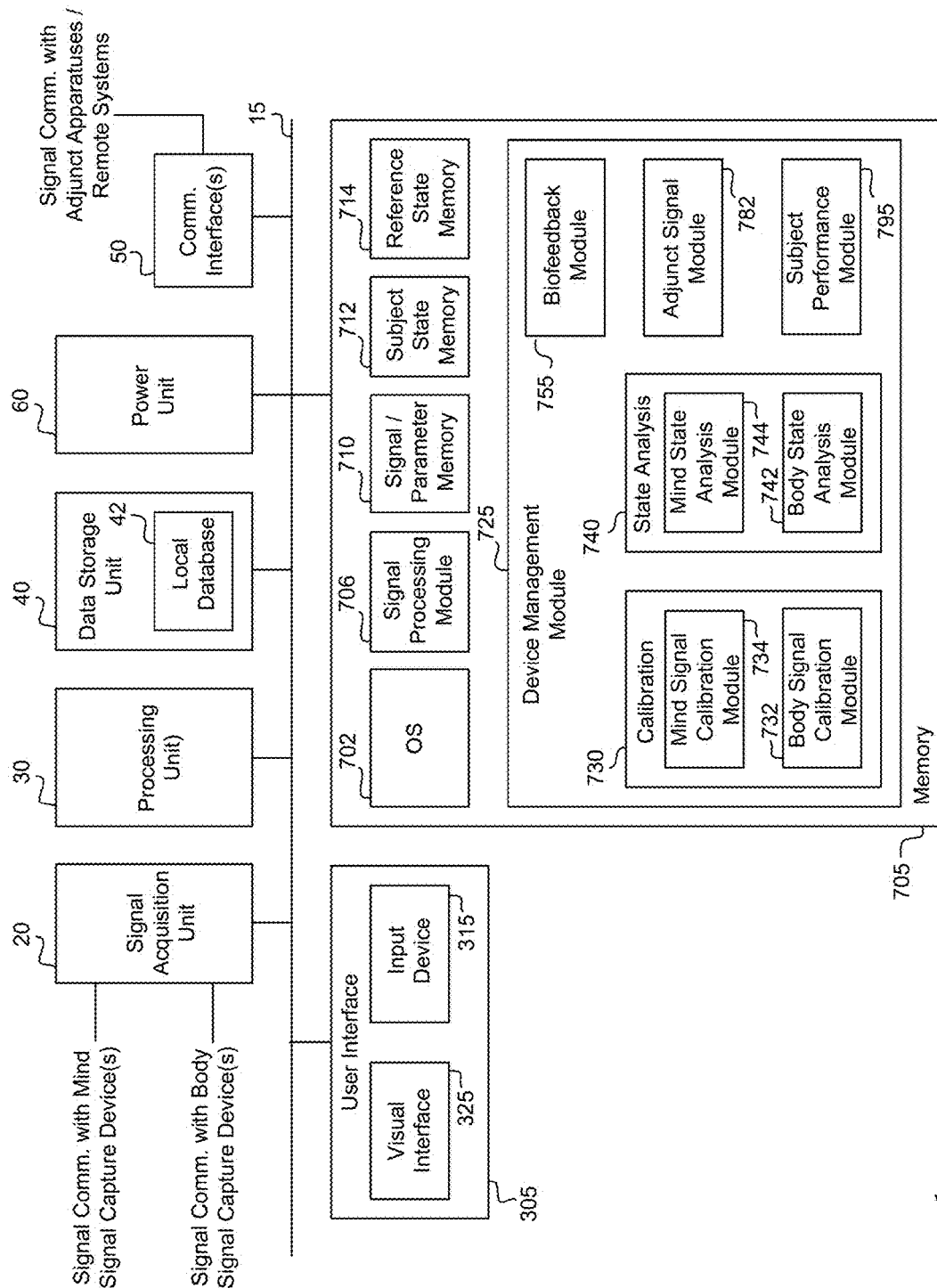
FIG. 8B is a block diagram of a portable mind signal/body signal capture apparatus or device according to an embodiment of the disclosure.

FIG. 8B is a block diagram of a portable or wearable mind signal/body signal capture device 610 according to an embodiment of the disclosure. In an embodiment, the portable mind signal/body signal capture device 610 includes a signal acquisition unit 20 that is configured for signal communication with a set of mind signal capture apparatuses or devices 100 and a set of body signal capture apparatuses or devices 200; a processing unit 30; a data storage unit 40 that can include a local database 42; a communication interface 50 that is configured for signal communication with one or more external or remote systems, apparatuses, or devices; a power unit 70 that includes a set of batteries (e.g., a rechargeable battery) and possibly power management circuitry; a user interface 305 configured to receive and respond to user input (e.g., subject and/or clinician input), which can provide a visual interface 325 (e.g., which includes a display device such as an LCD or LED based display) and/or an audio interface to facilitate operation of or subject interaction with the portable mind signal/body signal capture device 610; and a memory 705 in which program instructions, signals, and/or data reside that facilitate or enable the capture, processing, and/or analysis of mind signals and body signals while the subject engages in or attempts to engage in day to day activities such as activities of daily living, as further described in detail below. Particular elements of the portable mind signal/body signal capture device 610 can be coupled to a set of common or shared signal distribution, transfer, or communication pathways 15, such a set of buses.

One of more portions of the portable mind signal/body signal capture device 610 can have a structure and/or function that is identical, essentially identical, analogous, or generally analogous to a portion of an embodiment of a system or platform 10 for unified neurological-physiological rehabilitation, functional development, and/or functional maintenance such as that described above with respect to FIG. 1. The communication interface 50 can be configured for signal communication with (a) one or more remote systems (e.g., a neuro-physio platform 10 designed in accordance with an embodiment of the disclosure, or a computer system or computing device coupled to a networked computing infrastructure 90 such as a LAN or the Internet); and possibly (b) a set of adjunct activity promotion apparatuses 500, such as an electrical stimulation (e.g., FES) apparatus. Additionally, the user interface 305 can include a an input device such as a keypad or a set of buttons, or a proximity or touch based interface, such as a touch responsive or touch sensitive display device (e.g., a proximity, touch, or pressure responsive LCD display).

In an embodiment, the memory 705 includes at least some of an operating system 702, a signal processing module 706, a signal parameter memory 710, a subject state memory 712, a reference state memory 714, and a device management module 725. The device management module 725 includes a set of program instructions configured to manage or control aspects of portable mind signal/body signal capture device operation. The device management module 725 can include one or more of a calibration module 730, a subject state analysis module 740, a biofeedback module 755, an adjunct signal generation module 782, and a subject performance module 795.

In various embodiments, the portable mind signal/body signal capture device 610 can be configured to capture, filter, perform particular types of processing operations upon, and locally store (e.g., within the memory 705 and/or upon the data storage unit 40) mind signals and body signals. Raw, filtered, and/or processed mind signals and body signals can be locally stored at particular times, such as at predetermined, selectable, or programmably specified time intervals, or time intervals which can vary depending upon whether an RVC has been detected (e.g., in order to reduce or minimize an amount of mind signal related or body signal related data that is locally stored). In certain embodiments, the portable mind signal/body signal capture device 610 determines or generates and/or analyzes one or more mind state indicators, body state indicators, and possibly mind-body synergy indices, indicators, or measures. Additionally or alternatively, certain mind state indicators and/or body state indicators can be generated or analyzed remote from the portable mind signal/body signal capture device 610, for instance, by a remote computer system following the communication or transfer of mind signal related data values and body signal related data values thereto (e.g., in a post-processing or offline mode that is concurrent with mind signal and body signal capture by the portable mind signal/body signal capture device 610).

Multiple portable mind signal/body signal capture device embodiments 610 include a calibration module 730 configured to perform calibration operations that are essentially identical or analogous to those described above, such as the determination or generation of particular reference mind state parameters and reference body state parameters. Additionally, some embodiments of a portable mind signal/body signal capture device 610 include a subject state analysis module 740 configured to determine or generate particular mind state indicators and body state indicators correlated with mind signals and body signals that have been captured while the subject engages in normal or day-to-day activities (e.g., apart from subject engagement in functional development activity sequences, mind state exercises, or body state exercises by way of subject interaction with a system 10 for unified neurological-physiological rehabilitation, functional development, and/or functional maintenance in accordance with the present disclosure). In certain embodiments, a portable mind signal/body signal capture device 610 also includes a subject performance module 795 configured to estimate, determine, generate, and/or store a set of subject performance measures or metrics and/or mind-body synergy index or indicator values (e.g., BTI(t) values). A portable mind signal/body signal capture device 610 can further include a biofeedback module 755 configured to provide certain types of biofeedback to the subject, for instance, visual biofeedback (e.g., the presentation of a visual mind-body alignment feedback element 414 that is displayed by way of the visual interface 325).

A portable mind signal/body signal capture device 610 can facilitate or enable the subject and/or another individual (e.g., a clinician or therapist) to (a) gain an enhanced awareness of the subject's ability to realize a mind state, body state, and/or mind-body unification state that is expected to synergistically enhance a likelihood of functional maintenance, functional development, learning, or beneficial neural reorganization during normal day-to-day activities; (b) identify one or more types of circumstances (e.g., times of day), situations (e.g., collaborative versus isolated subject situations), activities, or tasks that give rise to or result in optimal, improved, or non-optimal mind state(s), body state(s), or mind-body complex state(s), which can influence or determine the selection of future functional development activity sequences, mind state training exercises, or body state training exercises.

Aspects of Representative Unified Neurological-Physiological Activity Processes

FIG. 9 is a flow diagram of a representative unified neurological-physiological rehabilitation and/or functional development process 800 according to an embodiment of the disclosure. In an embodiment, the process 800 includes a first process portion 802 that involves establishing signal communication with a set of mind signal acquisition devices 100, and initiating continuous or recurrent acquisition of mind signals. Correspondingly, the process 800 includes a second process portion 804 that involves establishing signal communication with a set of body signal acquisition devices 200, and initiating continuous or recurrent acquisition of body signals. The process 800 can include a third process portion 806 that involves performing subject specific calibration operations, such as generating a set of reference mind state parameters and/or a set of reference body state parameters in a manner that is essentially identical or analogous to that described above.

The process 800 includes a fourth process portion 810 that involves recurrently generating or determining a set of mind state indicators corresponding to acquired mind signals; a fifth process portion 812 that involves recurrently generating or determining a set of body state indicators corresponding to acquired body signals; and a sixth process portion 814 that involves recurrently generating or determining a set of mind-body synergy indices or indicators. The process 800 further includes a seventh process portion 820 that involves updating one or more mind state and body state interfaces, such as a set of biofeedback interfaces configured to provide the subject with biofeedback corresponding to the subject's current or recent mind state(s), body state(s), and/or mind-body synergy measure(s) or level(s). Such biofeedback can include the provision of visual information (e.g., graphical, symbolic, textual, image, and/or icon based information) that corresponds to or represents the value(s) of one or more current or recent mind state indicators, body state indicators, and/or mind-body synergy indices, indicators, or measures (e.g., corresponding to a BTI).

The process 800 also includes an eighth process portion 830 that involves providing the subject with an activity mode selection interface. In various embodiments, an activity mode selection interface provides a visual interface or GUI by which the subject can select whether to engage in a mind state mode involving mind state training exercises or games; a body state mode involving body state training exercises or games; or a synergistic mind-body activity mode involving functional development activity sequences. Until the subject selects an activity mode, the seventh and eighth process portions 820, 830 can be repeated.

Once the subject selects an activity mode, the process 800 selectively initiates an ninth process portion corresponding to a mind state training mode 850; a tenth process portion 852 corresponding to a body state training mode 852; or an eleventh process portion 860 corresponding to a synergistic mind-body activity mode based upon subject input.

Figure 10:
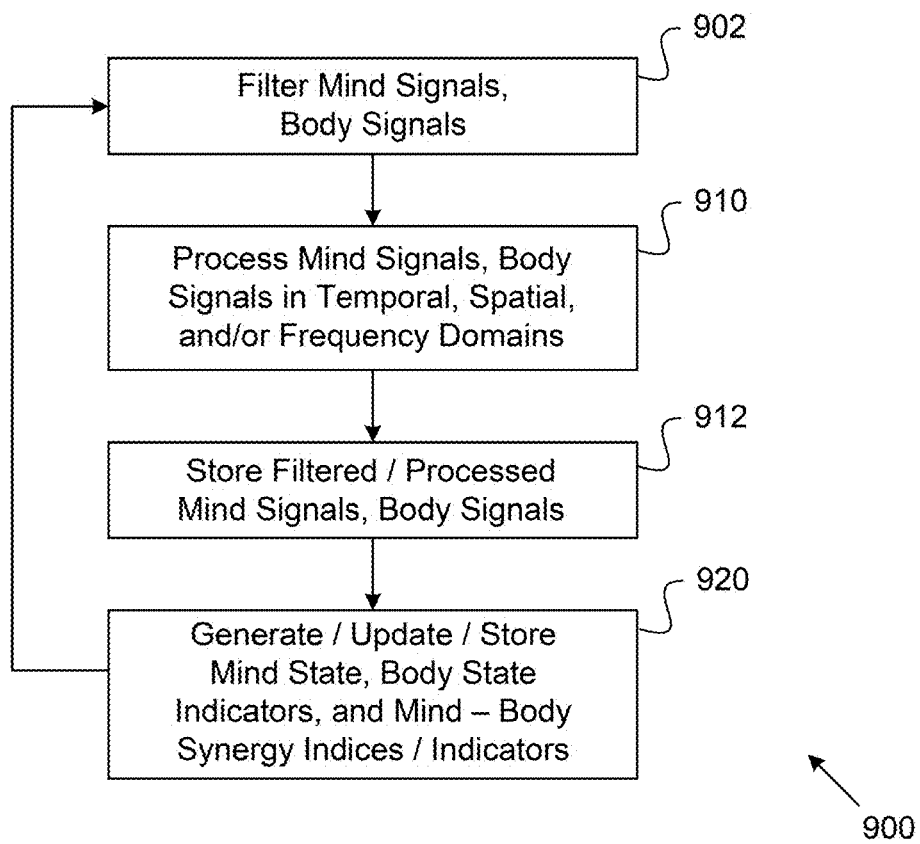
FIG. 10 is a flow diagram of a general process for capturing and processing mind signals and body signals according to an embodiment of the disclosure.

FIG. 10 is a flow diagram of a general process 900 for capturing and processing mind signals and body signals according to an embodiment of the disclosure. In an embodiment, the process 900 includes a first process portion 902 that involves filtering captured mind signals and body signals. A second process portion 910 involves processing mind signals and body signals in temporal, spatial, and/or frequency domains, and a third process portion involves storing filtered and/or processed mind signals and body signals. A fourth process portion 920 involves generating, updating, and/or storing a set of values or signals corresponding to one or more mind state indicators, body state indicators, and/or mind-body synergy indices or indicators based upon the filtered and/or processed mind signals and body signals, respectively. Representative aspects or generating mind state indicators, body state indicators, and mind-body synergy indices or indicators in particular embodiments of the disclosure are described in detail hereafter.

Figure 11A:
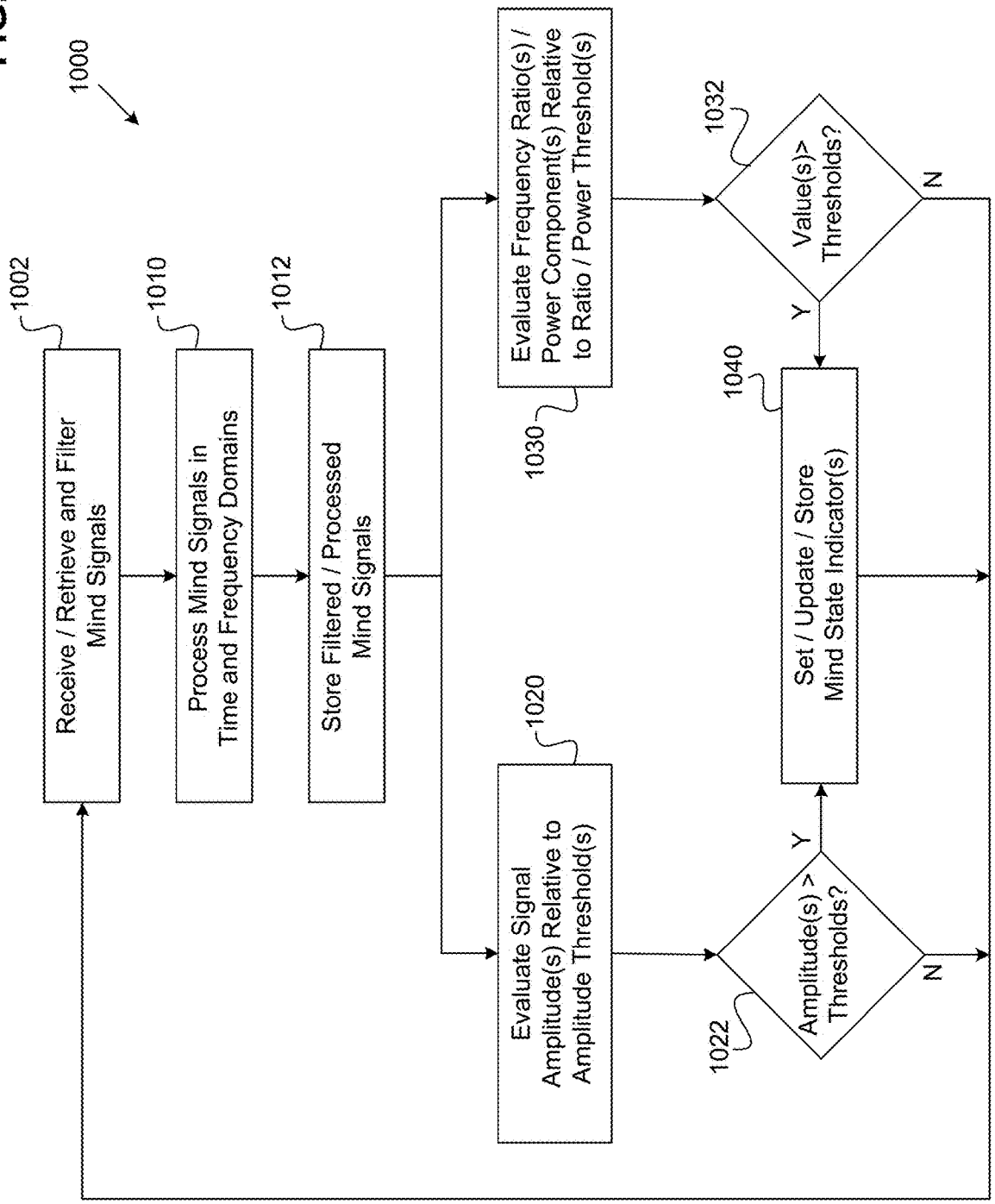
FIG. 11A is a flow diagram of a process for generating mind state indicators according to an embodiment of the disclosure.

FIG. 11A is a flow diagram of a process 1000 for generating mind state indicators according to an embodiment of the disclosure. In an embodiment, the process 1000 includes a first process portion 1002 involving receiving or retrieving and filtering captured or stored mind signals. A second process portion 1010 involves processing such mind signals in the time domain and frequency domain, and a third process portion 1012 involves storing filtered and/or processed mind signals.

A fourth process portion 1020 involves evaluating filtered or processed mind signal amplitude values relative to one or more reference mind signal amplitude threshold parameter values; and a fifth process portion 1030 involves evaluating mind signal frequency ratios and/or power components relative to mind signal frequency and/or power ratio threshold parameter values. If the mind signal amplitude values exceed their corresponding amplitude threshold parameter values, a sixth process portion 1040 sets, updates, or stores mind state indicators that convey that such amplitude threshold parameter values have been exceeded; otherwise, the process 1000 returns to the first process portion 1002. Additionally, if the mind signal frequency ratios or power components respectively exceed their corresponding frequency ratio or power component threshold parameter values, the sixth process portion 1040 sets, updates, or stores mind state indicators that convey that such frequency ratio or power component threshold parameter values have been exceeded; otherwise, the process 1000 returns to the first process portion 1002.

Figure 11B:
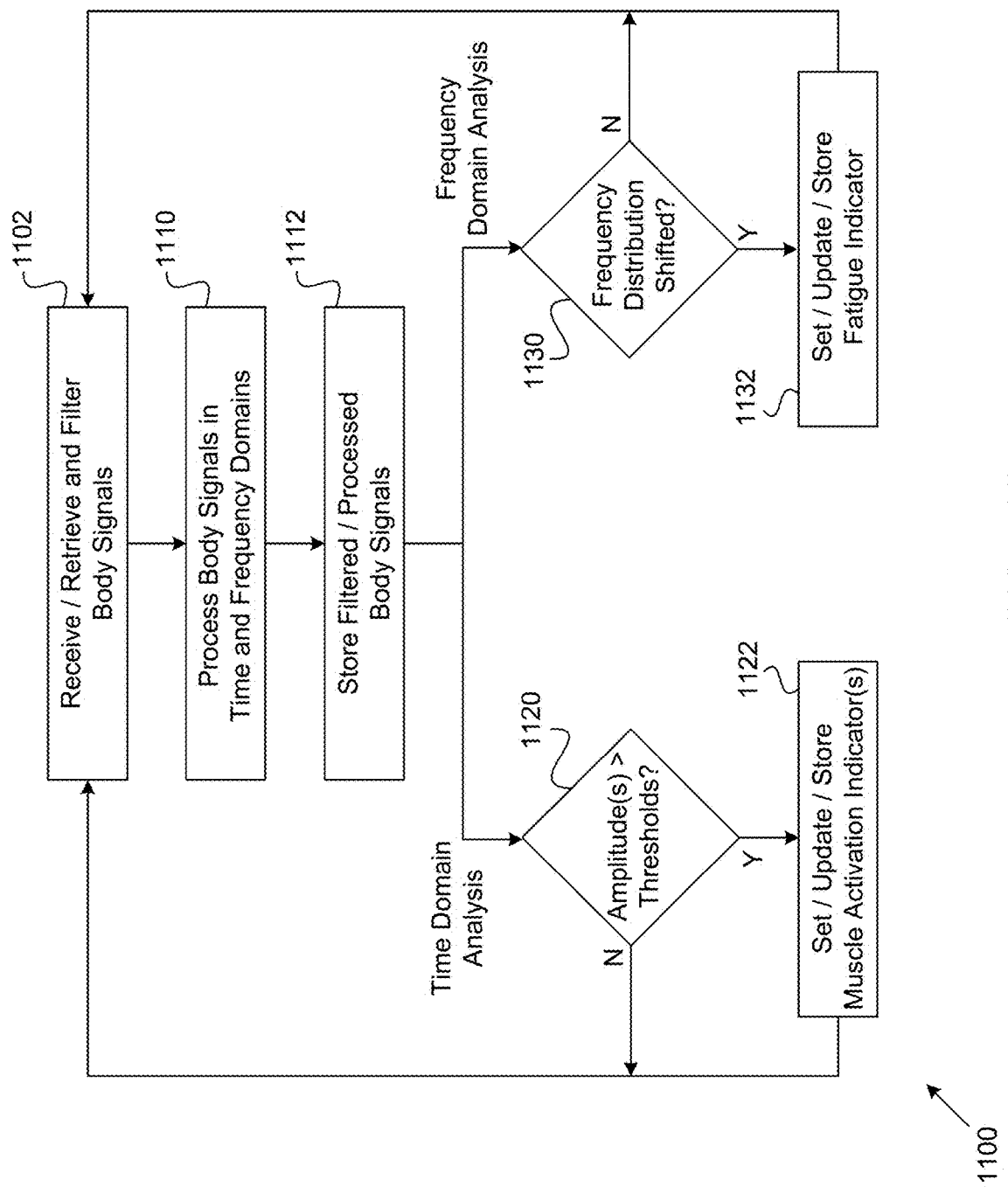
FIG. 11B is a flow diagram of a process for generating body state indicators according to an embodiment of the disclosure.

FIG. 11B is a flow diagram of a process 1100 for generating body state indicators according to an embodiment of the disclosure. In an embodiment, the process 1100 includes a first process portion 1102 involving receiving or retrieving and filtering captured or stored body signals. A second process portion 1110 involves processing such body signals in the time domain and frequency domain, and a third process portion 1112 involves storing filtered and/or processed body signals.

A fourth process portion 1120 involves evaluating filtered or processed body signal amplitude values relative to one or more reference body signal amplitude threshold parameter values to determine whether such body signal amplitude values exceed the reference body signal amplitude threshold parameter values. If so, a fifth process portion 1122 involves setting, updating, or storing one or more muscle activation indicators that convey that such body signal amplitude thresholds have been exceeded. A muscle activation indicator can correspond to, include, or be, for instance, an RVC signal. Following the fifth process portion 1122, or in the event that body signal amplitude values do not exceed corresponding reference body signal amplitude threshold parameter values, the process 1100 returns to the first process portion 1102.

A sixth process portion 1130 involves evaluating body signal frequency components and determining whether a current or recent set of captured body signals exhibits a frequency distribution shift relative to previously captured body signals. If so, a seventh process portion 1132 involves setting, updating, or storing a fatigue indicator to convey that one or more muscles or muscle groups under consideration is fatigued or becoming fatigued. Following the seventh process portion 1132, or in the event that no frequency distribution shift was detected, the process 1100 returns to the first process portion 1102.

Figure 11C:
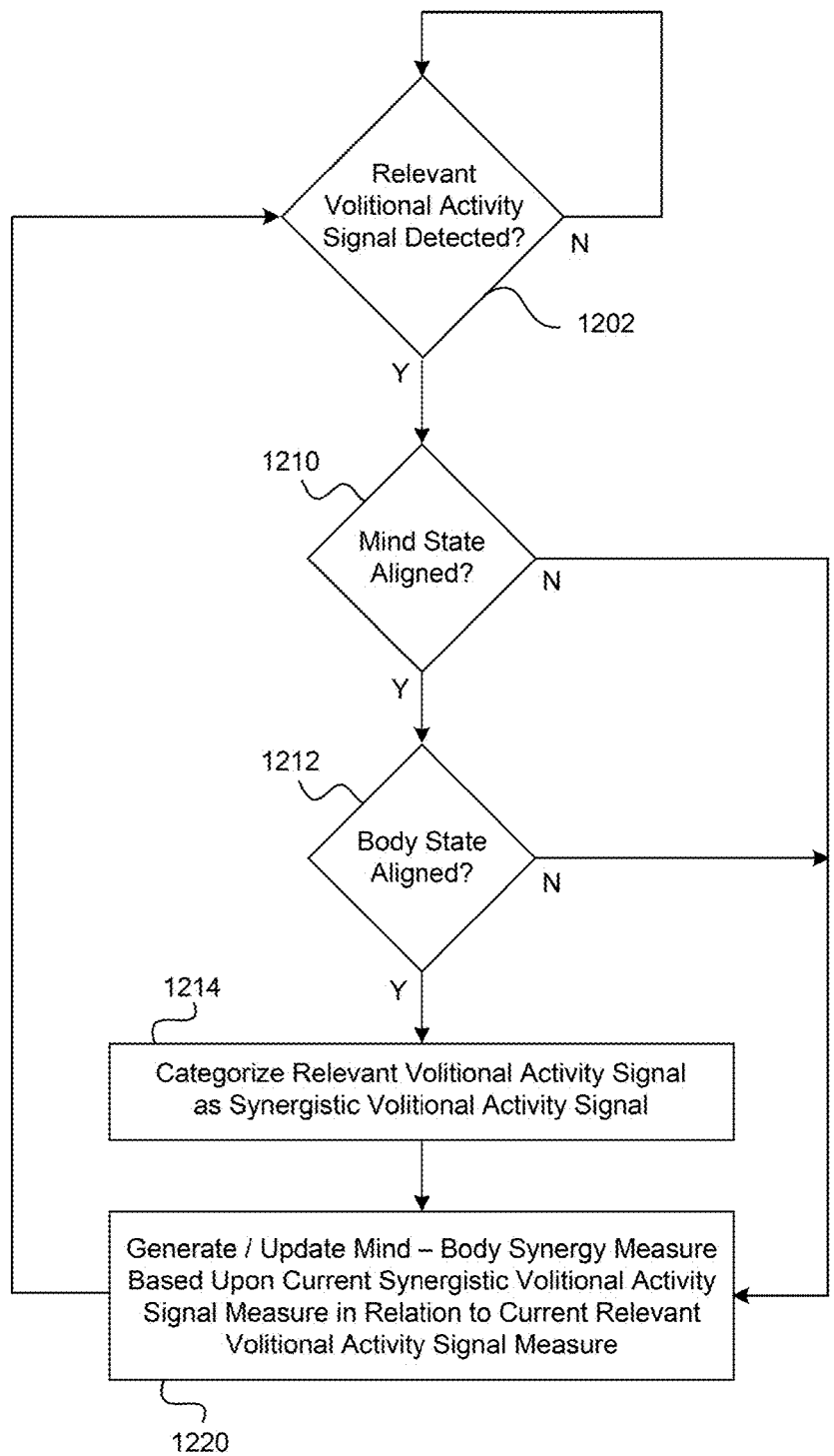
FIG. 11C is a flow diagram of a process for generating a set of mind-body synergy indicators according to an embodiment of the disclosure.

FIG. 11C is a flow diagram of a process 1200 for generating a set of mind-body synergy indicators according to an embodiment of the disclosure. In an embodiment, the process 1200 includes a first process portion 1202 involving determining whether a set of significant, successful, or relevant volitional activity signals (e.g., a set of RVC signals) has been generated or detected. If not, the process 1200 can remain at the first process portion 1202.

In response to the generation or detection of one or more relevant volitional activity signals, a second process portion 1210 determines whether a mind state alignment criterion is satisfied, and a third process portion 1212 determines whether a body state alignment criterion is satisfied. For instance, a mind state alignment criterion can be based upon whether a current mind alignment indicator $M_A(t)$ is greater than or equal to a threshold or minimum mind state alignment indicator value $M_{A\ threshold}$; and a body state alignment criterion can be based upon whether a current body state alignment indicator $B_A(t)$ is greater than or equal to a threshold or minimum body state alignment indicator value $B_{A\ threshold}$.

If each of the mind state alignment criterion and the body state alignment criterion is satisfied or met, a fourth process portion 1214 involves categorizing or defining the relevant volitional activity signal(s) as synergistic volitional activity signal(s) (e.g., SVC signal(s)), indicating that the relevant volitional activity signal(s) occurred while each of the subject's mind state and body state were synergistically or cooperatively coordinated in a manner that is expected to increase a likelihood of facilitating or enabling spontaneous, non-incremental, or surprising spurts or bursts in the subject's functional development, recovery, or learning.

If the mind state alignment criterion and body state alignment criterion were each satisfied, or if at least one of the mind state alignment criterion and body state alignment criterion were not satisfied, the processes 1200 proceeds to a fifth process portion 1220 that involves generating or updating a mind-body synergy index, indicator, or measure based upon a current or cumulative synergistic volitional activity signal occurrence measure in relation to a current or cumulative relevant volitional activity signal occurrence measure. A relevant volitional activity signal occurrence measure can correspond to or be a number of times relevant volitional activity signals have been generated or detected; and a synergistic volitional activity signal occurrence measure can correspond to or be a number of times such relevant volitional activity signals have been categorized as synergistic in accordance with the mind state and body state alignment criteria.

Figure 12:
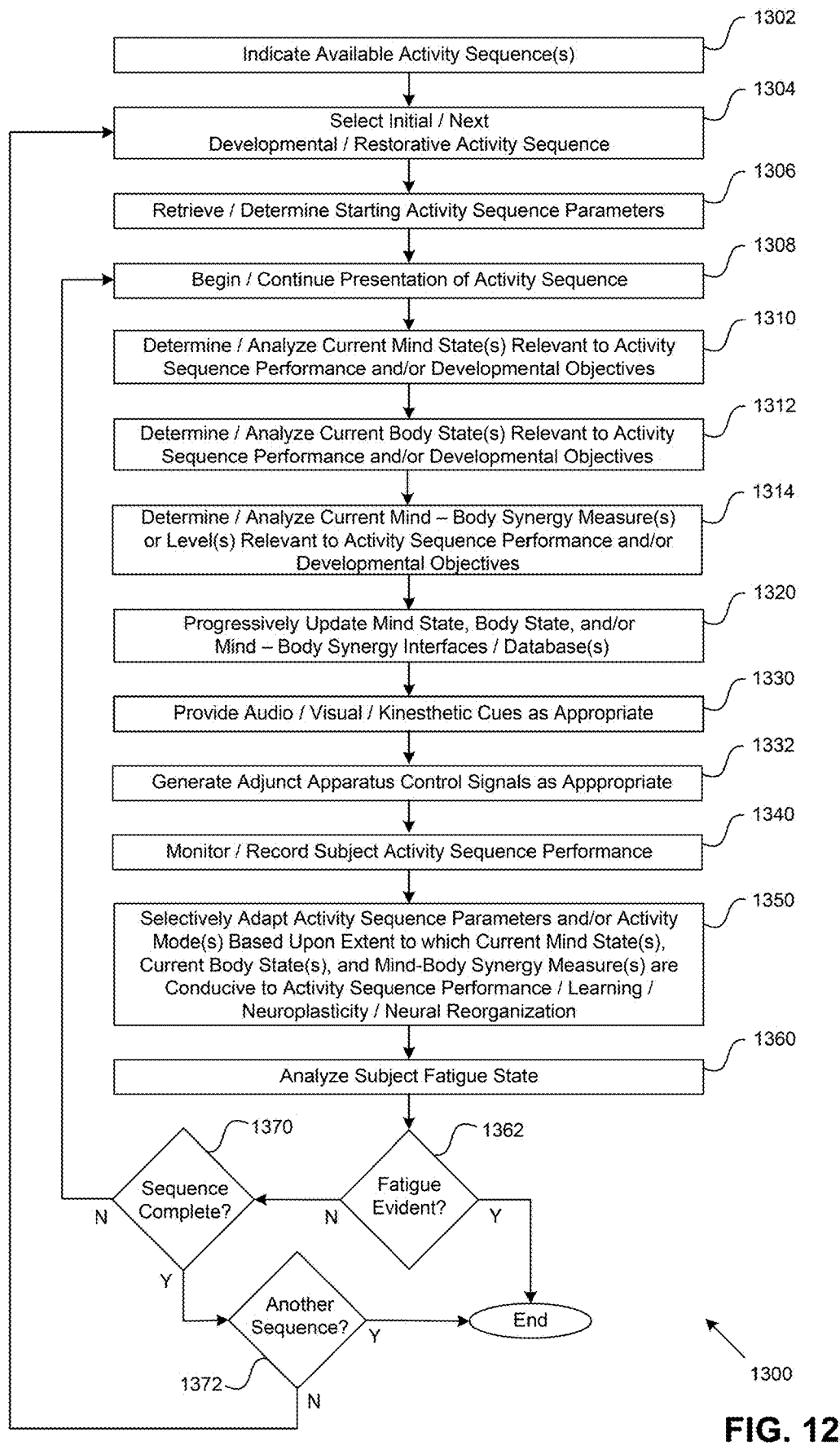
FIG. 12 is a flow diagram of a process for performing synergistic mind-body activity mode operations according to an embodiment of the disclosure.

FIG. 12 is a flow diagram of a process 1300 for performing synergistic mind-body activity mode operations according to an embodiment of the disclosure. In an embodiment, the process 1300 includes a first process portion 1302 that involves indicating to the subject what functional development activity sequences are currently available to the subject. The first process portion 1302 can involve the presentation of a functional development activity sequence menu, and/or a set of images, icons, or text corresponding to available functional development activity sequences to the subject by way of a display device 322.

A second process portion 1304 involves selecting a first or next functional development activity sequence for presentation to the subject in response to subject and/or clinician selection or input. A third process portion 1306 involves retrieving or determining a set of initial parameters for the functional development activity sequence currently under consideration. Such parameters can include one or more of a difficulty level, a repetition rate, and a repetition count corresponding to one or more activities, tasks, or exercises within the current functional development activity sequence that the subject is to attempt to perform or perform. A fourth process portion 1308 involves presenting the functional development activity sequence to the subject by way of the visual interface 320 and possibly the audio interface 330 in accordance with the current set of functional development activity sequence parameters.

A fifth process portion 1310 involves determining analyzing aspects of the subject's current mind state(s) that are relevant to the performance of the current functional development activity sequence and/or developmental objectives such as enhanced learning or favorable neural reorganization. The fifth process portion 1310 can include the retrieval, estimation, determination, evaluation, or analysis of one or more mind state indicators. In multiple embodiments, the fifth process portion 1310 can be initiated in response to a detection of the subject's initiation or attempted initiation of a task, activity, or exercise within the current functional development activity sequence, as further described in detail below.

A sixth process portion 1312 involves determining or analyzing aspects of the subject's current body state(s) that are relevant to the performance of the current functional development activity sequence and/or developmental objectives such as enhanced learning or favorable neural reorganization. The sixth process portion 131 can include the retrieval, generation, estimation, determination, evaluation, or analysis of one or more body state indicators.

A seventh process portion 1314 involves determining or analyzing aspects of the subject's current mind-body synergy measure(s) or level(s) that are relevant to the current functional development activity sequence and/or developmental objectives such as increasing a likelihood of realizing spontaneous, sudden, dramatic, non-incremental, nonlinear, surprising, unexpected, and/or lasting (e.g., long lasting or essentially permanent) gains in functional capabilities and/or performance. The seventh process portion 1314 can include the generation and analysis of a mind-body synergy measure such as a BTI index, indicator, or measure described above.

An eighth process portion 1320 involves progressively updating mind state, body state, and/or mind-body synergy interfaces, one or more of which can include biofeedback interfaces, and possibly updating one or more databases that store mind state, body state, and/or mind-body synergy related information. A ninth process portion 1330 can involve the generation or provision of one or more types of cues to the subject, where such cues can be intended to time or synchronize subject efforts with aspects of the current functional development activity sequence. A tenth process portion 1332 can involve the generation or output of a set of control signals for one or more adjunct apparatuses 500. Such control signals can include FES signals and/or robotic orthosis control signals that can facilitate subject performance of a task, activity, or exercise within the current functional development activity sequence. An eleventh process portion 1340 involves monitoring or recording subject performance signals.

A twelfth process portion 1350 involves selectively (a) adapting functional development activity sequence parameters; (b) transitioning to a mind state mode involving the provision of mind state training exercises or games to the subject; or (c) transitioning to a body state mode involving the provision of body state training exercises or games to the subject based upon an extent to which the subject's current mind state indicator(s), body state indicator(s), and/or mind-body synergy measure(s) appear to be conducive to subject performance of the current functional development activity sequence, learning, or favorable neural reorganization. Particular aspects of the twelfth process portion 1350, in association with aspects of one or more of the fifth, sixth, and seventh process portions 1310-1314, are described in detail below for a representative embodiment with respect to FIGS. 13-15.

A thirteenth process portion 1360 involves analyzing a subject fatigue state (e.g., muscular fatigue), and a fourteenth process portion 1362 can determine whether subject fatigue is evident, likely, or becoming likely. If subject fatigue is evident, the process 1300 can terminate or pause. If fatigue is not evident, a fifteenth process portion 1370 can determine whether presentation of the current functional development activity sequence to the subject is complete. If not, the process 1300 can return to the fourth process portion 1308. If presentation of the current functional development activity sequence is complete, a sixteenth process portion 1372 can determine whether another functional development activity sequence requires consideration. If so, the process 1300 can return to the second process portion; otherwise, the process 1300 can end.

Figure 13:
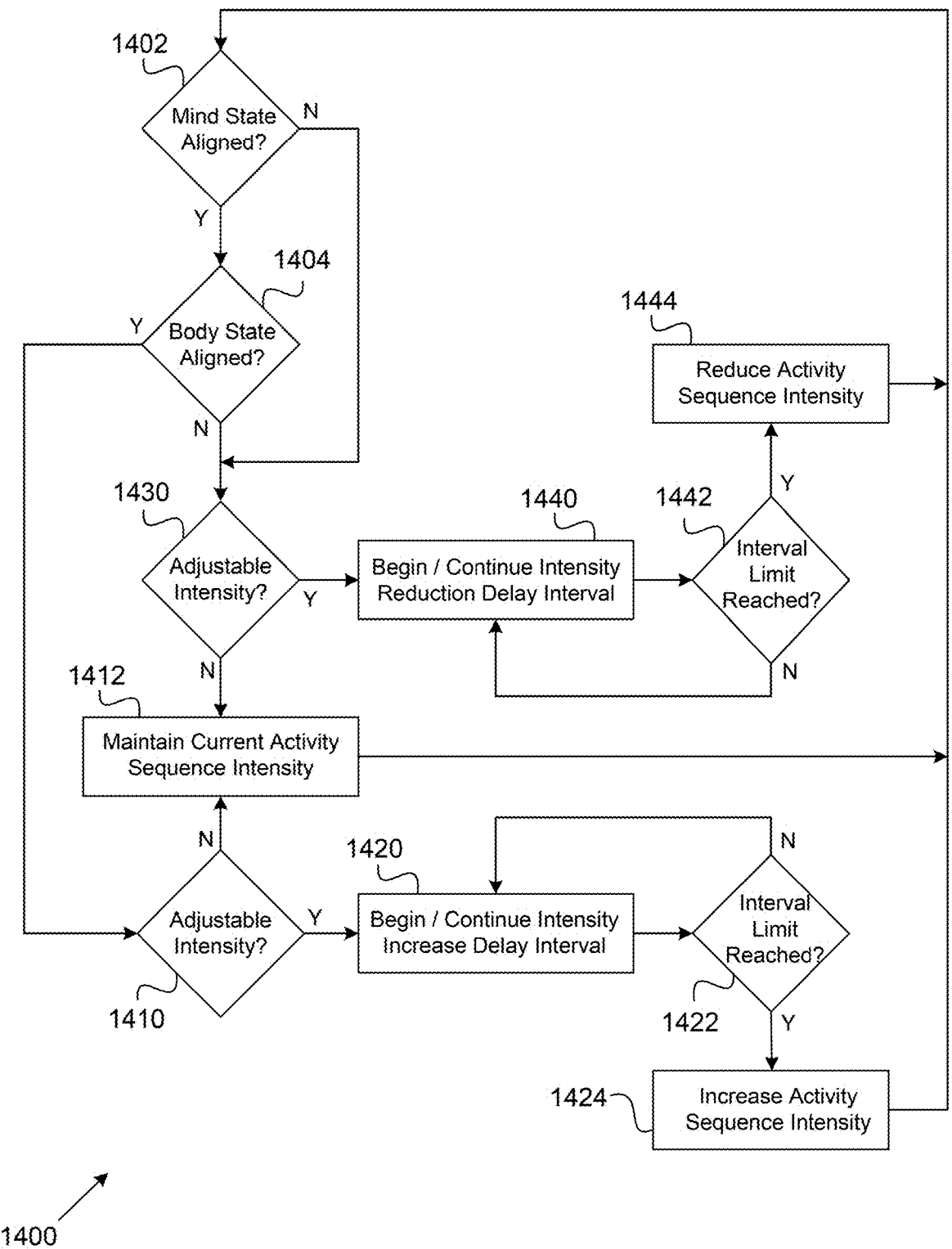
FIG. 13 is a flow diagram of a process for adaptively adjusting functional development activity sequence parameters according to an embodiment of the disclosure.

FIG. 13 is a flow diagram of a process 1400 for adaptively adjusting functional development activity sequence parameters according to an embodiment of the disclosure. In an embodiment, adjustable functional development activity sequence parameters can include a set of activity intensity parameters corresponding to an activity or task difficulty level and/or presentation rate. For instance, an activity intensity parameter can be a number of times that one or more tasks within a functional activity development sequence are repeatedly or successively presented to the subject relative to a given period of time (e.g., a number of activities or tasks per minute, or an overall duration of a functional development activity sequence). Depending upon embodiment details, one or more activity intensity parameters may be defined as adjustable or non-adjustable at particular times. For instance, in the event that a subject is just learning to use or interact with the system 10, particular intensity parameters may be set in accordance with a "low intensity" training mode, and such parameters may remain fixed, non-adjustable, or adjustable within predetermined, programmable, or selectable limits (e.g., as determined in response to clinician and/or subject input) until the subject has used the system 10 a certain number of times or for a certain period of time.

In an embodiment, a first process portion 1402 involves determining whether the subject's mind state is conducive or aligned with respect to activity or task performance, leaning, and/or developmental objectives, for instance, by determining whether one or more mind state alignment indicators $M_A(t)$ satisfy corresponding mind state alignment criteria such as meeting or exceeding threshold or minimum mind state alignment indicator values (e.g., $M_{A\ threshold}$ values) A second process portion 1404 involves determining whether the subject's body state $B_A(t)$ is conducive or aligned with respect to activity or task performance, learning, and/or developmental objectives, such as by determining whether one or more body state alignment indicators satisfy corresponding body state alignment criteria, such as meeting or exceeding threshold or minimum body state alignment indicator values (e.g., $B_{A\ threshold}$ values).

In multiple embodiments, the first and second process portions 1402, 1402 can be performed on a recurring or ongoing basis in association or in parallel with the performance of other portions of the process 1400. For instance, the first and second process portions 1402, 1404 can each be performed approximately every 2-20 seconds (e.g., approximately every 5, 10, or 15 seconds). In some embodiments, the determination of whether the subject's mind state is aligned relative to activity or task performance, learning, and/or developmental objectives can occur by way of checking the value of a mind state alignment flags, and the determination of whether the subject's body state is aligned relative to activity or task performance, learning, and/or development objectives can occur by way of checking the value of a body state alignment flag, as further described in detail below.

In the event that the subject's mind state and body state are each aligned with activity or task performance and/or learning, a third process portion 1410 involves determining whether an activity intensity is adjustable. If not, a fourth process portion 1412 involves maintaining a current or most recent activity intensity, after which the process 1400 returns to the first process portion 1402. If an activity intensity is adjustable, a fifth process portion 1420 involves initiating or continuing an intensity increase delay interval $d_i$ (for instance, approximately 10-120 seconds, e.g., approximately 30-90 seconds, or about 60 seconds) prior to increasing the activity intensity, and a sixth process portion 1422 involves determining whether the intensity increase delay interval $d_i$ has expired. If not, the process 1400 returns to the fifth process portion 1420. Otherwise, a seventh process portion 1424 involves increasing an activity intensity, after which the process 1400 returns to the first process portion 1402.

In the event that one or both of the subject's mind state and body state are not aligned with activity or task performance and/or learning, an eighth process portion 1430 involves determining whether an activity intensity is adjustable. If not, the process 1400 maintains an activity intensity at a current or most recent level or value in association with the fourth process portion 1412. Otherwise, a ninth process portion 1440 involves initiating or continuing an intensity decrease delay interval $d_d$ (for instance, approximately 5-30 seconds, e.g., approximately 5-15 seconds, or about 10 seconds), and a tenth process portion 1442 involves determining whether the intensity decrease delay interval $d_d$ has expired. If not, the process 1400 returns to the ninth process portion 1440. Once the intensity decrease delay interval has expired, an eleventh process portion 1444 involves decreasing an activity intensity level, after which the process 1400 returns to the first process portion 1400.

Depending upon embodiment details, an extent or degree to which an activity intensity can be increased or decreased can be correlated with a predetermined, programmable, or selectable activity increment or decrement parameter, respectively.

An activity increment parameter or activity decrement parameter can be an offset or multiplier that is applied to a current activity intensity. For instance, an activity increment parameter or an activity decrement parameter can have a value of approximately 0.05-0.20 (e.g., about 0.10), corresponding to a percentage by which an activity intensity can be adjusted. An activity increment parameter and an activity decrement parameter can be identical, substantially identical, or different with respect to each other.

In certain embodiments, a single activity intensity adjustment parameter z represents an activity increment parameter and an activity decrement parameter. In a representative implementation, a set of activity intensity adjustment conditions involving an activity intensity adjustment parameter z can be defined as follows:

Increase: $I_{N+1}=(1+z)*I_N$ if $M_A(t)$ and $B_A(t) \geq 0.5$ and $d_i > 60$ seconds Maintain: $I_{N+1}=I_N$ if $M_A(t)$ and $B_A(t) \geq 0.5$ and $d_i < 60$ seconds Decrease: $I_{N+1}=(1-z)*I_N$ if $M_A(t)$ and $B_A(t) \geq 0.5$ and $d_i > 10$ seconds where z=approximately 0.10.

The value of z can be determined or selected based upon embodiment details; data corresponding to healthy or unimpaired individuals; the nature, extent, or severity of subject impairment under consideration; and/or a current subject fatigue level.

Figure 14:
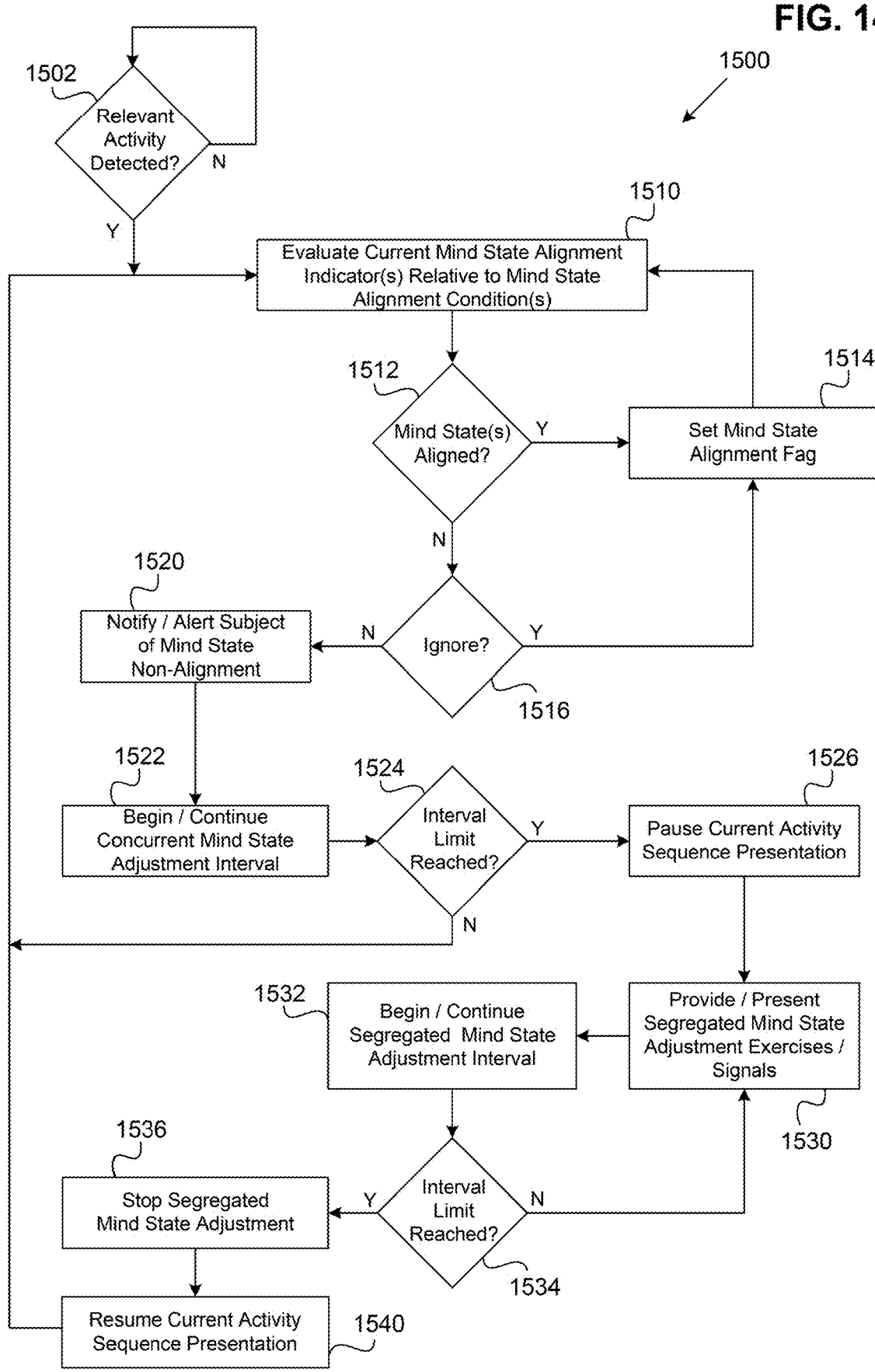
FIG. 14 is a flow diagram of a process for selectively transitioning from a synergistic mind-body activity mode involving the subject's performance or attempted performance of one or more portions of a functional development activity sequence to a mind state training mode involving the provision of mind state training routines, exercises, or games to the subject according to an embodiment of the disclosure.

FIG. 14 is a flow diagram of a process 1500 for selectively transitioning from a synergistic mind-body activity mode involving the subject's performance or attempted performance of one or more portions of a functional development activity sequence to a mind state training mode involving the provision of mind state training routines, exercises, or games to the subject according to an embodiment of the disclosure. In an embodiment, the process 1500 includes a first process portion 1502 involving determining whether relevant volitional activity associated with a functional development activity sequence has been detected. For instance, in some embodiments, the first process portion 1502 involves determining whether a relevant volitional activity signal such as an RVC signal has been generated or detected during the presentation of a functional development activity sequence to the subject. If not, the first process 1500 can remain at the first process portion 1502.

Once relevant volitional activity has been detected, a second process portion 1510 involves evaluating the subject's current mind state alignment indicator(s) (e.g., $M_{A1}(t)$, $M_{A2}(t)$, etc. . . . ) relative to associated mind state alignment condition(s) (e.g., corresponding to threshold mind state alignment indicator values $M_{A1\ threshold}$, $M_{A2\ threshold}$, etc. . . . ) in a manner analogous to that described above, and a third process portion 1512 involves determining whether the subject's current mind state alignment indicator(s) satisfy the mind state alignment condition(s). If so, a fourth process portion 1514 involves setting a mind state alignment flag that indicates the subject's mind state is aligned with or conducive to functional development activity sequence performance, learning, and/or favourable neural reorganization. Following the fourth process portion 1514, the process 1500 returns to the second process portion 1510.

In the event that the mind state alignment condition(s) are not satisfied, a fifth process portion 1516 involves determining whether the mind state alignment condition(s) can be ignored. Certain embodiments of the present disclosure provide for a lack of mind state alignment to be ignored during portions of one or more therapy sessions or time periods, for instance, in response to subject or clinician input, which can aid or accelerate training the subject during a training period in which the subject may not be familiar with certain system features or functions. In the event that a lack of mind state alignment can be ignored, the process 1500 can proceed to the fourth process portion 1514 to set the mind state alignment flag.

If a lack of mind state alignment is not to be ignored (i.e., if operations undertaken in response to a lack of mind state alignment are distinct from operations undertaken in response to a presence of mind state alignment), a sixth process portion 1520 includes notifying or alerting the subject of their mind state non-alignment. The sixth process portion 1520 can involve providing biofeedback (e.g., audio, visual, haptic, or proprioceptive biofeedback) to the subject to indicate the nature and/or an extent of mind state non-alignment. A seventh process portion 1522 involves initiating or continuing a mind state adjustment interval (e.g., approximately 30-180 seconds, or approximately 60-120 seconds) concurrent with continued or ongoing activity sequence presentation to the subject. During a concurrent mind state adjustment interval, the subject is provided with a time interval in which they can volitionally adapt their mind state in a manner that is synergistic with, conducive to, or supportive of functional development activity sequence performance, learning, and/or favourable neural reorganization, for instance, by realizing altered or adjusted neural firing patterns that result in the mind state alignment indicator(s) satisfying the mind state alignment condition(s). An eighth process portion 1524 involves determining whether the concurrent mind state adjustment interval has expired. If not, the process 1500 returns to the second process portion 1510.

If the subject's mind state remains non-aligned, following the expiration of the concurrent mind state adjustment interval a ninth process portion 1526 involves pausing or interrupting presentation of the current functional development activity sequence to the subject, and a tenth process portion 1530 involves providing mind state training routines, adjustment exercises, games, and/or signals to the subject, separate or segregated from functional development activity sequence presentation to the subject. An eleventh process portion 1532 involves initiating or continuing a segregated mind state adjustment interval (e.g., approximately 30-180 seconds, or approximately 60-120 seconds) associated with the tenth process portion 1530, during which the subject can engage or attempt to engage in mind state training exercises separate from functional development activity sequence presentation.

The tenth process portion 1530 can involve generating or displaying a mind state training or exercise interface 440, 450, and presenting mind state training exercises or games to the subject. In various embodiments, the tenth process portion 1530 can involve presenting mind state training exercises to the subject that are known to have previously resulted in or are expected to result in the subject's attainment of a mind state that gives rise to one or more mind state alignment indicator values (e.g., $M_{A1}(t)$, $M_{A2}(t)$, etc. . . . ) that significantly, very significantly, and/or sustainably exceed one or more corresponding threshold mind state alignment indicator values (e.g., $M_{A1\ threshold}$, $M_{A2\ threshold}$, etc. . . . ).

The tenth process portion 1530 can additionally or alternatively involve presenting one or more of an audio and/or visual mental relaxation routine; music, sound, or rhythm therapy; and binaural audio signals to the subject in a manner that is expected to increase a likelihood that the subject's neural firing patterns give rise to EEG measures or signal levels that can result in the subject's realization of or return to mind state alignment.

A twelfth process portion 1534 involves determining whether the segregated mind state adjustment interval has expired. If not, the process 1500 returns to the tenth process portion 1530. Once the segregated mind state adjustment interval has expired, a thirteen process portion 1536 involves terminating the presentation of segregated mind state training or exercises to the subject, and a fourteenth process portion 1540 involves resuming the current or most recent functional development activity sequence presentation to the subject (e.g., at a time point within functional development activity sequence presentation corresponding to a most recently attempted or completed functional development activity or task). Following the fourteenth process portion 1540, the process 1500 returns to the second process portion 1510.

Figure 15:
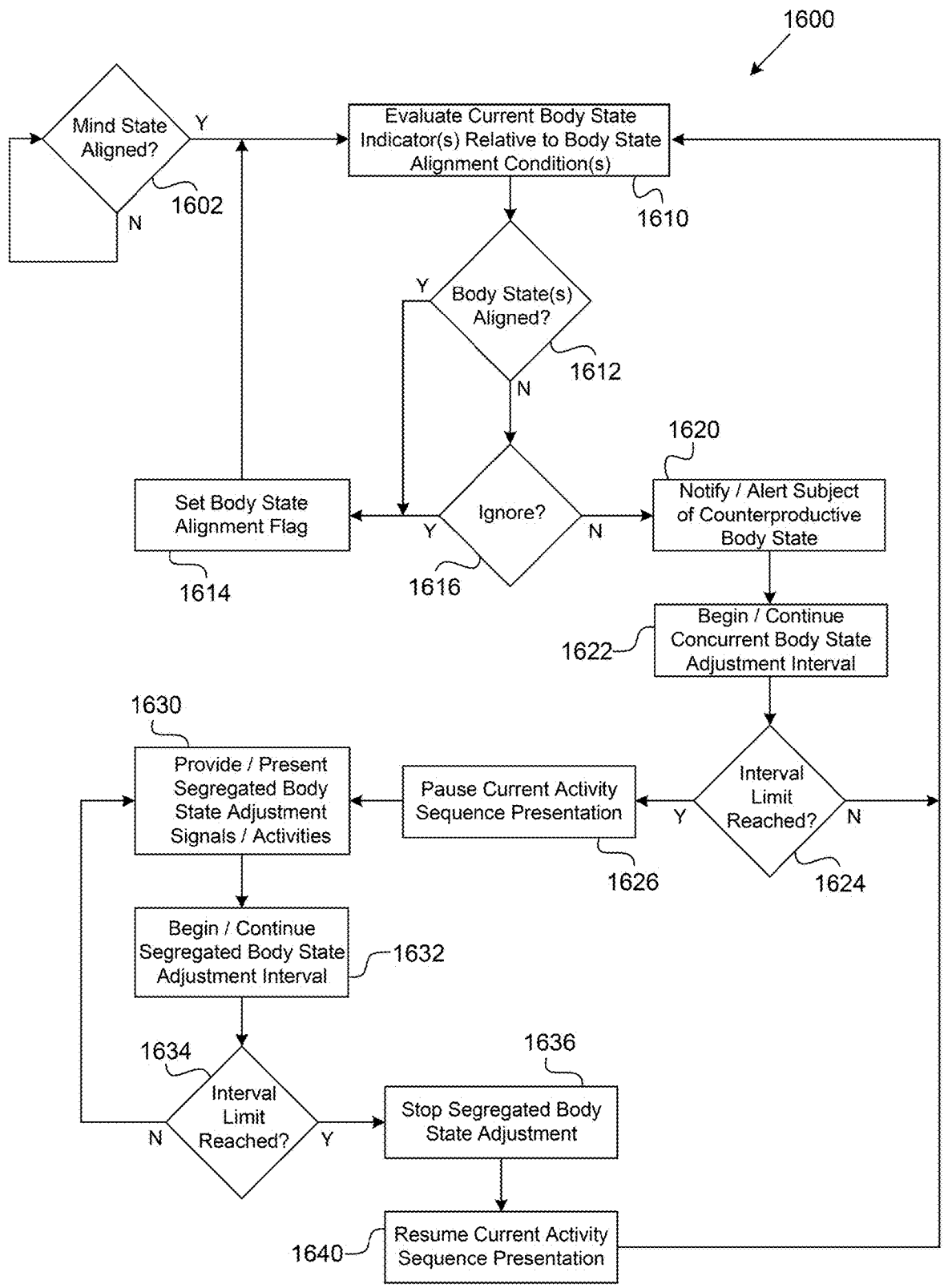
FIG. 15 is a flow diagram of a process for selectively transitioning from a synergistic mind-body activity mode involving the subject's performance or attempted performance of a functional development activity sequence to a body state training or exercise mode involving the provision of body state training routines, exercises, or games to the subject according to an embodiment of the disclosure.

FIG. 15 is a flow diagram of a process 1600 for selectively transitioning from a synergistic mind-body activity mode involving the subject's performance or attempted performance of a functional development activity sequence to a body state training or exercise mode involving the provision of body state training routines, exercises, or games to the subject according to an embodiment of the disclosure. In an embodiment, the process 1600 includes a first process portion 1602 involving determining whether the subject's current mind state is aligned, for instance, by checking the value of a mind state alignment flag. If the subject's mind state is not aligned, the process 1600 returns to the first process portion 1602.

If the subject's current mind state is aligned, a second process portion 1610 involves evaluating the subject's current body state alignment indicator(s) (e.g., $B_{A1}(t)$, $B_{A2}(t)$, etc. . . . ) relative to associated body state alignment condition(s) (e.g., corresponding to threshold body state alignment indicator values $B_{A1\ threshold}$, $B_{A2\ threshold}$, etc. . . . ) in a manner analogous to that described above, and a third process portion 1612 involves determining whether the subject's current body state alignment indicator(s) satisfy the body state alignment condition(s). If so, a fourth process portion 1614 involves setting a body state alignment flag that indicates the subject's body state is aligned with or conducive to functional development activity sequence performance, learning, and/or favourable neural reorganization. Following the fourth process portion 1614, the process 1600 returns to the second process portion 1610.

In the event that the body state alignment condition(s) are not satisfied, a fifth process portion 1616 involves determining whether the body state alignment condition(s) can be ignored. Certain embodiments of the present disclosure provide for a lack of body state alignment to be ignored during portions of one or more therapy sessions or time periods, for instance, in response to subject or clinician input, which can aid or accelerate training the subject during a training period in which the subject may not be familiar with certain system features or functions. In the event that a lack of body state alignment can be ignored, the process 1600 can proceed to the fourth process portion 1614 to set the body state alignment flag.

If a lack of body state alignment is not to be ignored (i.e., if operations undertaken in response to a lack of body state alignment are distinct from operations undertaken in response to a presence of body state alignment), a sixth process portion 1620 includes notifying or alerting the subject of their body state non-alignment. The sixth process portion 1620 can involve providing biofeedback (e.g., audio, visual, haptic, or proprioceptive biofeedback) to the subject to indicate the nature and/or an extent of body state non-alignment. A seventh process portion 1622 involves initiating or continuing a body state adjustment interval (e.g., approximately 30-180 seconds, or approximately 60-120 seconds) concurrent with continued or ongoing activity sequence presentation to the subject. During a concurrent body state adjustment interval, the subject is provided with a time interval in which they can volitionally adapt their body state in a manner that is synergistic with, conducive to, or supportive of functional development activity sequence performance, learning, and/or favourable neural reorganization, for instance, by altering muscle contraction or co-contraction levels in a manner that results in the body state alignment indicator(s) satisfying the body state alignment condition(s). An eighth process portion 1624 involves determining whether the concurrent body state adjustment interval has expired. If not, the process 1600 returns to the second process portion 1610.

If the subject's body state remains non-aligned, following the expiration of the concurrent body state adjustment interval a ninth process portion 1626 involves pausing or interrupting presentation of the current functional development activity sequence to the subject, and a tenth process portion 1630 involves providing body state training routines, adjustment exercises, games, and/or signals to the subject, separate or segregated from functional development activity sequence presentation to the subject. An eleventh process portion 1632 involves initiating or continuing a segregated body state adjustment interval (e.g., approximately 30-180 seconds, or approximately 60-120 seconds) associated with the tenth process portion 1630, during which the subject can engage or attempt to engage in body state training exercises separate from functional development activity sequence presentation.

The tenth process portion 1630 can involve generating or displaying a body state training or exercise interface 460, 470, and presenting body state training routines, exercises, or games to the subject. In various embodiments, the tenth process portion 1630 can involve presenting body state training exercises to the subject that are known to have previously resulted in or are expected to result in the subject's attainment of a body state that gives rise to one or more body state alignment indicator values (e.g., $B_{A1}(t)$, $B_{A2}(t)$, etc. . . . ) that significantly, very significantly, and/or sustainably exceed one or more corresponding threshold body state alignment indicator values (e.g., $B_{A1\ threshold}$, $B_{A2\ threshold}$, etc. . . . ).

In some embodiments, the tenth process portion 1630 additionally or alternatively involves providing haptic or proprioceptive signals to the subject in a manner that is expected to increase a likelihood that the subject's muscle contraction or co-contraction patterns can result in the subject's realization of or return to body state alignment.

A twelfth process portion 1634 involves determining whether the segregated body state adjustment interval has expired. If not, the process 1600 returns to the tenth process portion 1630. Once the segregated body state adjustment interval has expired, a thirteen process portion 1636 involves terminating the presentation of segregated body state training or exercises to the subject, and a fourteenth process portion 1640 involves resuming the current or most recent functional development activity sequence presentation to the subject (e.g., at a time point within functional development activity sequence presentation corresponding to a most recently attempted or completed functional development activity or task). Following the fourteenth process portion 1640, the process 1600 returns to the second process portion 1610.

FIGS. 16A-16I are representative visual interfaces for configuring system options/parameters associated with mind signals ("Thought"), body signals ("Purpose"), activity intensity ("Energy"), activity sequences and relaxation/training games ("Action"), mind signal and body signal selections/definitions/sources ("Effect"), and Functional Electrical Stimulation (FES). Such interfaces can receive input from, for instance, a medical professional such as a clinician or therapist, for selectively configuring various aspects of system operation, including aspects of system operation described above with reference to FIGS. 9-15.

In an embodiment, a set of system configuration visual interfaces can include user selectable graphical objects or elements corresponding to the presentation of or switching between (a) a mind state visual interface (e.g., in response to user selection of a "Thoughts" button); (b) a body state visual interface (e.g., in response to user selection of a "Purpose" button); (c) an activity intensity visual interface (e.g., in response to user selection of an "Energy" button; (d) an activity sequence and relaxation/training game selection or definition visual interface (e.g., in response to user selection of an "Action" button or a related button; (e) a mind signal and body signal selection/definition/source visual interface (e.g., in response to user selection of an "Effect" button); and (f) an FES configuration visual interface (e.g., in response to user selection of an "FES" button).

Figure 16A:
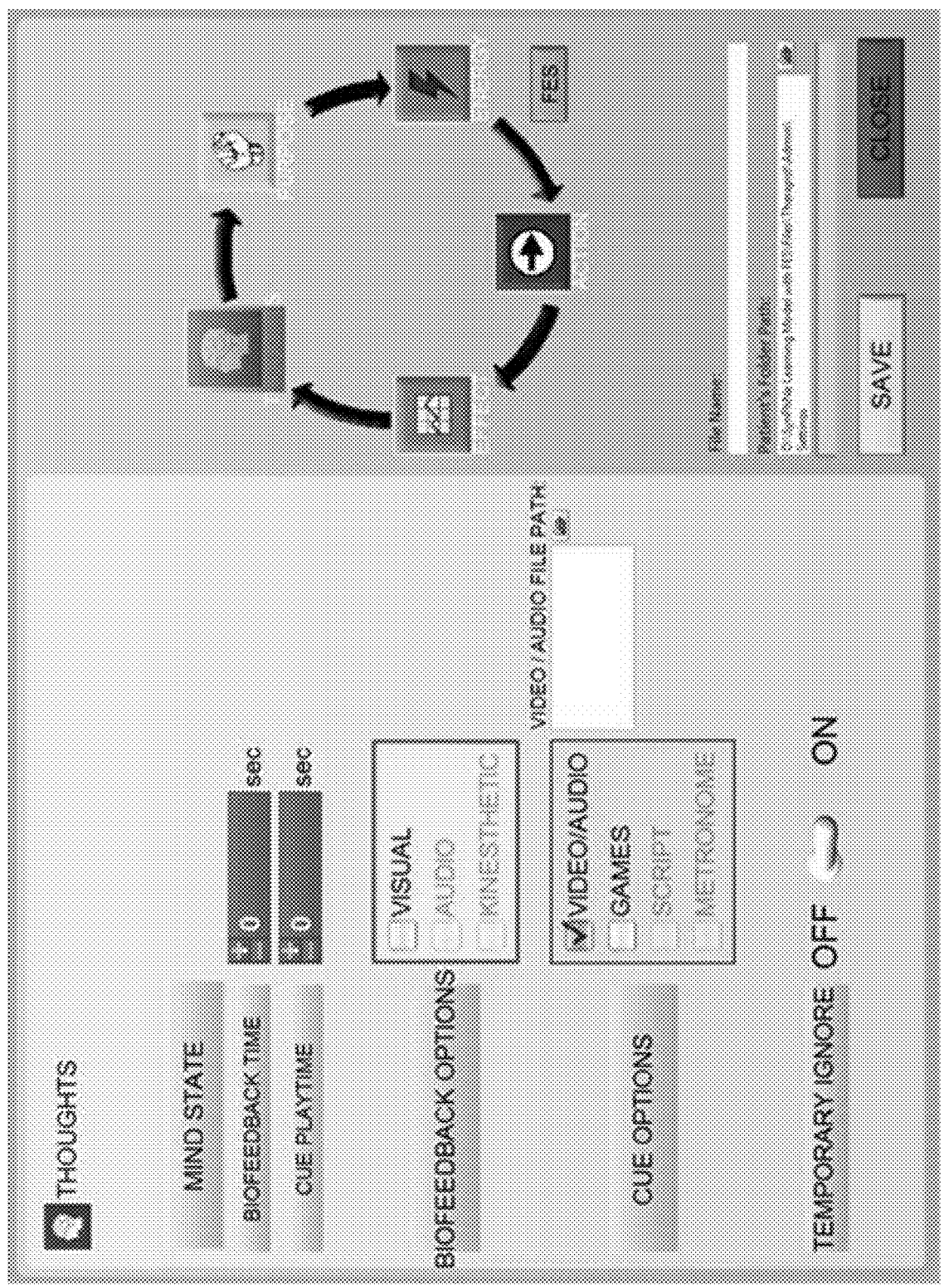

FIG. 16A is a schematic illustration of a representative visual interface for configuring system options/parameters corresponding to a subject's mind state. Such a visual interface can include graphical objects or elements configured for facilitating or receiving user input corresponding to, for instance, (a) an amount of time ("Biofeedback Time") that the system waits before automatically switching from a functional development activity/therapy session to a mind state relaxation/training routine when the subject's mind state becomes non-conducive to therapeutic benefit/gains; (b) an amount of time ("Cue Playtime") that the system presents a mind state relaxation/training routine before switching back to a therapy session; (c) options for presenting mind state biofeedback (e.g., visual, audio, kinesthetic biofeedback modes); (d) options for presenting mind state relaxation/training/adjustment cues (e.g., visual/audio, games, scripts, and metronome); and (e) whether to temporarily ignore the subject's mind state.

Figure 16B:
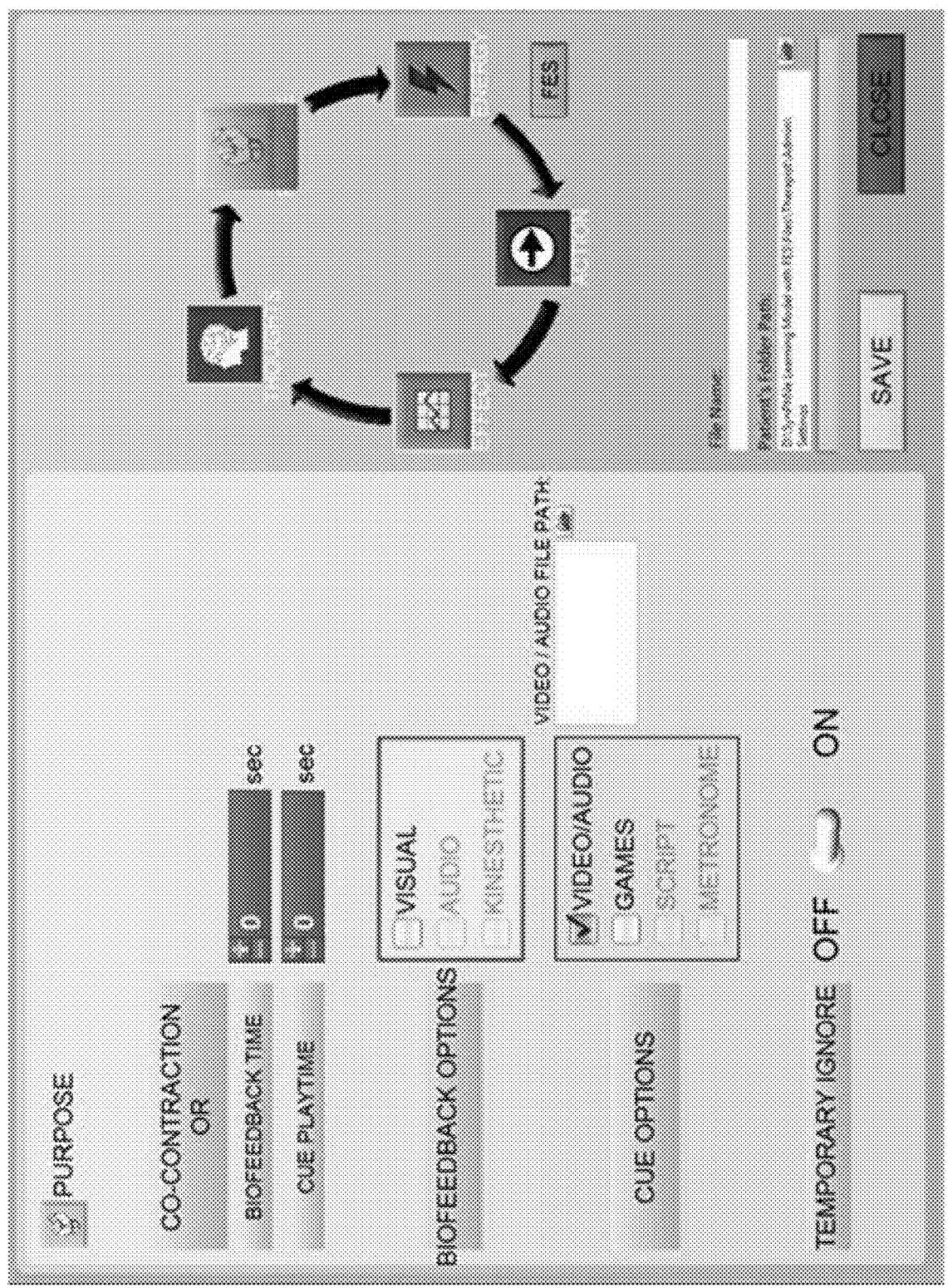

FIG. 16B is a schematic illustration of a representative visual interface for configuring system options/parameters corresponding to a subject's body state. Such a visual interface can include graphical objects or elements configured for facilitating or receiving user input corresponding to (a) an amount of time ("Biofeedback Time") that the system waits before automatically switching from a functional development activity/therapy session to a body state relaxation/training routine; (b) an amount of time ("Cue Playtime") that the system presents a body state relaxation/training routine before switching back to a therapy session; (c) options for presenting body state biofeedback; (d) options for presenting body state relaxation/training/adjustment cues; and (e) whether to temporarily ignore the subject's body state, in a manner analogous or generally analogous to that shown in FIG. 16A.

Figure 16C:
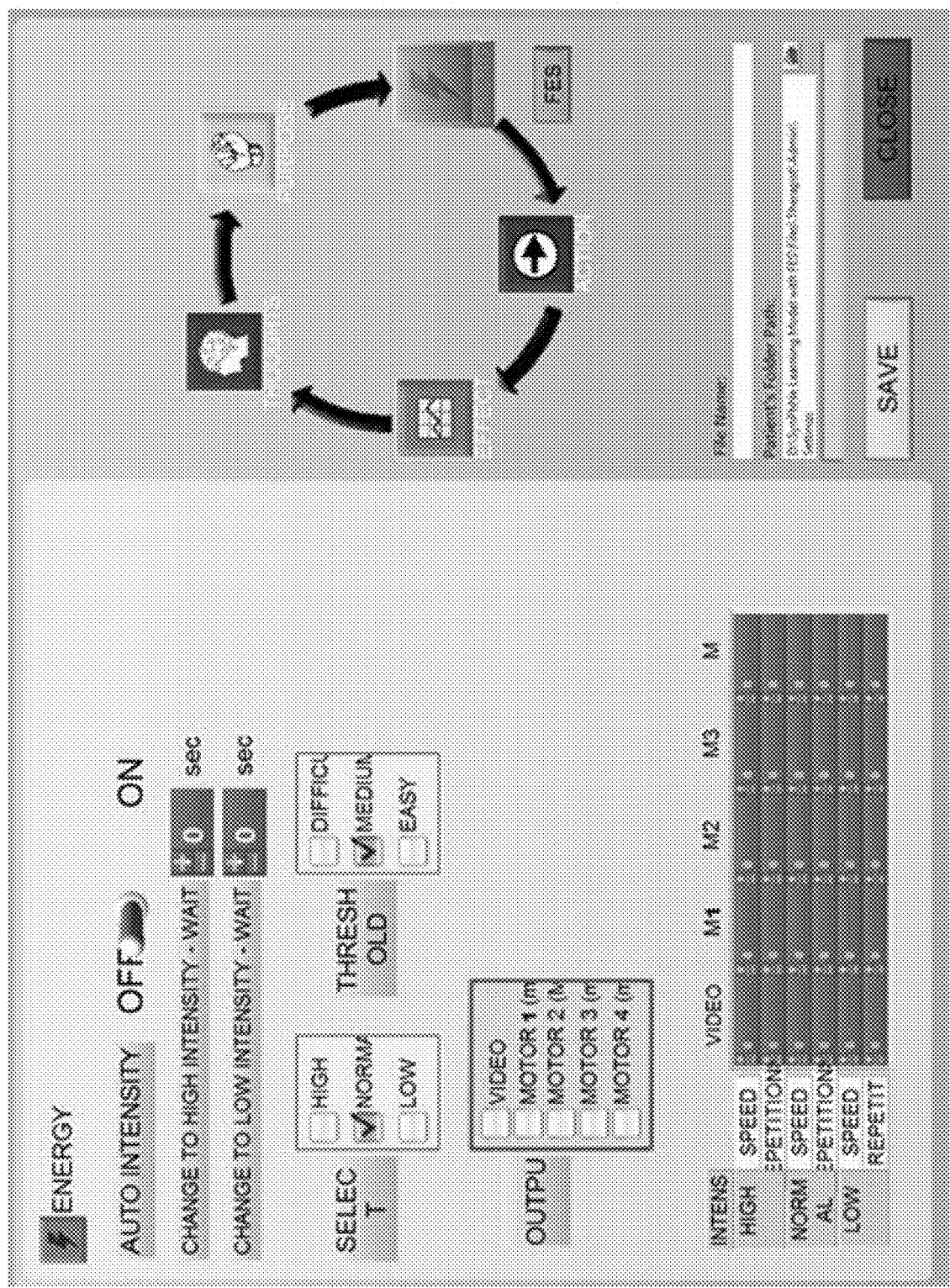

FIG. 16C is a schematic illustration of a representative visual interface for configuring activity sequence intensity parameters. Such a visual interface can include graphical objects or elements configured for facilitating or receiving user input corresponding to functional development sequence intensity, such as a wait time prior to increasing intensity; a wait time prior to decreasing intensity; high-medium/normal-low intensity selections; and speed and repetition definitions corresponding to high, medium/normal, and low intensity definitions. Such a visual interface can also include graphical objects or elements that facilitate user selection or definition of output signal parameters (e.g., pulse width modulation (PWM) parameters) for driving one or more types of external devices such as motors.

Figure 16D:
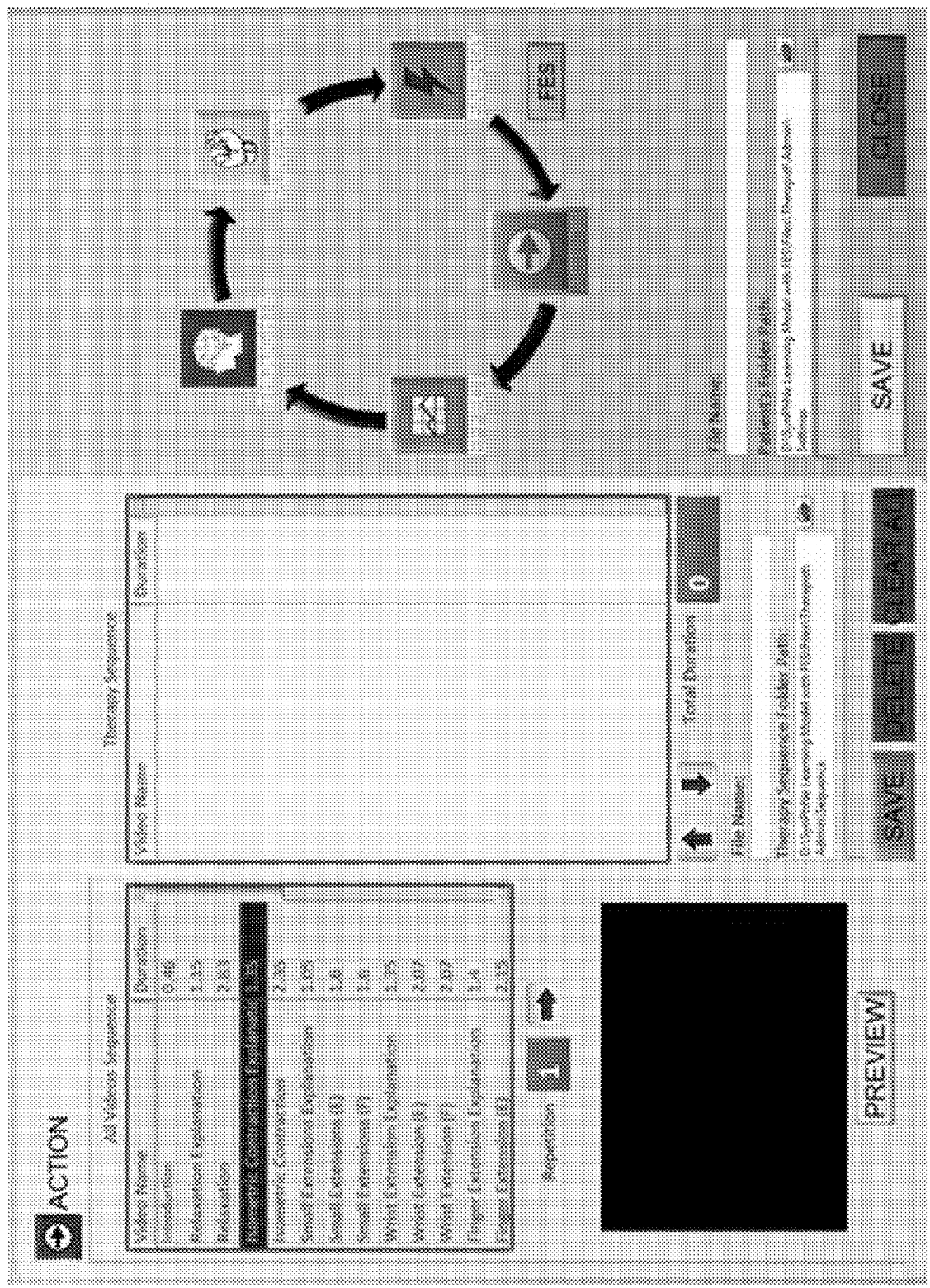
Figure 16F:
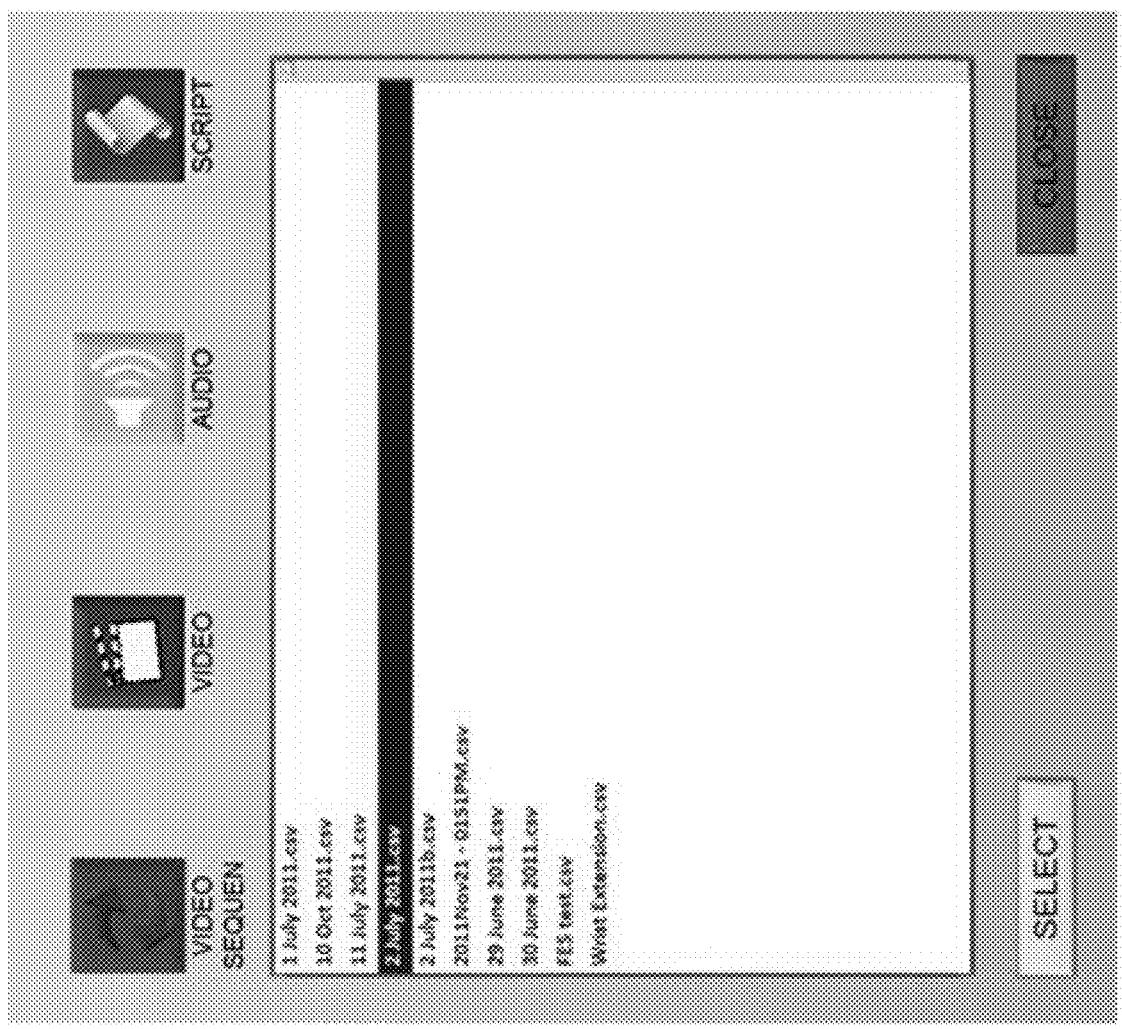
Figure 16G:
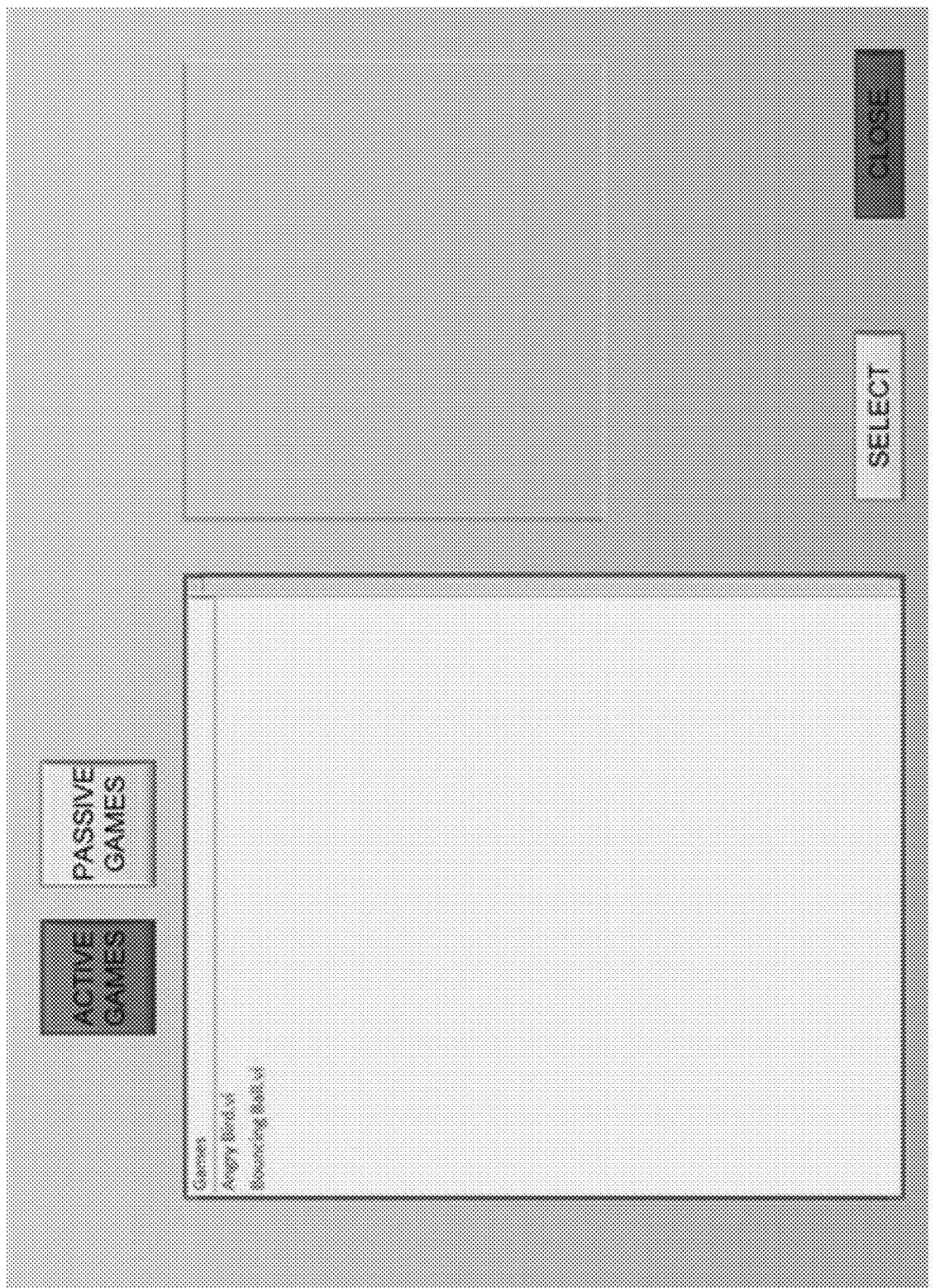

FIG. 16D is a schematic illustration of a representative visual interface for configuring activity sequence definitions. Such a visual interface can include graphical objects or elements configured for facilitating user input corresponding to functional development activity or therapy sequence definitions, such as by way of user selection/ordering of therapy videos. For any given therapy video, a corresponding table, database, or spreadsheet can establish or define muscles or muscle groups that are to be monitored in association with therapy video presentation, for instance, in a manner indicated in FIG. 16E. Defined therapy sequences can be stored in a library, such that therapy sequences corresponding to a given subject can be selected by way of a visual interface such as that shown in FIG. 16F. Selection of particular games can be facilitated by a visual interface such as that shown in FIG. 16G.

Figure 16H:
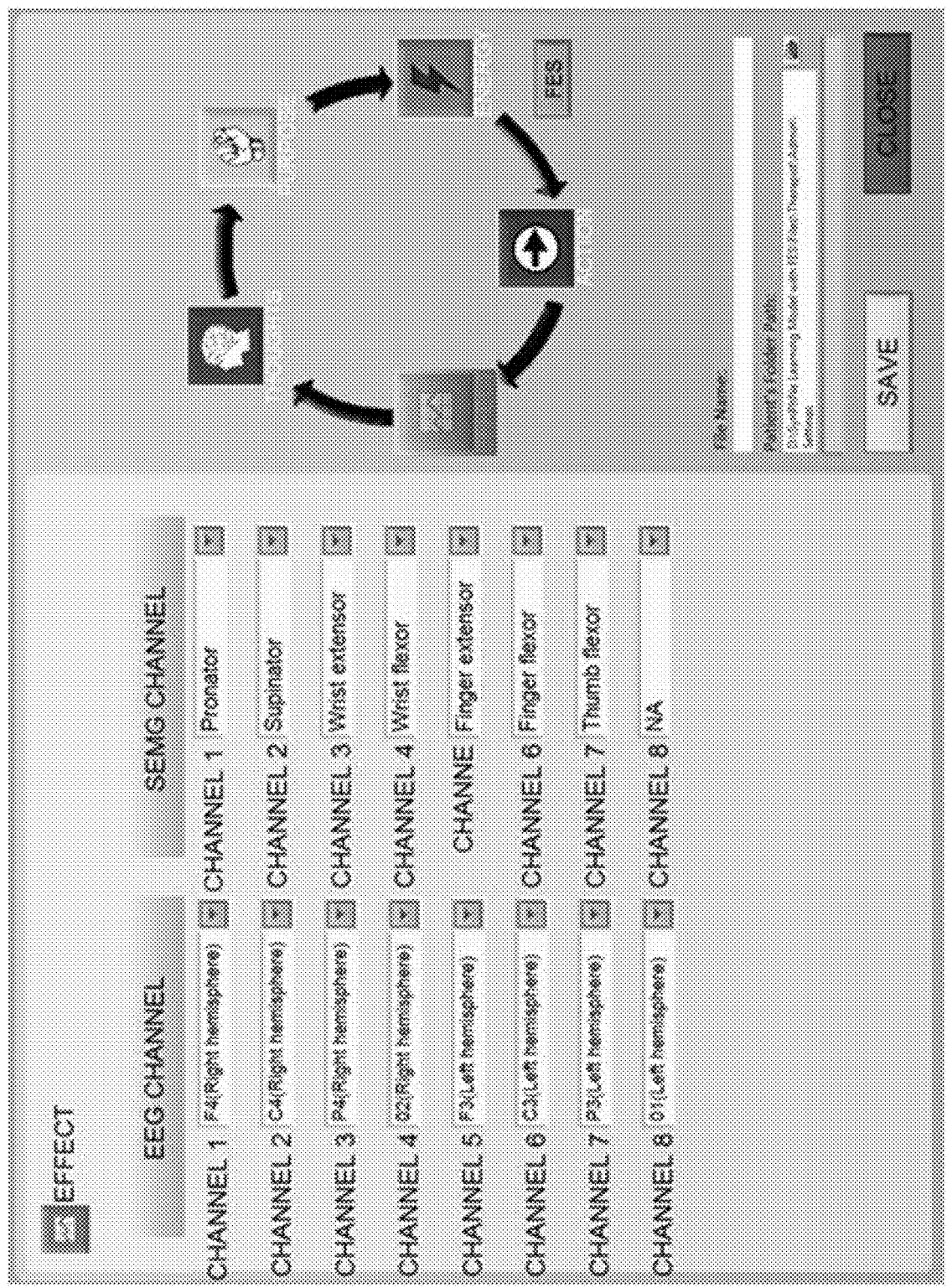

FIG. 16H is a schematic illustration of a representative visual interface for configuring or defining which mind signals and body signals are to be monitored. Such a visual interface can include graphical objects or elements that facilitate or receive user input corresponding to particular EEG channels and EMG channels.

Figure 16I:
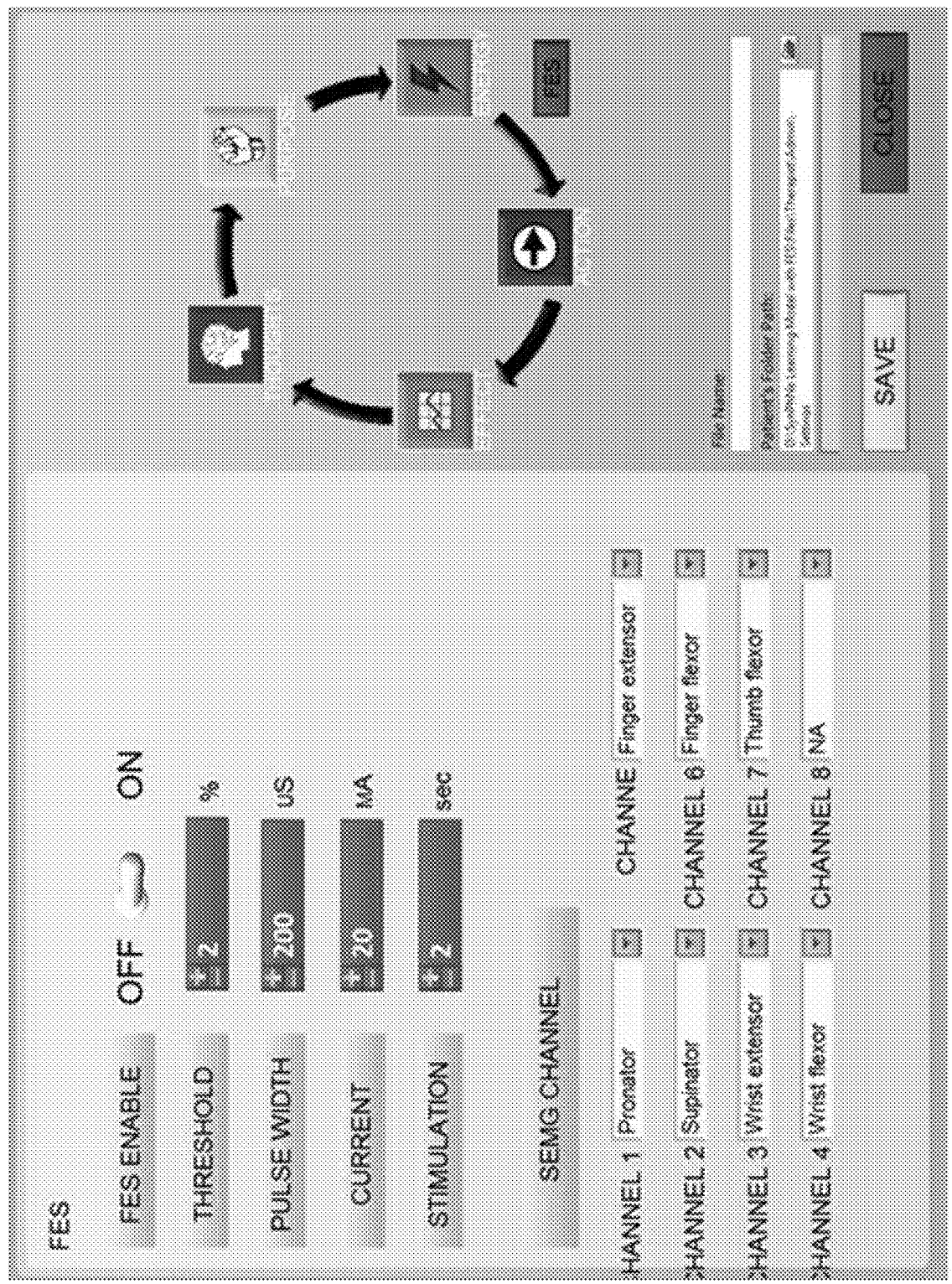

FIG. 16I is a schematic illustration of a representative visual interface for configuring or defining FES related parameters. Such a visual interface can include graphical objects or elements that facilitate or receive user input corresponding to FES signal characteristics, and EMG channels to or through which FES can be delivered.

Figure 17A:
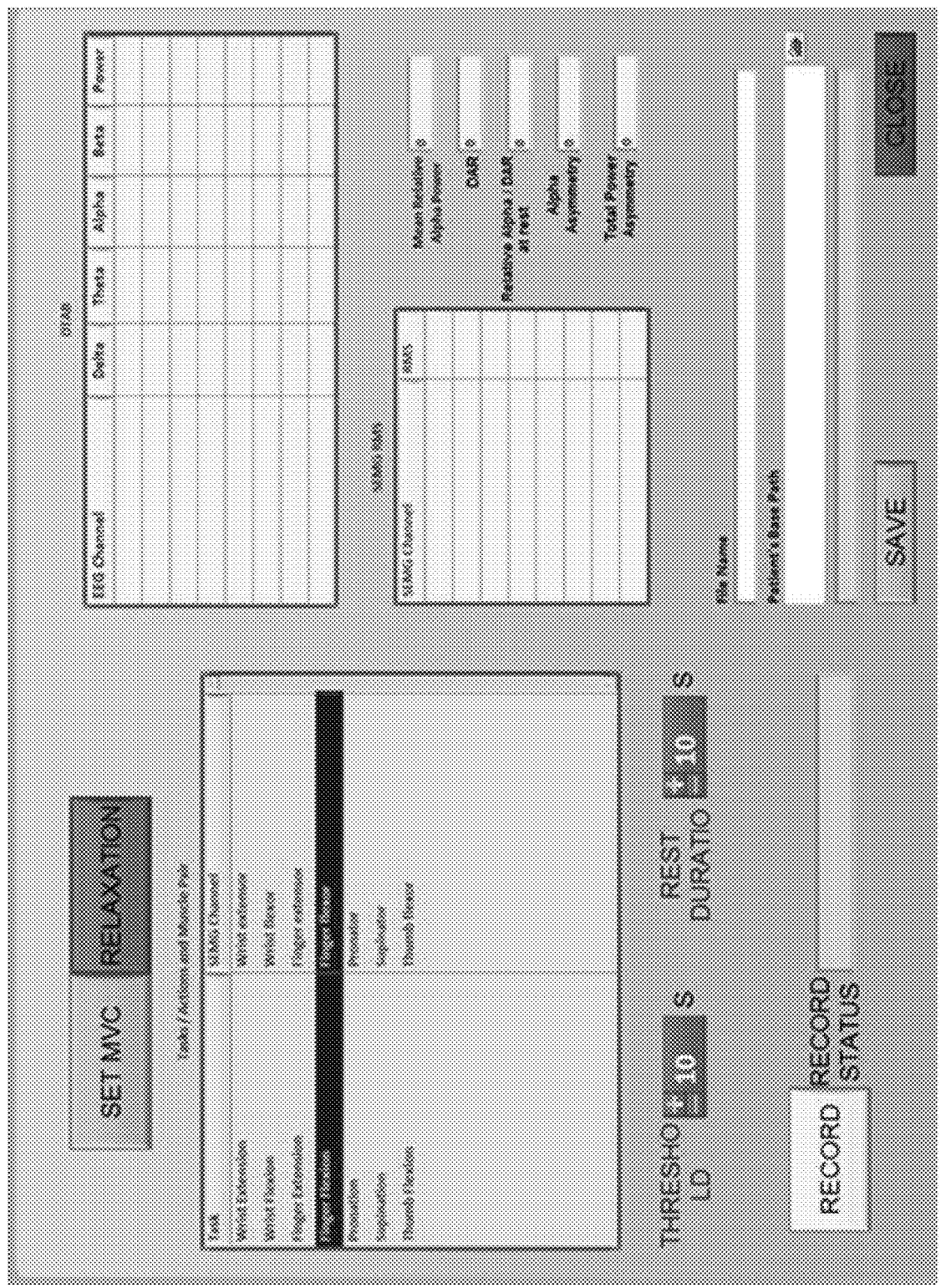
FIGS. 17A-17B are representative visual interfaces for determining system parameters associated with resting state muscle relaxation and maximum voluntary muscle contraction, respectively.
Figure 17B:
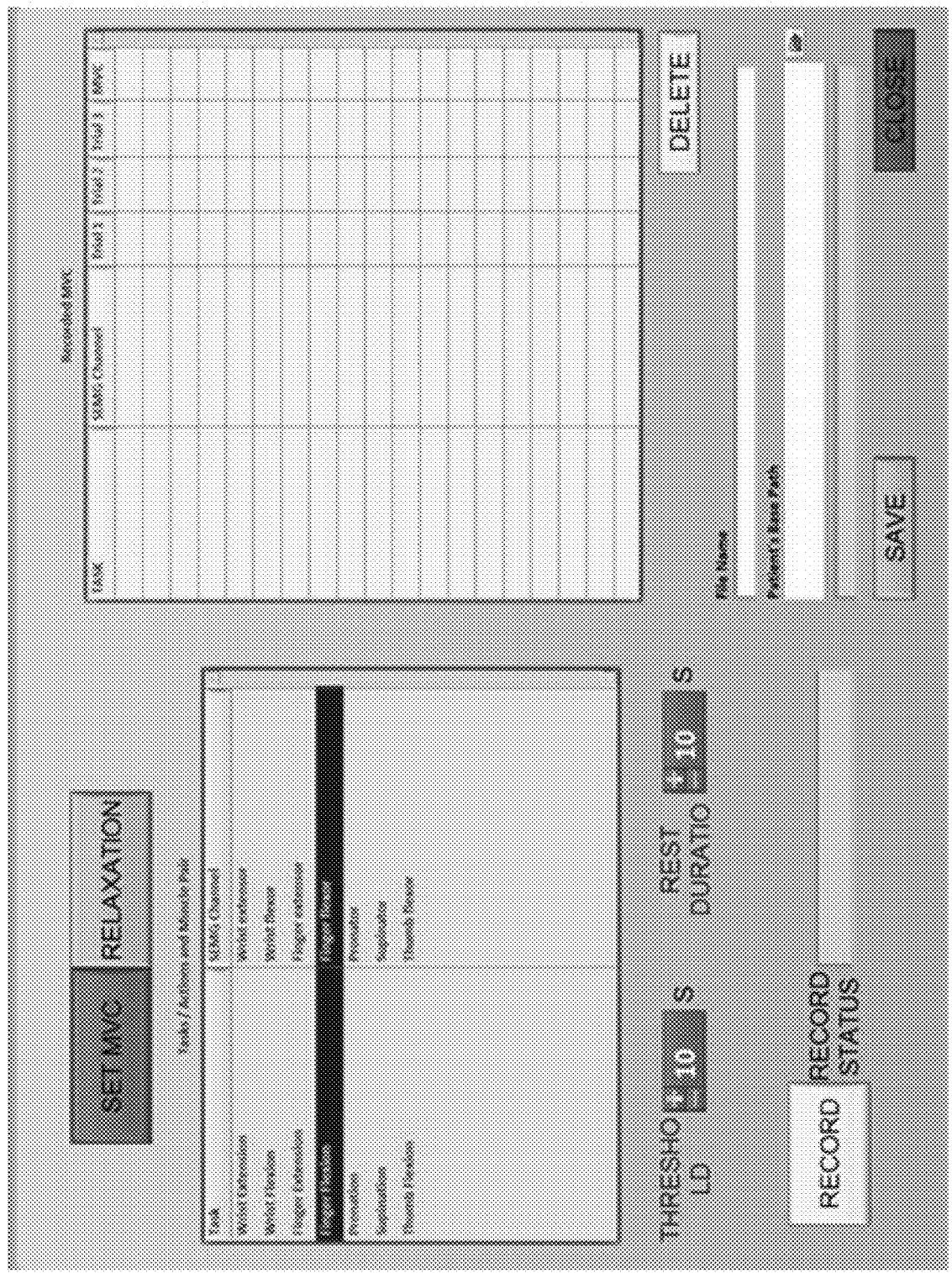

FIGS. 17A-17B are representative visual interfaces for determining system parameters associated with resting state muscle relaxation and maximum voluntary muscle contraction, respectively. More particularly, FIG. 17A is a representative visual interface that includes graphical objects or elements configured for facilitating or receiving user input directed to relaxed-state subject readings, and defining subject EEG baseline data, EMG baseline data, and asymmetry data. 17B is a representative graphical interface that includes graphical objects or elements configured for facilitating or receiving user input directed to determining maximum voluntary muscle contraction (MVC) parameters, which can be used for other calculations in one or more manners previously described.

Figure 18A:
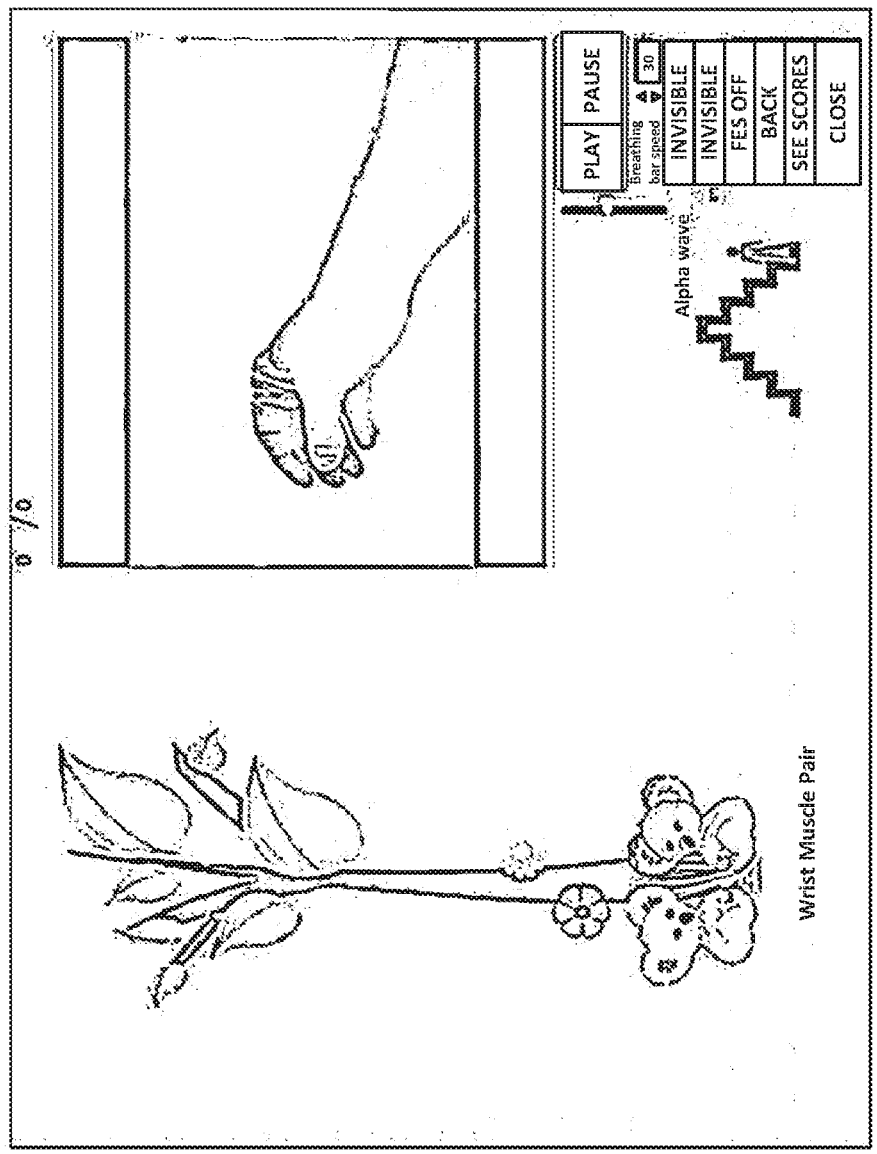
FIGS. 18A-18C are representative visual interfaces associated with subject warm-up and therapy activities.
Figure 18B:
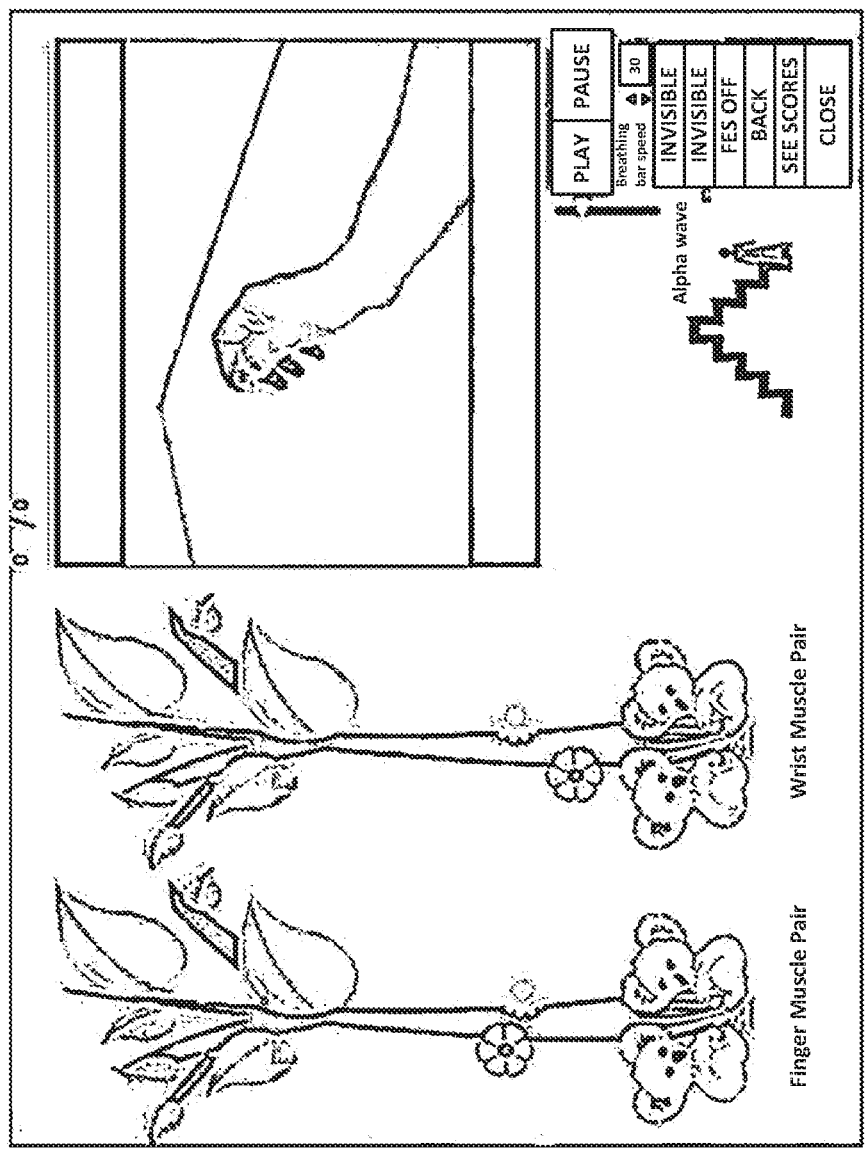
Figure 18C:
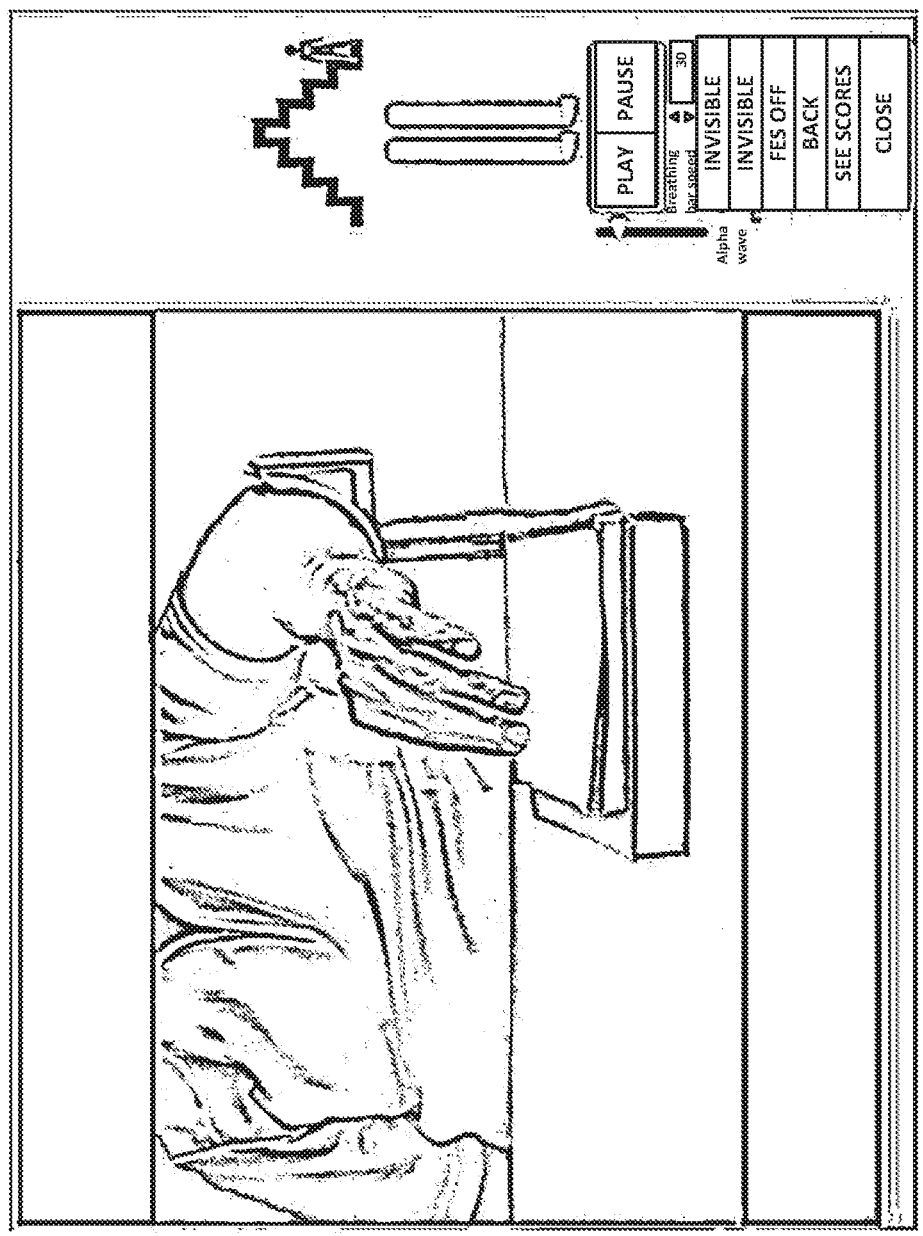

FIGS. 18A-18C are representative visual interfaces associated with subject warm-up and functional development/therapy sequence activities. Such interfaces can provide (e.g., on a predetermined or selective/selectable basis) visual representations of one or more of (a) agonist/antagonist muscle activity for one or more muscle groups under consideration (e.g., by way of a position of graphical elements such as flowers relative to a graphical object such as a tree); (b) a measure of mind state-body state alignment/integration/unification (e.g., by way of a graphical person positioned relative to the left, right, or center of a graphical pyramid); (c) a relative alpha band EEG power level; and (d) a target subject breathing rate. Such interfaces further provide windows in which videos or animations for mirror-image subject imitation/attempted imitation can be shown; and controls for selectively enabling, disabling, presenting, or controlling the visual information presented to the subject during a therapy session.

Figure 19A:
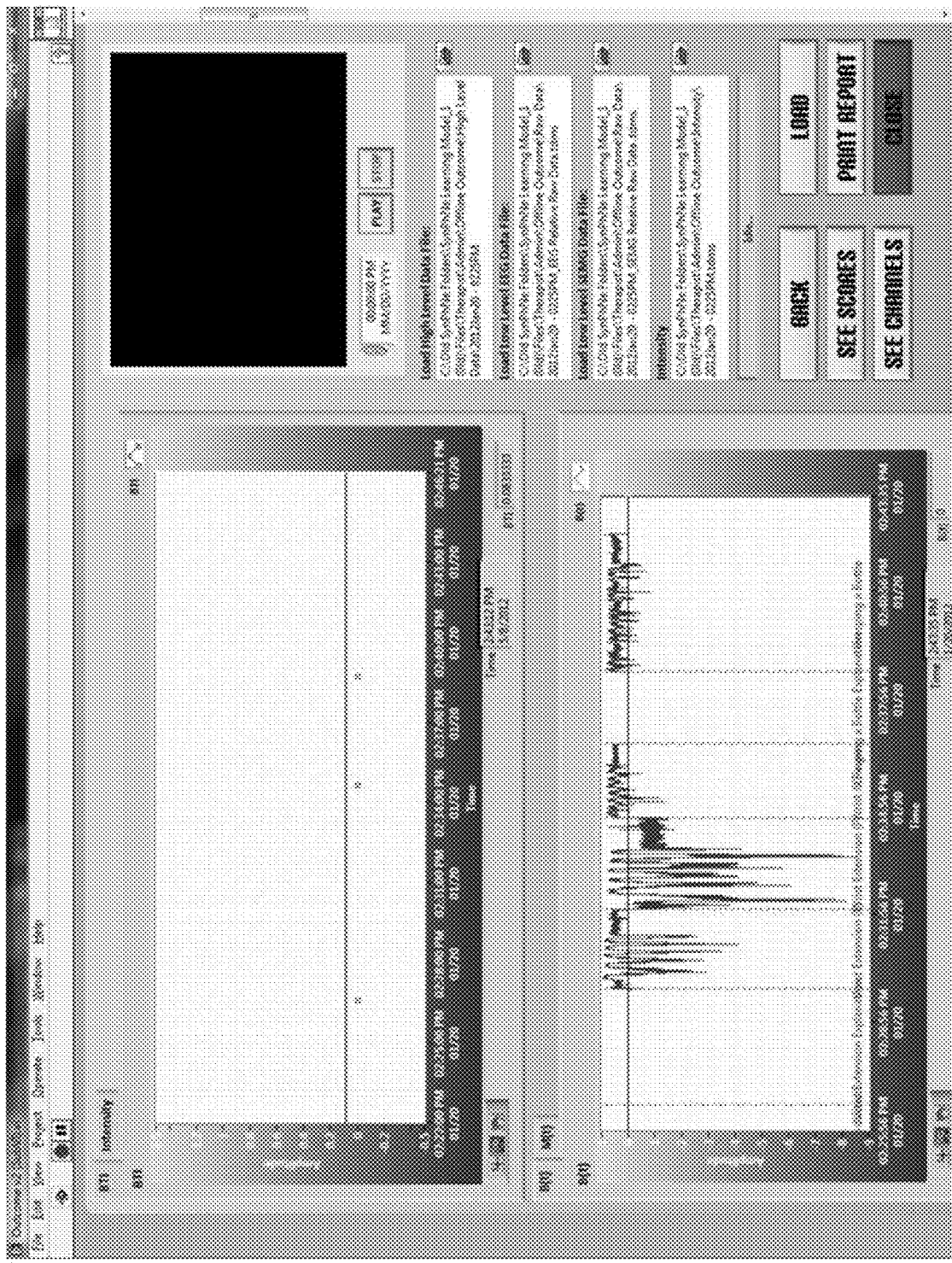
FIGS. 19A-19H are representative visual interfaces for presenting various types of subject performance metrics.
Figure 19B:
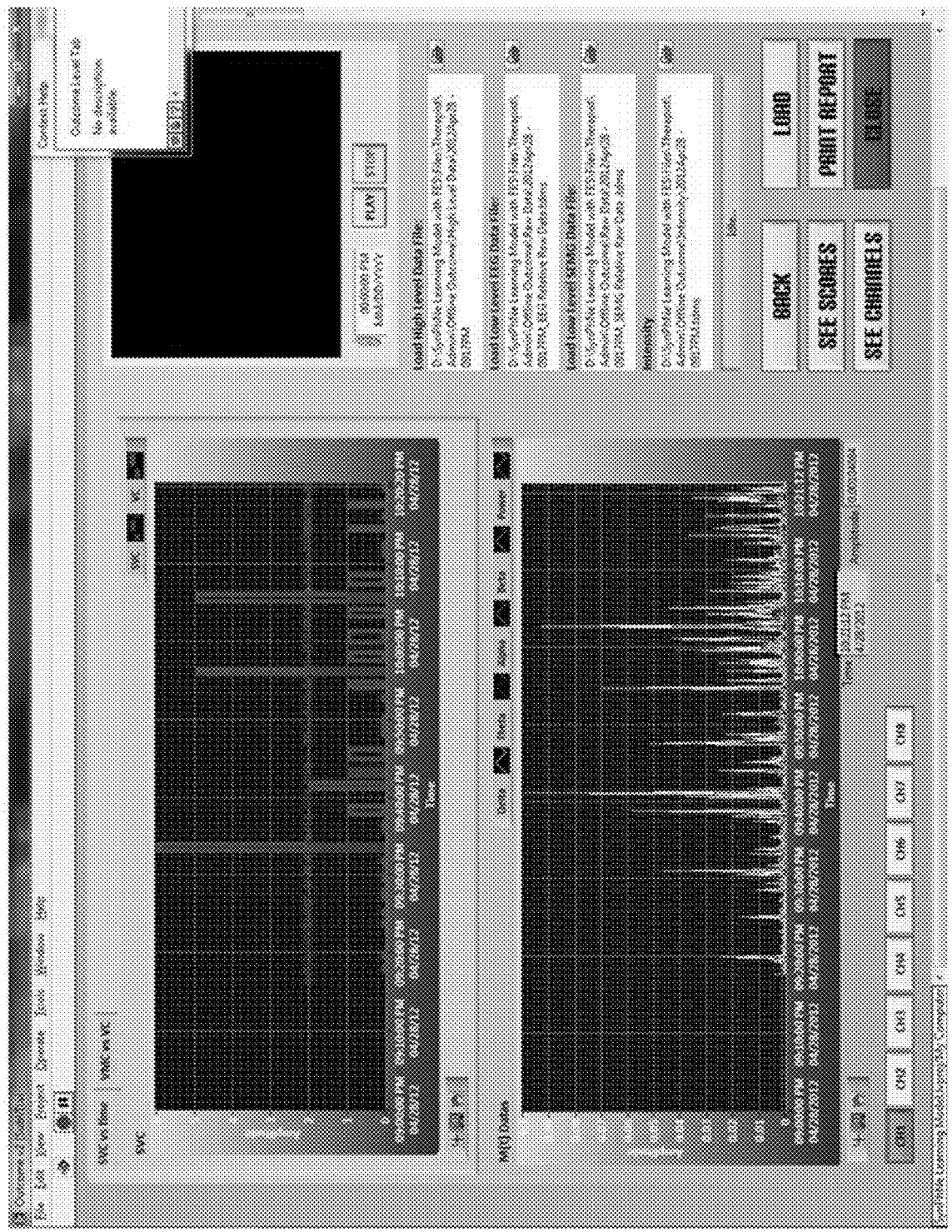
Figure 19C:
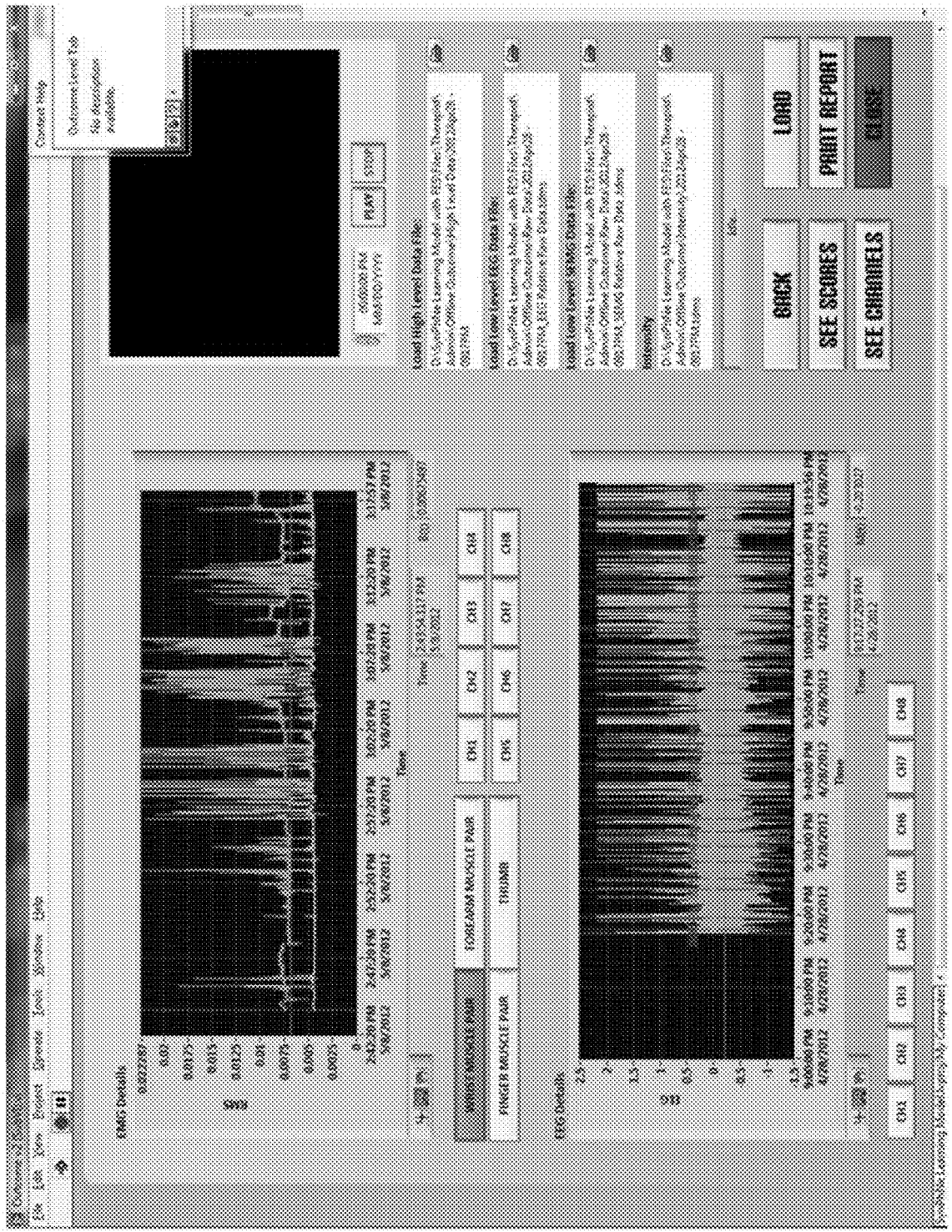
Figure 19D:
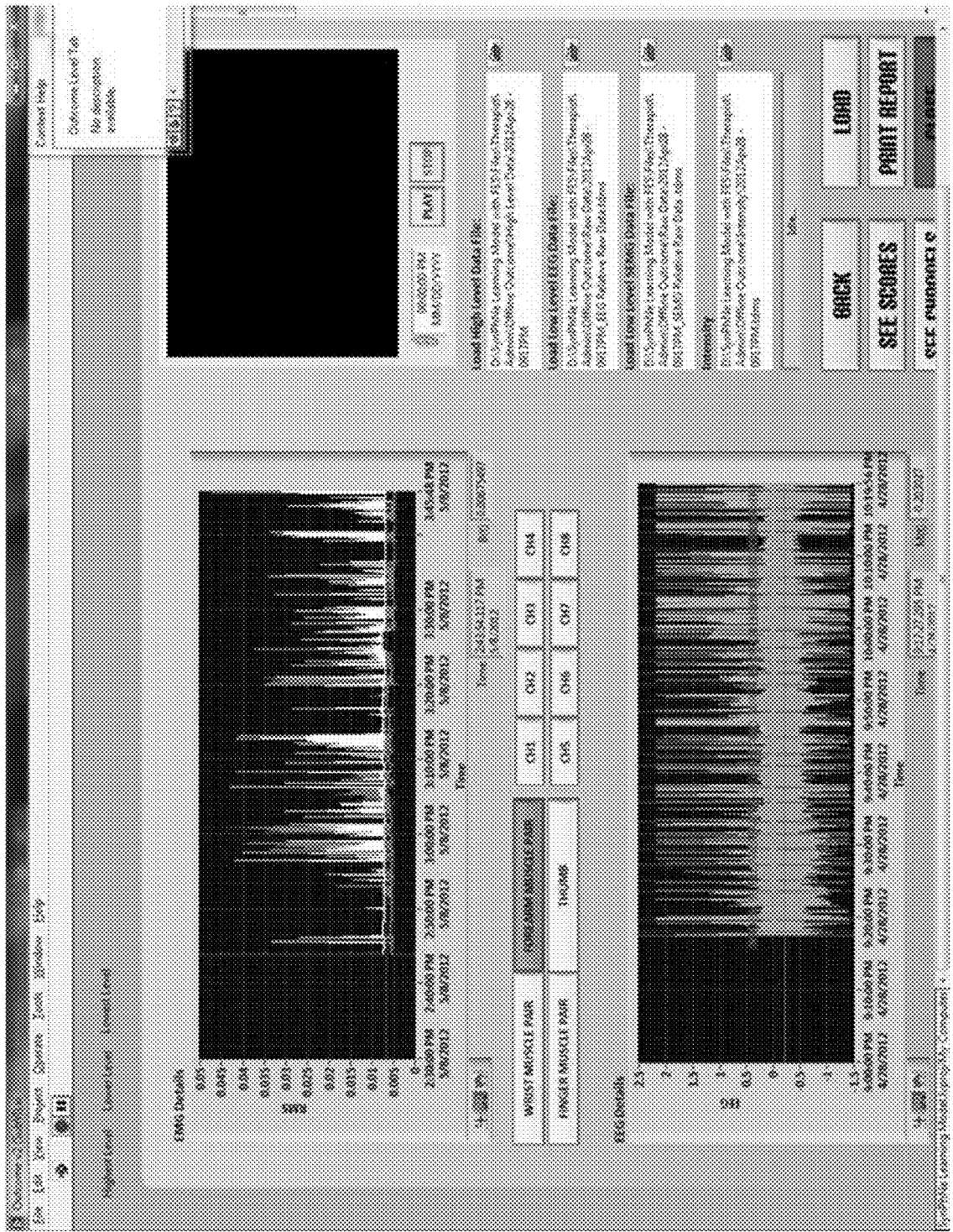
Figure 19E:
Figure 19F:
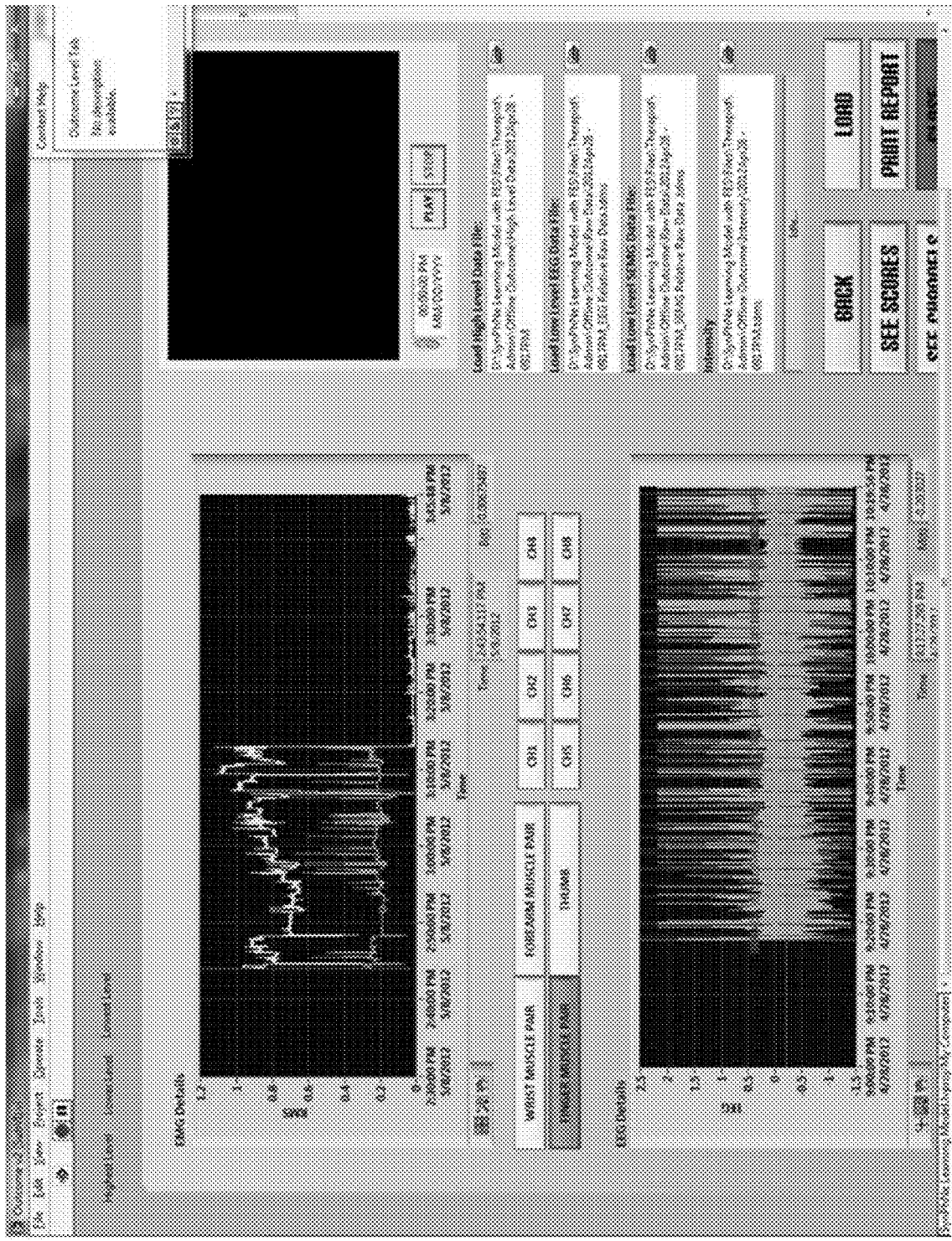
Figure 19G:
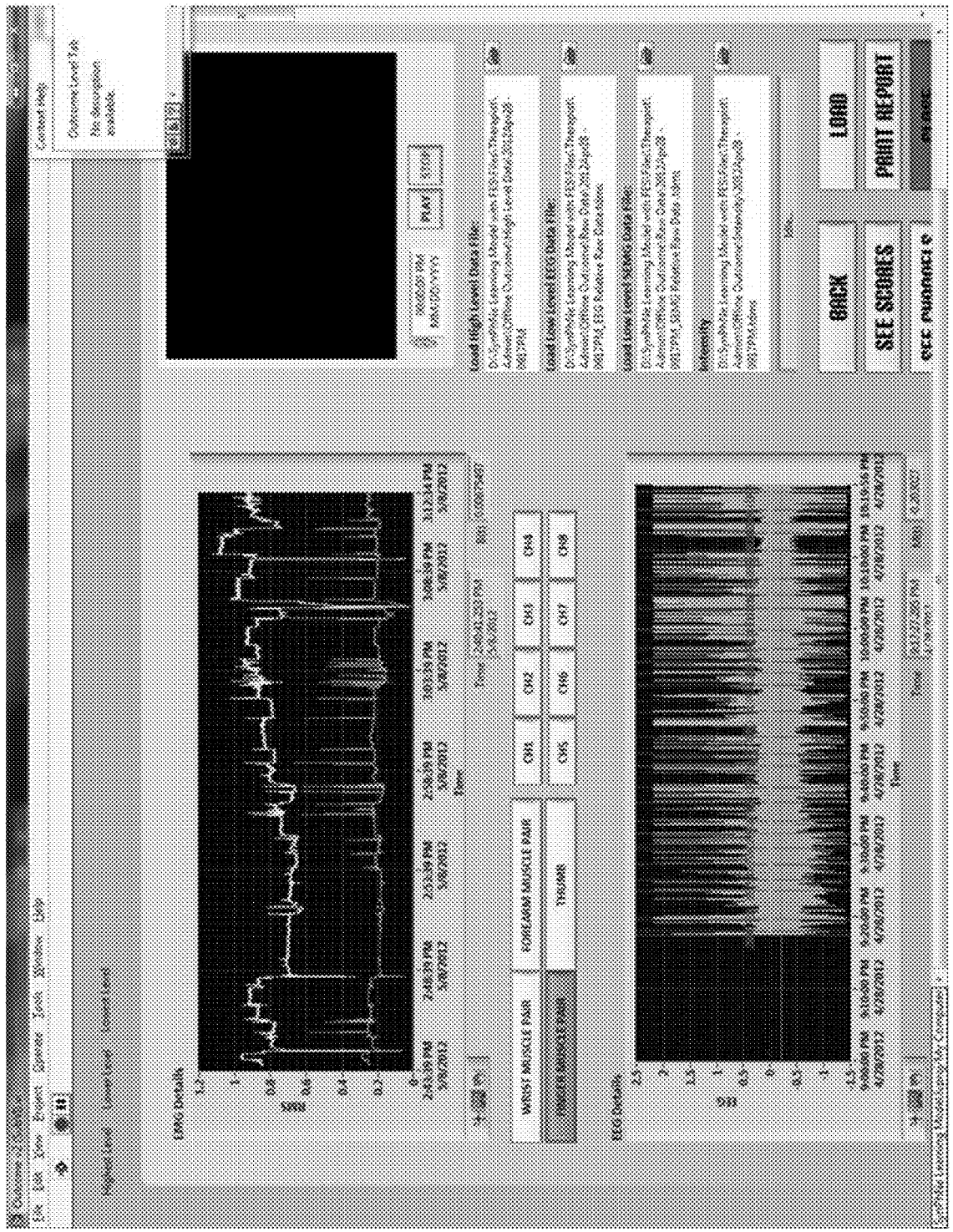
Figure 19H:
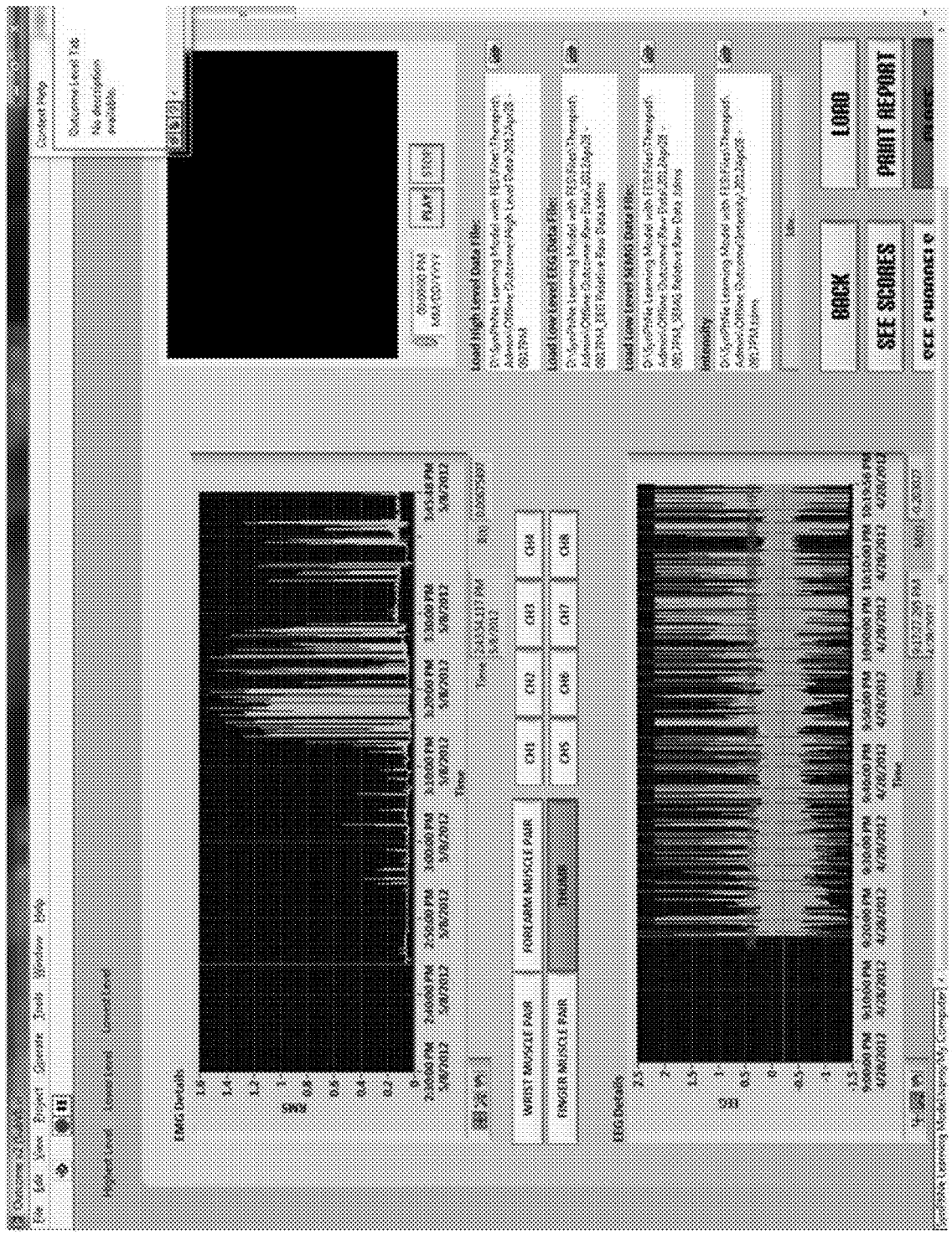
Figure 20A:
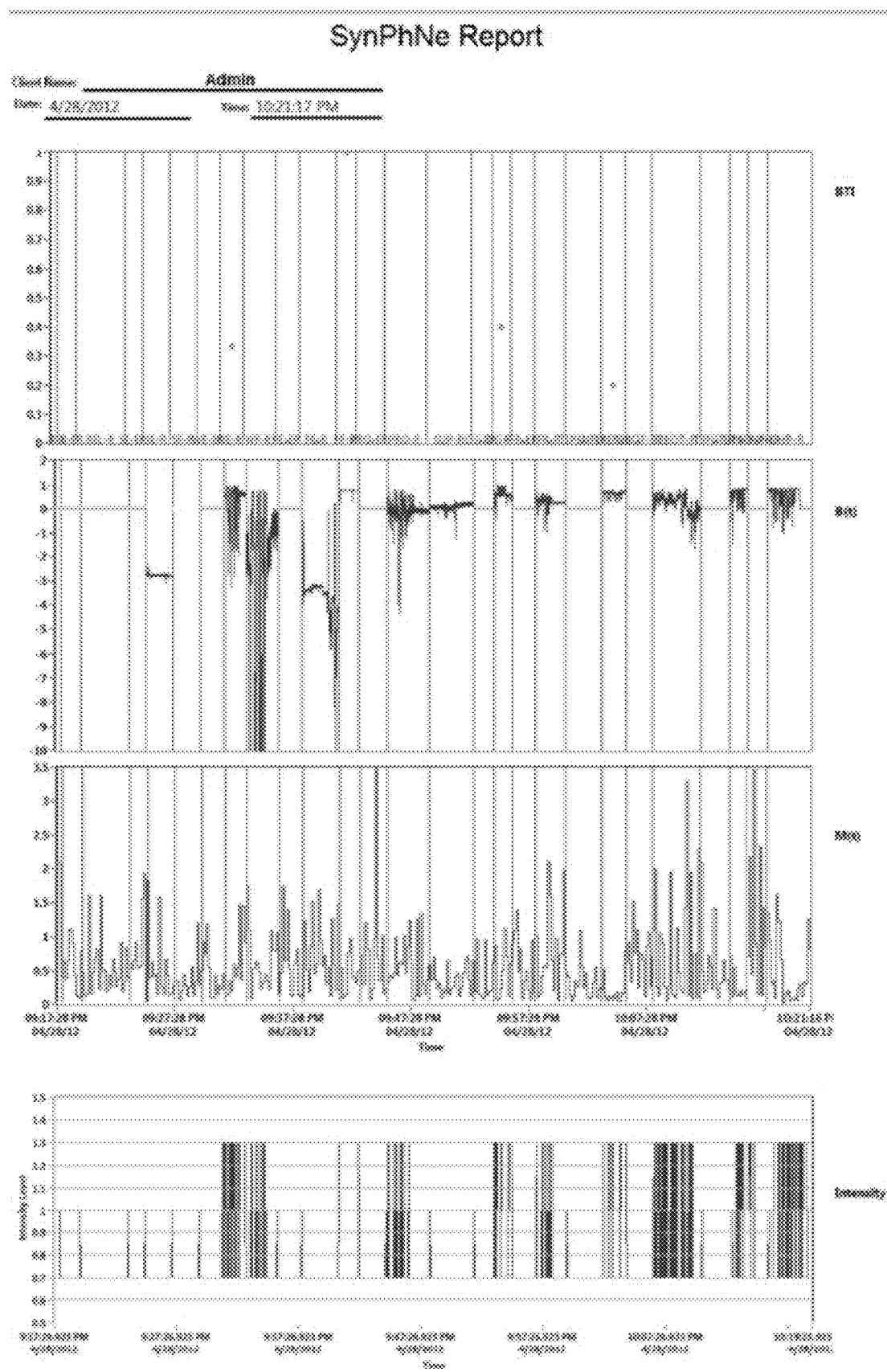
Figure 20B:
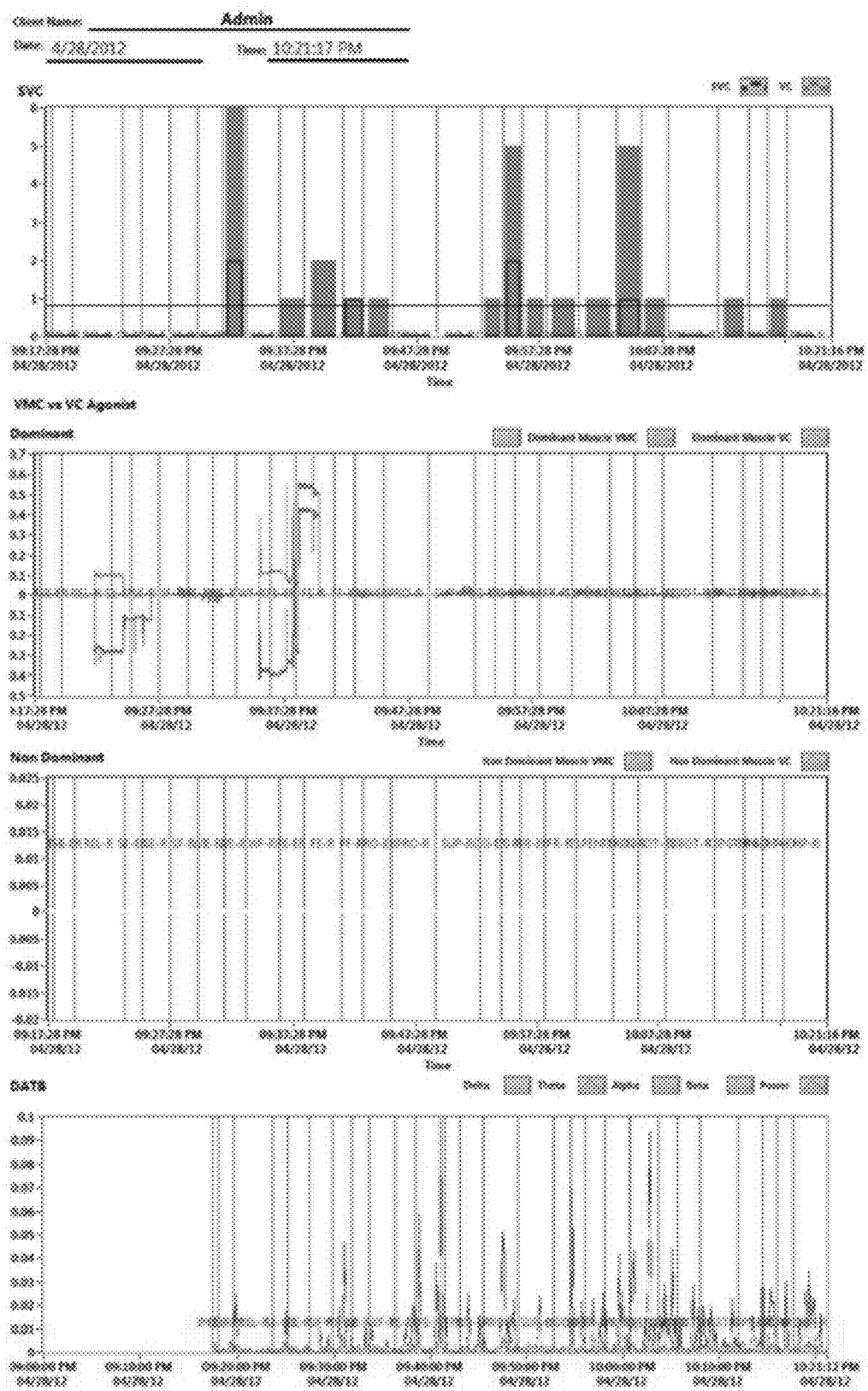

FIGS. 19A-19H are representative visual interfaces for presenting various types of subject performance metrics, which can correspond to, indicate, or represent particular types of subject mind and body activity during functional development activity sequences or activities of daily living. For instance, FIG. 19A is a visual interface by which BTI(t), intensity(t), $B_A(t)$, and $M_A(t)$ corresponding to subject activities can be presented. FIG. 19B is a visual interface by which information relating to voluntary muscle contraction and successful voluntary muscle contraction corresponding to particular EMG channels can be presented in association with $M_A(t)$ information. FIGS. 19C-19H are visual interfaces by which acquired/measured body state signals (e.g., raw rms EMG data) corresponding to particular muscles/muscle groups and acquired/measured mind state signals (e.g., raw rms EEG data) corresponding to particular EEG channels can be presented. Finally, FIGS. 20A-20C are representative reports for presenting various types of subject performance metrics. An individual such as a therapist or clinician can review and analyze information presented by way of the visual interfaces of FIGS. 19A-19H and/or FIGS. 20A-20C, and adapt, adjust, or customize one or more aspects of a given subject's therapy session(s), monitor subject progress, and identify subject functional gains/breakthroughs over time.

In view of the foregoing, various embodiments in accordance with the present disclosure are configured for providing systems, apparatuses, devices, and processes that aid functional development and/or restoration by way of a highly synergistic simultaneous combination (e.g., in a single system) of the following:
- (a) a set of visual functional development interfaces configured for presenting visual sequence (e.g., a video or an animation) of a set of body parts (e.g., one or more fingers, a hand, the wrist, the arm, and/or other body part) performing functional development/therapy activities or tasks that a subject is to imitate or attempt to imitate using a set of body parts that is the mirror image of the set of body parts presented by the set of visual functional development interfaces;
- (b) a visual feedback interface configured for conveying in a unified or simultaneous manner a visual representation (e.g., a visual BTI(t) indicator) of an extent to which each of the subject's (i) mind state (e.g., correlated with central nervous system/neurofeedback or EEG signals, such as described above in relation to $M_A(t)$ determination) and (ii) body state (e.g., correlated with peripheral nervous system/muscle state or EMG signals, such as described above in relation to $B_A(t)$ determination) are aligned, integrated, unified, or synergistically cooperative or coordinated with respect to functional development or restoration; and
- (c) visual representations of one or measures of a current level of subject relaxation, such as by way of visual indicators corresponding to relative alpha band EEG power, subject breathing rate, subject heart rate, and/or other measures of subject relaxation.

Subject functional development is further synergistically aided by one or more of:
- (d) adaptive adjustment of subject activity intensity (e.g., activity repetition count and/or speed); and
- (e) selective or adaptive transition(s) between functional development activities, mind state training sequences/exercises/games, and/or body state training sequences/exercises/games.

It is expected that embodiments in accordance with the present disclosure can facilitate the establishment and/or maintenance of a "reduced noise" or "low noise" neural activity state (e.g., by way of facilitating subject establishment and/or maintenance of an appropriately relaxed mind state and an appropriately relaxed body state) in a subject during the subject's performance or attempted performance of functional development activities, movements, or movement patterns. Embodiments in accordance with the present disclosure can further be expected to facilitate the establishment and/or maintenance of a "reduced noise" or "low noise" neural activity state in the subject during the subject's performance or attempted performance of activities of daily living.

In a "reduced noise" or "low noise" neural activity state, neural signals that are less relevant or which are not relevant or counterproductive to the development or restoration of a functional development activity, movement, or movement pattern under consideration are not expected to overwhelm, mask, dominate, or undesirably affect weaker or weak neural activity within a subject's remaining more neurofunctionally relevant and viable/weakly activated neural networks (e.g., functionally redundant or partially redundant neural networks) that can contribute to the subject's performance or attempted performance of the functional development activity, movement, or movement pattern under consideration. Embodiments in accordance with the present disclosure are thus expected to enable a subject to preferentially "tap into" and strengthen more-weakly firing neural networks that are more or most neurofunctionally relevant to the functional development activity, movement, or movement pattern under consideration during at least initial phases of the subject's functional development or restoration. Thus, neurofunctionally relevant yet weakly-firing neural networks can be preferentially strengthened and progressively become more visible with respect to their neural activity levels relative to stronger firing yet less neurofunctionally relevant neural networks.

As such more-weakly firing neural networks become progressively strengthened over time, embodiments in accordance with the present disclosure are expected to enable the subject to activate or develop additional and/or other neurofunctinally relevant neural connectivity, and/or develop new neural connectivity that further enhances the subject's ability to successfully perform functional development activities, movements, or movement patterns under consideration and/or related activities, movements, or movement patterns (e.g., by way of progressive increases in activity repetitions, activity difficulty levels, and/or variation in activity types over time). Embodiments in accordance with the present disclosure can thus facilitate or drive neuroplasticity or neural reorganization in a manner that can significantly or dramatically enhance and/or accelerate the subject's functional development. In view of the foregoing, embodiments in accordance with the present disclosure are further expected to facilitate long-lasting, essentially permanent, or permanent subject functional gains.

The establishment and/or maintenance of an appropriately relaxed subject mind state and body state, and a corresponding appropriately activated subject mind state and body state (e.g., selectively activated and/or self-corrected with respect to mind-body integration/unification/coordination/cooperation) in view of a functional development activity, movement, or movement pattern under consideration stands in contrast to prior functional development techniques such as Constraint Induced Therapy (CIT), which in general force the subject to exert a high or maximal level (e.g., a sustained high level) of physical activity over significant or prolonged periods of time without adequately considering the following:
- (a) an enhanced likelihood of functional development facilitated by subject performance or attempted performance of mirror image activities or tasks;
- (b) establishment and/or maintenance of subject mind state-body state integration, and conveying to the subject an awareness of an extent, level, or measure of their mind state-body state integration (e.g., by way of a visual indicator/metric that simultaneously encodes/conveys both mind state/neurofeedback (e.g., EEG) information and body state/body biofeedback (e.g., EMG) information); and
- (c) adaptive adjustment or selection of subject activities or tasks in view of the subject's current or recent level of mind state-body state integration.

In the foregoing manner(s), particular embodiments of the disclosure are described for addressing at least one disadvantage of prior assistive systems, devices, techniques, or processes directed to the maintenance, development, rehabilitation, or rehabilitation of subject functional capabilities. Such embodiments are not to be limited to specific forms or arrangements of parts so described and it will be apparent to one skilled in the art in view of this disclosure that numerous changes, variations, and/or modifications can be made. Embodiments disclosed herein, as well as changes, variations, and/or modifications thereto based upon concepts or teachings presented herein, are encompassed by the scope of the following claims.

The invention claimed is:

1. A system for facilitating rehabilitation of a body part of a subject, the system comprising:
a first set of sensing devices configured for sensing signals corresponding to the subject's mind state;
a second set of sensing devices configured for sensing signals corresponding to the subject's body state; a subject interaction unit comprising a set of display devices configured for providing a visual interface to the subject, the visual interface comprising:
a biofeedback interface configured for presenting biofeedback to the subject while the first set of sensing devices senses signals corresponding to the subject's mind state and the second set of sensing devices senses signals corresponding to the subject's body state, the biofeedback comprising a visual representation of a measure of subject relaxed mental attention, and a visual representation of a measure of subject bodily tension, and
a functional development activity sequence interface configured for presenting a set of functional development activities to the subject while the biofeedback interface presents the biofeedback to the subject, wherein the set of functional development activities shows at least one target movement of a model body part that is a mirror image of the subject body part;
a set of processing resources, wherein the set of processing resources is configured for generating:
a mind state alignment measure indicating whether the subject's mind state is conducive to learning,
a body state alignment measure indicating the subject's body state is conducive to successfully perform the set of functional development activities, and
a mind-body synergy measure correlated with a voluntary muscle contraction measure that meets or exceeds a threshold muscle contraction condition, and which is temporally associated with each of the mind statement alignment measure satisfying a mind state alignment condition and the body state alignment measure satisfying a body state alignment condition;
at least one of a robotic orthosis configured for providing movement assistance to the subject and a functional electrical stimulation (FES) apparatus configured for delivering FES signals to the subject;
wherein the biofeedback interface is configured for providing a visual representation of the mind state alignment measure and a visual representation of the body state alignment measure; and
wherein the visual interface is configured for selectively presenting mind state training exercises to the subject following processing unit determination that a subject muscle contraction relevant to performing the set of functional development activities has occurred and the subject's mind state is not conducive to learning, and body state training exercises to the subject following processing unit determination that the subject's mind state is conducive to learning and the subject's body state is not conducive to successfully perform the set of functional development activities.

2. The system of claim 1, wherein the mind-body synergy measure includes a breakthrough index (BTI) which quantitatively measures a likelihood that the subject can experience an accelerated or burst type functional development result, wherein the BTI is calculated as a cumulative number of voluntary muscle contractions for the body part during a time period T that (i) meet or exceed the threshold muscle contraction condition for the body part, and which (ii) are each temporally associated with each of the mind state alignment measure satisfying a mind state alignment condition and the body state alignment measure satisfying a body state alignment condition, normalized to a cumulative number of voluntary muscle contractions for the body part during the time period T that meet or exceed the threshold muscle contraction condition.

3. The system of claim 1, wherein the mind state alignment measure is determined based on a real time or near-real time basis.

4. The system of claim 1, wherein the body state alignment measure is determined based on a real time or near-real time basis.

5. The system of claim 1, wherein the first set of sensing devices comprises a set of devices configured for detecting signals representative of intracranial neural activity.

6. The system of claim 1, wherein the second set of sensing devices comprises a set of devices configured for detecting signals corresponding to peripheral nervous system activity.

7. The system of claim 1, wherein the mind state alignment measure corresponds to at least one of a level of stress, a level of anxiety, a level of mental relaxation, and a level of mental attention or focus.

8. The system of claim 7, wherein the mind state alignment measure is correlated with a ratio between a mean relative alpha band power measure $P\alpha$, and a delta-to-alpha measure DAR referenced to a particular time t, normalized to a baseline or at rest ratio between the mean relative alpha measure $P\alpha$, and the delta-to-alpha measure DAR.

9. The system of claim 1, wherein the body state alignment measure mathematically defines an extent to which subject agonist muscle contractions relevant to the set of functional development activities including a movement sequence under consideration at time t are dominant or subordinate with respect to subject antagonist muscle contraction counterproductive to the movement sequence under consideration at time t for the set of functional development activities.

10. A system for facilitating rehabilitation of a body part of a subject, the system comprising:
a first set of sensing devices configured for sensing signals corresponding to the subject's mind state;
a second set of sensing devices configured for sensing signals corresponding to the subject's body state;
a subject interaction unit comprising a set of display devices configured for providing a visual interface to the subject, the visual interface comprising
a biofeedback interface configured for presenting biofeedback to the subject while the first set of sensing devices senses signals corresponding to the subject's mind state and the second set of sensing devices senses signals corresponding to the subject's body state, the biofeedback comprising (i) a visual representation of a measure of subject relaxed mental attention, and (ii) a visual representation of a measure of subject bodily tension,
a functional development activity sequence interface configured for presenting a set of functional development activities to the subject while the biofeedback interface presents the biofeedback to the subject, wherein the set of functional development activities shows at least one target movement of a model body part that is a mirror image of the subject body part;

a set of processing resources, wherein the set of processing resources is configured for generating each of a mind state alignment measure indicating whether the subject's mind state is conducive to learning, a body state alignment measure indicating whether the subject's body state is conducive to successfully perform the set of functional development activities, and a mind-body synergy measure correlated with a voluntary muscle contraction measure that (i) meets or exceeds a threshold muscle contraction condition, and which (ii) is temporally associated with each of the mind state alignment measure satisfying a mind state alignment condition and the body state alignment measure satisfying a body state alignment condition;

at least one of a robotic orthosis configured for providing movement assistance to the subject;

wherein the biofeedback interface is configured for providing a visual representation of the mind state alignment measure and a visual representation of the body state alignment measure;

wherein the visual interface is configured for selectively presenting mind state training exercises to the subject following processing unit determination that a subject muscle contraction relevant to performing the set of functional development activities has occurred and the subject's mind state is not conducive to learning, and body state training exercises to the subject following processing unit determination that the subject's mind state is conducive to learning and the subject's body state is not conducive to successfully perform the set of functional development activities.

11. The system of claim 10, wherein the mind-body synergy measure that includes a breakthrough index (BTI) which quantitatively measures a likelihood that the subject can experience an accelerated or burst type functional development result, wherein the BTI is calculated as a cumulative number of voluntary muscle contractions for the body part during a time period T that (i) meet or exceed a threshold muscle contraction condition for the body part, and which (ii) are each temporally associated with each of the mind state alignment measure satisfying a mind state alignment condition and the body state alignment measure satisfying a body state alignment condition, normalized to a cumulative number of voluntary muscle contractions for the body part during the time period T that meet or exceed the threshold muscle contraction condition.

12. The system of claim 10, wherein the mind state alignment measure and the body state alignment measure are determined based on a real time or near-real time basis.

13. The system of claim 10 further comprises a functional electrical stimulation (FES) apparatus configured for delivering FES signals to the subject.

14. The system of claim 10, wherein the first set of sensing devices comprises a set of devices configured for detecting signals representative of intracranial neural activity.

15. The system of claim 10, wherein the second set of sensing devices comprises a set of devices configured for detecting signals corresponding to peripheral nervous system activity.

16. The system of claim 10, wherein the mind state alignment measure corresponds to at least one of a level of stress, a level of anxiety, a level of mental relaxation, and a level of mental attention or focus.

17. The system of claim 10, wherein the mind state alignment measure is correlated with a ratio between a mean relative alpha band power measure $P\alpha$, and a delta-to-alpha measure DAR referenced to a particular time t, normalized to a baseline or at rest ratio between the mean relative alpha measure $P\alpha$, and the delta-to-alpha measure DAR.

18. The system of claim 10, wherein the body state alignment measure mathematically defines an extent to which subject agonist muscle contractions relevant to the set of functional development activities including a movement sequence under consideration at time t are dominant or subordinate with respect to subject antagonist muscle contraction counterproductive to the movement sequence under consideration at time t for the set of functional development activities.

19. A method for facilitating rehabilitation of a body part of a subject, the method comprising:

mounting a wearable robotic orthosis to a portion of a subject appendage;

providing assistive movement to the subject appendage by way of the wearable robotic orthosis during subject performance or attempted performance of a functional development activity sequence;

sensing signals corresponding to the subject's mind state;

sensing signals corresponding to the subject's body state;

providing a visual interface showing the subject biofeedback corresponding to the subject's mind and/or body state through a biofeedback interface and a set of functional development activities through a functional development activity sequence interface, the biofeedback comprising a visual representation of a measure of subject relaxed mental attention and a visual representation of a measure of subject bodily tension, the set of functional development activities including showing at least one target movement of a model body part that is a mirror image of the subject body part;

generating a mind state alignment measure indicating whether the subject's mind state is conducive to learning, a body state alignment measure indicating whether the subject's mind state is conducive to successfully perform a set of functional development activities, and a mind-body synergy measure correlated with a voluntary muscle contraction measure that meets or exceeds a threshold muscle contraction condition, and which is temporally associated with each of the mind statement alignment measure satisfying a mind state alignment condition and each of the body state alignment measure satisfying a body state alignment condition;

presenting selectively mind state training exercise to the subject following processing unit determination that a subject muscle contraction relevant to performing the set of functional development activities has occurred and the subject's mind state is not conducive to learning, and body state training exercises to the subject following processing unit determination that the subject's mind state is conducive to learning and the subject's body state is not conducive to successfully performing the set of functional development activities; and performing the set of functional development activities for rehabilitation of the body part of the subject, wherein the biofeedback interface is configured for providing a visual representation of the mind state alignment measure and a visual representation of the body state alignment measure.

20. The method of claim 19, wherein the robotic orthosis comprises:
a set of appendage motion modules configured for engaging with a portion of a subject appendage;
a set of mechanical power interface modules coupled to the set of appendage motion modules and configured for facilitating movement of appendage motion modules within the set of appendage motion modules; and
a set of flexible drive shafts couplable to the set of mechanical power interface modules and a set of motors external to the wearable robotic orthosis, wherein the set of appendage motion modules and the set of mechanical power interface modules are subject wearable.

21. The method of claim 20, wherein the set of appendage motion modules includes multiple independently operable and selectively detachable appendage motion modules.

22. The method of claim 19, wherein the mind-body synergy measure that includes a breakthrough index (BTI) which quantitatively measures a likelihood that the subject can experience an accelerated or burst type functional development result, wherein the BTI is calculated as a cumulative number of voluntary muscle contractions for the body part during a time period T that (i) meet or exceed a threshold muscle contraction condition for the body part, and which (ii) are each temporally associated with each of the mind state alignment measure satisfying a mind state alignment condition and the body state alignment measure satisfying a body state alignment condition, normalized to a cumulative number of voluntary muscle contractions for the body part during the time period T that meet or exceed the threshold muscle contraction condition.

23. The method of claim 19, wherein the mind state alignment measure is determined based on a real time or near-real time basis.

24. The method of claim 19, wherein the body state alignment measure is determined based on a real time or near-real time basis.

25. The method of claim 19, wherein the sensing signals corresponding to the subject's mind state comprises detecting signals representative of intracranial neural activity.

26. The method of claim 19, wherein the sensing signals corresponding to the subject's mind state comprises sensing EEG signals.

27. The method of claim 19, wherein the sensing signals corresponding to the subject's body state comprises detecting signals corresponding to peripheral nervous system activity.

28. The method of claim 19, wherein the sensing signals corresponding to the subject's body state comprises sensing EMG signals.

29. The method of claim 19, wherein the mind state alignment measure corresponds to at least one of a level of stress, a level of anxiety, a level of mental relaxation, and a level of mental attention or focus.

30. The method of claim 19, wherein the mind state alignment measure is correlated with a ratio between a mean relative alpha band power measure $P\alpha$, and a delta-to-alpha measure DAR referenced to a particular time t, normalized to a baseline or at rest ratio between the mean relative alpha measure $P\alpha$, and the delta-to-alpha measure DAR.

31. The method of claim 19, wherein the body state alignment measure mathematically defines an extent to which subject agonist muscle contractions relevant to the set of functional development activities including a movement sequence under consideration at time t are dominant or subordinate with respect to subject antagonist muscle contraction counterproductive to the movement sequence under consideration at time t for the set of functional development activities.

32. The method of claim 19 further comprises providing a functional electrical stimulation (FES) apparatus configured for delivering FES signals to the subject.

33. The method of claim 32, wherein the robotic orthosis comprises:
a set of appendage motion modules configured for engaging with a portion of a subject appendage;
a set of mechanical power interface modules coupled to the set of appendage motion modules and configured for facilitating movement of appendage motion modules within the set of appendage motion modules; and
a set of flexible drive shafts couplable to the set of mechanical power interface modules and a set of motors external to the wearable robotic orthosis, wherein the set of appendage motion modules and the set of mechanical power interface modules are subject wearable.

34. The method of claim 33, wherein the set of appendage motion modules includes multiple independently operable and selectively detachable appendage motion modules.

35. The method of claim 32, wherein the mind-body synergy measure that includes a breakthrough index (BTI) which quantitatively measures a likelihood that the subject can experience an accelerated or burst type functional development result, wherein the BTI is calculated as a cumulative number of voluntary muscle contractions for the body part during a time period T that (i) meet or exceed a threshold muscle contraction condition for the body part, and which (ii) are each temporally associated with each of the mind state alignment measure satisfying a mind state alignment condition and the body state alignment measure satisfying a body state alignment condition, normalized to a cumulative number of voluntary muscle contractions for the body part during the time period T that meet or exceed the threshold muscle contraction condition.

36. The method of claim 32, wherein the mind state alignment measure is determined based on a real time or near-real time basis.

37. The method of claim 32, wherein the body state alignment measure is determined based on a real time or near-real time basis.

38. The method of claim 32, wherein the sensing signals corresponding to the subject's mind state comprises detecting signals representative of intracranial neural activity.

39. The method of claim 32, wherein the sensing signals corresponding to the subject's mind state comprises sensing EEG signals.

40. The method of claim 32, wherein the sensing signals corresponding to the subject's body state comprises detecting signals corresponding to peripheral nervous system activity.

41. The method of claim 32, wherein the sensing signals corresponding to the subject's body state comprises sensing EMG signals.

42. The method of claim 32, wherein the mind state alignment measure corresponds to at least one of a level of stress, a level of anxiety, a level of mental relaxation, and a level of mental attention or focus.

43. The method of claim 32, wherein the mind state alignment measure is correlated with a ratio between a mean relative alpha band power measure $P\alpha$, and a delta-to-alpha measure DAR referenced to a particular time t, normalized to a baseline or at rest ratio between the mean relative alpha measure Pα, and the delta-to-alpha measure DAR.

44. The method of claim 32, wherein the body state alignment measure mathematically defines an extent to which subject agonist muscle contractions relevant to the set of functional development activities including a movement sequence under consideration at time t are dominant or subordinate with respect to subject antagonist muscle contraction counterproductive to the movement sequence under consideration at time t for the set of functional development activities.

* * * * *